(12) United States Patent
Rajagopalan et al.

(10) Patent No.: US 9,273,291 B2
(45) Date of Patent: Mar. 1, 2016

(54) ENZYMATIC ALKENE CLEAVAGE

(75) Inventors: Aashrita Rajagopalan, Chennai (IN); Wolfgang Kroutil, Graz (AT); Markus Schober, St. Andrae (AT)

(73) Assignee: Universitat Graz, Graz (AT)

( * ) Notice: Subject to any disclaimer, the term of this patent is extended or adjusted under 35 U.S.C. 154(b) by 0 days.

(21) Appl. No.: 14/241,210

(22) PCT Filed: Aug. 9, 2012

(86) PCT No.: PCT/AT2012/050113
§ 371 (c)(1),
(2), (4) Date: Oct. 14, 2014

(87) PCT Pub. No.: WO2013/029076
PCT Pub. Date: Mar. 7, 2013

(65) Prior Publication Data
US 2015/0064756 A1   Mar. 5, 2015

(30) Foreign Application Priority Data
Aug. 26, 2011   (AT) .............................. A 1221/2011

(51) Int. Cl.
*C12P 7/24*   (2006.01)
*C12N 9/02*   (2006.01)
*C07H 21/04*   (2006.01)

(52) U.S. Cl.
CPC ............ *C12N 9/0073* (2013.01); *C12N 9/0069* (2013.01); *C12P 7/24* (2013.01); *C12Y 114/13069* (2013.01)

(58) Field of Classification Search
CPC ........... C12P 7/24; C12P 7/14; C12N 9/0061; C12N 9/0069; C12Y 302/01004
USPC .......................................... 435/147, 166, 189
See application file for complete search history.

(56) References Cited

U.S. PATENT DOCUMENTS 6,146,865  A   11/2000  Christensen et al.

FOREIGN PATENT DOCUMENTS

WO   2009006662  A2   1/2009

OTHER PUBLICATIONS

Int'l Search Report issued Jan. 21, 2013 in Int'l Application No. PCT/AT2012/050113.
Rajagopalan et al, "Biocatalytic C=C double bond cleavage by an enzyme from *Trametes hirsuta*: Unexpected metal dependence," retrieved from the internet at http://www.biotrans.eu/documents/Poster-BIOTRANS-italy-october2011-biotrains website.pdf (Nov. 1, 2011).
Lara et al, "Biocatalytic Cleavage of Alkenes with 0 2 and *Trametes hirsuta* G FCC 047," European Journal of Organic Chemistry, vol. 2008, No. 21, pp. 3668-72 (Jul. 1, 2008).
Kurlemann et al, "Asymmetric synthesis of chiral 2-hydroxy ketones by coupled biocatalytic alkene oxidation and C?C bond formation," Journal of Molecular Catalysis, vol. 61, No. 1-2, pp. 111-116 (Nov. 1, 2009).
Mang et al, "Optimization of a biocatalytic single-step alkene cleavage of aryl alkenes," Tetrahedron, vol. 63, No. 16, pp. 3350-3354 (Mar. 15, 2007).
Aspartic peptidase A1 Nucleotide Sequence, Uniprot database accession No. B0CYE2 (Feb. 26, 2008).
Search Report issued Nov. 22, 2011 in AT Application No. 1221/2011.
Beloqui et al, "Recent trends in industrial microbiology," Current Opinion in Microbiology, vol. 11, pp. 240-248 (2008).

*Primary Examiner* — Tekchand Saidha
*Assistant Examiner* — Md. Younus Meah
(74) *Attorney, Agent, or Firm* — Panitch Schwarze Belisario & Nadel LLP

(57) ABSTRACT

The invention relates to an enzyme that comprises or includes a sequence according to SEQ. ID No. 1 or SEQ. ID No. 2, to a method for the production thereof, and to the use thereof as a catalyst in the oxidative cleavage of vinyl aromatics.

13 Claims, 26 Drawing Sheets

ClustaW of TOP10 Blast HITS

```
gi|582558949|ref|XP_566887.1|    ---MKTSAILIAALSAAASVEAGIHRMKLEKQTPSSTSLTG---TFPPSP  44
gi|321250483|ref|XP_003191823.   ---MKTSAILIAALSAAASVEAGIHRMKLEKQSLSSTSLTGDIPTFYPSP  47
gi|1700091822|ref|XP_001877133.  ---MIFLPLA-LALLSFAEASR-IHKLKLHKLPTT--------------SNP  34
gi|336373584|gb|EGO01922.1|      ---MLLSAFAPLLLLPYAAAAGGVHKLKLHKLPKVS-------------PNH  36
gi|302696543|ref|XP_003037950.   ---MILTSLF-LGLLP--AVYAEVHKLQLQKIPATV-------------GNP  33
gi|169861123|ref|XP_001837196.   ---MLLTPIV-LSLLPFTVAAR-VHKLKLHKVAPTA-------------SNP  34
gi|710216685|ref|XP_761073.1|    MKLNLSLIFVTALATAFAGVEAGVHKAKLQKVTPSRE------------LTLEGL  43
gi|327708430|gb|EFZ00008.1|      ---MKSALIAAAA-LAGTAHA-GVHKMKLQKISLEEQLA-----------GASI  38
gi|327700747|gb|EFY92500.1|      ---MKSALIAAAA-LAGTAHA-GVHKMKLQKISLKEQLA-----------DAPI  38
gi|1102774333|gb|ABG57251.1|     ---MKSALIAAAA-LVGSAQA-GVHKMKLQKVSLEQQLE-----------GSSI  38
gi|302899226|ref|XP_003048007.   ---MKSALLAAAA-LLGSAQA-GVHKMKIQKVPLAEQLA-----------TTSI  38
gi|320588396|gb|EFX00865.1|      ---MKGALVLAAAGLLGSAQASGIQKLKLKKVPLAKQLE-----------SIPI  40 gi|582558949|ref|XP_566887.1|    ELEAKWLASKYLGQEYTDQMPLGGFGGAGKKFKSGNKHTEHPEQNDEERY  94
gi|321250483|ref|XP_003191823.   ELEAKWLASKYLGQDYAKQMPLMGFDGAGKKFKSGNEHTEHHEQKDQDRY  97
gi|1700091822|ref|XP_001877133.  QFESAYLAEKYGASGSPQMPLLGVGGTGRRVA-----------MQNGEP--LF  75
gi|336373584|gb|EGO01922.1|      GLESAYLAEKYGAETTYQQLPLMGAGGAGRHIR-----------PDRPEDSDLF  79
gi|302696543|ref|XP_003037950.   ELESLHLAEKYGVVN-EFQTPLMGAGGAGRRLK-----------NDAGED--LF  73
gi|169861123|ref|XP_001837196.   DFEVAYLSQKYGSSA-SVQLPLMGAGGAARVAR-----------PDSRDGEQLF  77
gi|710216685|ref|XP_761073.1|    AAQAEILQLKYGGGSSKKQVPFSSNPEHDFSIQP----------IADSSQAAAW  87
gi|327708430|gb|EFZ00008.1|      EQHVRALGQKYLG-ARPASRASVMFNTKAPQVAE----------------  71
gi|327700747|gb|EFY92500.1|      EQHVQALGQKYIG-ARPPSRASVMFNTKAPQVAG----------------  71
gi|1102774333|gb|ABG57251.1|     EAQVQQLGQKYMG-VRPTSRVDVMFNDNVPKVKG----------------  71
gi|302899226|ref|XP_003048007.   ETHIQNLGQKYLGSARPKNQADYAFSTEAINVEG----------------  72
gi|320588396|gb|EFX00865.1|      DAQIRGLGQKYMG-ARLGSHADEMFKTAVVETDD----------------  73 gi|582558949|ref|XP_566887.1|    WAQMVDQSAHSQMIDVLKGGHGVPLSNYMNAQYFATMEIGTPFQTFKVIL  144
gi|321250483|ref|XP_003191823.   WAQMVD-------MLKDGHGVPLSNYMNAQYFAQIELGTPAQTFKVIL  138
gi|1700091822|ref|XP_001877133.  WTQDEL-------KGGHSVPLSNFMNAQYFTEISIGNPPQSFKVIL  114
gi|336373584|gb|EGO01922.1|      WTQEELV-------KGGHGVPLINFMNAQYYTEITLGSPAQTFKVIL  119
gi|302696543|ref|XP_003037950.   WTQEQV--------KGGHGVPLINFMNAQYFTEITLGTPPQNFKVIL  112
gi|169861123|ref|XP_001837196.   WTQDDL--------KNGHKVPLITNFMNAQYYTEITLGTPPQTFKVIL  116
gi|710216685|ref|XP_761073.1|    YAFAKK--------GHGVPLTDFLNAQYFCDISLGTPAQDFKVIL  124
gi|327708430|gb|EFZ00008.1|      ---------GHPVPVSNFMNAQYFSEITVGTPPQTFKVVL  102
gi|327700747|gb|EFY92500.1|      ---------GHPVPVSNFMNAQYFSEITIGSPPQSFKVVL  102
gi|1102774333|gb|ABG57251.1|     ---------GHPVPVTNFMNAQYFSEITIGSPPQTFKVIL  102
gi|302899226|ref|XP_003048007.   ---------GHPVPISNFMNAQYFSEITIGNPPQSFKVVL  103
gi|320588396|gb|EFX00865.1|      ---------NHPLPVSNFLNAQYFAEISIGTPPQSFKVVL  104
```

Figure 14A

ClustaW of TOP10 Blast HITS (continued)

```
gi|582589491|ref|XP_566887.1|       DTGSSNLWVPSVKCTSIACFLHSKYDSSQSSTYKANGSDFEIHYGSGSLE 194
gi|321250483|ref|XP_003191823.      DTGSSNLWVPSVGCTSIACFLHSKYDSSQSSTYKANGSDFEIHYGSGSLE 188
gi|170091822|ref|XP_001877133.      DTGSSNLWVPSVKCTSIACFLHTKYDSASSSTFKANGSEFSIHYGSGSME 164
gi|336373584|gb|EGO01922.1|         DTGSSNLWVPSKKCTSIACFLHTKYDSSSSSTYKANGTEFSIQYGSGSME 169
gi|302696543|ref|XP_003037950.      DTGSSNLWVPSSKCTSIACFLHAKYDSSASSTYKQNGTEFSIQYGSGSME 162
gi|169861123|ref|XP_001837196.      DTGSSNLWVPSIKCTSIACFLHTKYDSSQSTTYKANGTEFKIQYGSGSME 166
gi|710216851|ref|XP_761073.1|       DTGSSNLWVPSTKCSSIACFLHKKYDSSASSSYKKNGTEFKIQYGSGSME 174
gi|322708430|gb|EFZ00008.1|         DTGSSNLWVPSQSCSSIACYLHSTYDSSSSSTYKKNGSSFEIRYGSGSLS 152
gi|322700747|gb|EFY92500.1|         DTGSSNLWVPSQSCNSIACYLHSTYDSSSSSTYKKNGSSFEIRYGSGSLS 152
gi|110277433|gb|ABG57251.1|         DTGSSNLWVPSQSCNSIACFLHSTYDSSSASSYKNGSDFEIHYGSGSLT 152
gi|302899226|ref|XP_003048007.      DTGSSNLWVPSQECGSIACYLHSKYDSSASSTYKQNGSEFEIHYGSGSLS 153
gi|320588396|gb|EFX00865.1|         DTGSSNLWVPSSQCGSIACYLHTKYDSESSSSYKSNGSAFAAQYGSGSLS 154
                                    ***: *  :******                 . :*::*  *****::

gi|582589491|ref|XP_566887.1|       GFISQDTVSIGDLVVKKQDFAEATKEPGLAFAFGKFDGILGLGYDTISVN 244
gi|321250483|ref|XP_003191823.      GFISQDTLAIGDLAIKGQDFAEATKEPGLAFAFGKFDGILGLGYDTISVN 238
gi|170091822|ref|XP_001877133.      GFVSNDLLSIGDITIKGDITIKGQDFAEATKEPGLAFAFGKFDGILGLGYDTISVN 214
gi|336373584|gb|EGO01922.1|         GFVSQESMKIGDLSIQHQDFAEATKEPGLAFAFGKFDGILGLGYDTISVN 219
gi|302696543|ref|XP_003037950.      GFVSQDVLTIGDLTIPGQDFAEAVKEPGLTFAFGKFDGILGLGYDTISVN 212
gi|169861123|ref|XP_001837196.      GFVSQDTLGIGDLTIKGQDFAEALKEPGLAFAFGKFDGILGLAYDTISVN 216
gi|710216851|ref|XP_761073.1|       GIVSNDVLKIGDLTIKGQDFAEATSEPGLAFAFGKFDGILGLAYDTISVN 224
gi|322708430|gb|EFZ00008.1|         GFVSQDVVTIGDLKIKDQDFAEATSEPGLAFAFGKFDGILGLGYDTLSVN 202
gi|322700747|gb|EFY92500.1|         GFVSQDVVSIGDLKIEHQDFAEATSEPGLAFAFGKFDGILGLGYDTLSVN 202
gi|110277433|gb|ABG57251.1|         GFISNDVVTIGDLQIKGQDFAEATSEPGLAFAFGRFDGILGLGYDTISVN 203
gi|302899226|ref|XP_003048007.      GFISNDDVSIGDLKIKGQDFAEATKEPGLAFAFGRFDGILGLGYDTISVN 203
gi|320588396|gb|EFX00865.1|         GFVSQDTVSIGDLKIVKQDFAEATEEPGLAFAFARFDGILGFDTISVN 204
                                    * :.:   .:**  :  ***** :******.::**  *::*
```

ENZYMATIC ALKENE CLEAVAGE

CROSS-REFERENCE TO RELATED APPLICATION

The application is a is a Section 371 of International Application No. PCT/AT2012/050113, filed Aug. 9, 2012, which was published in the German language on Mar. 7, 2013, under International Publication No. WO 2013/029076 A1, and the disclosure of which is incorporated herein by reference.

REFERENCE TO SEQUENCE LISTING SUBMITTED ELECTRONICALLY

This application contains a sequence listing, which is submitted electronically via EFS-Web as an ASCII formatted sequence listing with a file name "Substitute_Sequence_Listing.TXT", creation date of Oct. 14, 2014, and having a size of 86406 bytes. The sequence listing submitted via EFS-Web is part of the specification and is herein incorporated by reference in its entirety.

FIELD OF THE INVENTION

The invention relates to an enzyme isolated from a fungal culture for the first time, its use in catalyzing alkene cleavage reactions and a method for its preparation.

PRIOR ART

Cleaving aliphatic double bonds of vinyl aromatics using enzymatic cleavage has been known for some time. For example, WO 96/22381 A1 and the related U.S. Pat. No. 5,861,286 A describe such oxidations in the presence of proteins, which can optionally be various metalloproteins or enzymes such as haemoglobin or protoporphyrin, or of metallic ions. As the only example that uses a protein having a structure other than that of a protoporphyrin, eggplant pulp is used as a catalyst instead, and while this eggplant pulp is referred to as having "a certain oxidative enzymatic effect" due to its protein content, this is not further specified. Field et al., Eur. J. Biochem. 265, 1008-1014 (1999), describe the oxidation of isoeugenol acetate with lignin peroxidase using $H_2O_2$ in the presence of veratryl alcohol. Tadao et al., Bioorg. Med. Chem. Lett. 12(8), 1139-1142 (2002), describe the cleavage of stilbenes by lignostilbene $\alpha,\beta$-dioxygenase using oxygen.

Also the present inventors have developed new and efficient enzyme-catalytic methods of cleaving vinyl aromatics in the course of previous research. In WO 2009/006662 A2, for example, they disclose a method using enzymatic catalysis by certain peroxidases and laccases, which surprisingly make use oxygen as a substrate, and in WO 2010/003161 A1, they disclose a similar method using enzymatic catalysis by certain haemins, also in the presence of oxygen.

In addition, they had previously found that adding cells or cell extracts of a certain fungus, i.e. Trametes hirsuta (hairy bracket), can also catalyze such oxidations in the presence of oxygen (Kroutil et al., Angew. Chem. 118, 5325-5328 (2006) and Angew. Chem. Int. Ed. 45, 5201-5203 (2006)), but it could not be clarified which enzyme(s) is/are responsible, as isolating the relevant enzymatic activity has always failed so far.

It is thus an object of the invention to isolate and analyze the enzyme, or enzymes, having this enzymatic activity.

DISCLOSURE OF THE INVENTION

The present invention achieves this goal by providing a previously unknown enzyme having or comprising the sequence of SEQ ID NO: 1 or SEQ ID NO: 2, that has been isolated for the first time. SEQ ID NO: 1 is equal to the sequence determined by primer walking, while SEQ ID NO: 2 represents the sequence obtained by conclusive sequencing of the enzyme then isolated from Trametes hirsuta, with the two differing only by a single amino acid. This difference concerns an alanine in the terminal sequence as opposed to a valine in the one determined by primer walking. As both amino acids belong to the group of apolar aliphatic amino acids, such replacement is regarded as a "conservative substitution", which is why an enzyme having the sequence determined by primer walking will, with high probability, have similar characteristics and activities as the isolated amino acid sequence.

As is well-known by those skilled in the art, the characteristics of protein homologs are increasingly similar with increasing identity of amino acid sequences. Therefore, the higher the degree of identity of the amino acid sequence of a protein or enzyme is to that of SEQ ID NO: 1 or SEQ ID NO: 2, the better its activity as a reaction catalyst in the alkene cleavage reactions will be. As a result, a protein having an amino acid sequence with at least 80%, preferably at least 90%, more preferably at least 95%, particularly at least 99%, identity to SEQ ID NO: 1 or 2, will have at least comparable, or even the same, activity as the isolated enzyme.

Initially, the isolated enzyme having SEQ ID NO: 2 hardly exhibited any effectiveness as a catalyst for cleaving alkenes with oxygen. Surprisingly, however, the inventors have found that the catalytic activity of the enzyme could be increased dramatically if $Mn^{3+}$ ions are present in the reaction mixture. Accordingly, this enzyme seems to require the presence of manganese(III) as a co-factor in order to be catalytically effective in the above reaction to a satisfying degree, even though, generally, enzymes with comparable activities usually have iron or copper dependencies. Also, enzymes with similar amino acid sequences as the enzyme of the invention are usually proteinases, which show no activity whatsoever as catalysts in alkene cleavage reactions. This is why the activity found by the inventors was all the more surprising.

In a second aspect, the invention comprises the use of an enzyme according to the first aspect of the invention—or a protein having at least 80%, %, preferably at least 90%, more preferably at least 95%, and particularly at least 99%, identity to SEQ ID NO: 1 or 2, as a catalyst for cleaving vinyl aromatics with oxygen, with the cleavage being preferably in the presence of $Mn^{3+}$ ions in order to increase enzyme activity, as set out above.

In a third aspect, the invention comprises a method of preparing an enzyme of the invention by culturing a culture of Trametes hirsuta and recovering the enzyme from a cell-free extract of the culture, with a culture of Trametes hirsuta G FCC 047 being preferably cultured since the inventors have achieved good results with this strain. Further, in preferred embodiments, recovery from the cell-free extract is performed using a combination of hydrophobic interaction chromatography and anion exchange chromatography, in particular using hydrophobic interaction chromatography, anion exchange chromatography and again hydrophobic interaction chromatography, in this order.

Finally, in a fourth aspect, the invention comprises a method of recombinantly producing the enzyme according to the first aspect of the invention using nucleic acid encoding the enzyme, i.e. nucleic acid having a nucleotide sequence according to SEQ ID NO: 3 or 4, with the first corresponding to the nucleotide sequence encoding SEQ ID NO: 1 and the latter corresponding to the nucleotide sequence encoding SEQ ID NO: 2. The two sequences were obtained as described in more detail below. The nucleic acid encoding the enzyme is preferably ligated into a vector, e.g. a plasmid vector, used to transform cells capable of expressing the enzyme, such as *E. coli* cells but also other prokaryotic or eukaryotic cells, e.g. *Pichia pastoris* cells. Following appropriate incubation of the transformed cells, the enzyme of the invention is recovered from the culture broth by techniques known in the art, preferably as a cell-free extract, and stored, preferably in a lyophilized state.

Examples of the methods according to the invention are described in more detail below.

BRIEF DESCRIPTION OF THE DRAWINGS

The invention is described in further detail below, referring to the accompanying drawings, which show the following:

FIG. 14 shows ClustaW sequence alignment results of primer walking 3 (SEQ ID NOs: 84-95).

FIG. 21 shows a comparison of amino acid sequences encoded by the isolated gene (SEQ ID NO: 2) and by the one assembled from partial primer walking segments (SEQ ID NO: 1).

FIG. 22 shows a comparison of sequences of the gene obtained from genomic DNA (SEQ ID NO: 96) and the one obtained as a template (SEQ ID NO: 4).

NOMENCLATURE

Designations of nucleotide sequences herein use the usual one-letter code, i.e. A for adenine, C for cytosine, g for guanine and T for thymine (in both upper and lower case). Designations of amino acids of amino acid sequences disclosed in the present description and in the sequence listing is in one-letter and three-letter codes as indicated below for overview.

| Amino acid | Three-letter code | One-letter code |
| --- | --- | --- |
| alanine | Ala | A |
| arginine | Arg | R |
| asparagine | Asn | N |
| aspartic acid | Asp | D |
| cysteine | Cys | C |
| glutamine | Gln | Q |
| glutamic acid | Glu | E |
| glycine | Gly | G |
| histidine | His | H |
| isoleucine | Ile | I |
| leucine | Leu | L |
| lysine | Lys | K |
| methionine | Met | M |
| phenylalanine | Phe | F |
| proline | Pro | P |
| serine | Ser | S |
| threonine | Thr | T |
| tryptophane | Trp | W |
| tyrosine | Tyr | Y |
| valine | Val | V |

DETAILED DESCRIPTION OF THE INVENTION 1.1 Introduction

Figure 1:
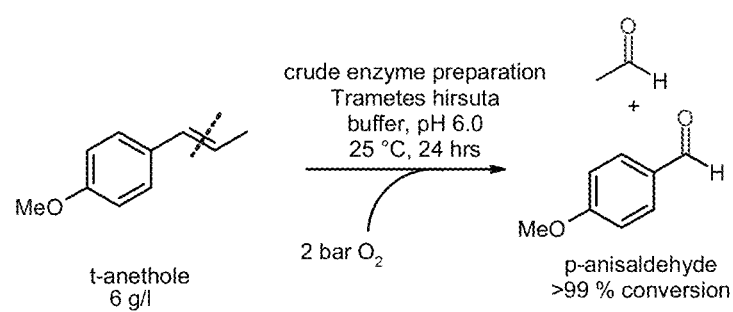
FIG. 1 shows the reaction scheme of cleaving trans-anethole using a cell-free extract of *Trametes hirsuta* as the catalyst.

*Trametes hirsuta* (*Coriolus hirsuta*) is a fungus which belongs to the white-rot fungal family. Alkenes possessing a C=C double bond adjacent to an aromatic ring were cleaved to yield the corresponding carbonyl compound by use of molecular oxygen as the sole oxidant and a cell-free extract of *Trametes hirsuta* G FCC 047 culture as a catalyst. trans-anethole has shown to be the best substrate for the biocatalytic alkene cleavage, affording p-anisaldehyde as the sole product. The conditions required to carry out this reaction were optimized previously and are indicated in FIG. 1.

The purification of this alkene-cleaving enzyme from the cell-free extract of *Trametes hirsuta* culture has been attempted several times before. It was always found to be problematic as the activity of the enzyme was already lost after two steps, or even a single step, of purification (hydrophobic interaction chromatography, followed by size exclusion chromatography). The exact cause of this loss of activity was unknown. However, it was suspected that there was a loss of the enzyme co-factor responsible for the reaction, during the column purification. Further research was done to assay the metal dependence of the enzyme.

1.2 Results and Discussion

1.2.1 Mn(III) Dependence of the Alkene-Cleaving Enzyme and Purification of the Enzyme from the Cell-Free Extract

1.2.1.1 Mn(III) Co-Factor Dependency of the Alkene Cleavage Activity

During further research on the intracellular enzymes of *Trametes hirsuta* G FCC047, surprisingly, an influence of Mn(III) on alkene cleavage activity was found. To find out if the addition of Mn(III) in the fungi culture with poor alkene cleavage activity had any effect on the alkene cleavage activity, Mn(III) salt solution was added to the biotransformation reaction mixture. The reaction was carried out in triplicates using t-anethole as the standard substrate. The sample composition and the obtained conversions (%) are summarized in Table 1.

TABLE 1

Effect of $Mn^{3+}$ on t-anethole with and without CFE (cell-free fungal extract) in a three-way approach: conversion of t-anethole to p-anisaldehyde after 10 hours while periodically adding 10 μL of $Mn^{3+}$ acetate solution (1 mM)

| Sample composition | Conversion (%) | | |
|---|---|---|---|
| | 1 | 2 | 3 |
| 800 μL Bis-tris buffer (pH 6) + 5 μL t-anethole + Mn(III) | 1 | 1 | 1 |
| 800 μL I CFE 1 + 5 μL t-anethole + Mn(III) | 9 | 15 | 11 |
| 800 μL CFE 1 + 5 μL t-anethole | 7 | 7 | 8 |
| 800 μL Bis-tris buffer (pH 6) + 5 μL t-anethole (negative control) | 0.7 | 0.6 | 0.6 |

It could be concluded from the study that the addition of Mn(III) to the cell-free extract was definitely having an influence on the alkene cleavage activity, as there was a considerable increase in the conversion (%) from t-anethole to the p-anisaldehyde.

1.2.1.2 Purification of the Enzyme from the Cell Free Extract of *Trametes hirsuta*

1.2.1.2.1 Information from Previously Attempted Purification Work

Purification of the enzyme has been attempted several times before. Even though it could not be purified as the activity was always lost after two steps of purification, some valuable information was gathered. The first step of purification employed was always hydrophobic interaction chromatography (phenyl sepharose CL-4B). After this step, the enzyme was still active. This was a neat process, as it was consistent with the fractions in which the enzyme activity was present and also repeatable. Previously, size-exclusion chromatography was employed as the second step. Hardly any activity could be obtained after this step. However, based on the few fractions which gave little activity the size of the enzyme was predicted to be between 140 and 160 KDa. Positive fractions from the first step (HIC) were also subjected to ICP-MS studies to detect the metals present. Only three metals were detected: Mn, Cu and Mo. It was suspected that some key metal/metals were getting lost during the purification process, hence the loss of activity. The study of the mechanism showed that the enzymatic activity involves metal capable of one electron transfer. It was also tested if the activity of the enzyme could be recovered by adding various metals ($Cu^{1+}$, $Cu^{2+}$, $Mn^{2+}$, $Mo^{3+}$ and $Mo^{5+}$). All known alkene-cleaving enzymes in literature exhibit either iron or copper. None of the metals tested with the different oxidation states could recover the lost activity. This was another clue that the not previously tested Mn(III) could be the involved co-factor for the alkene cleavage activity.

1.2.1.2.2 Preparation of Cell-Free Extract and Column

The cell-free extract was prepared using the lyophilized *T. hirsuta* culture. A decent concentration of culture (of 44 mg lyophilized culture/mL of buffer) was subjected to cell disruption by means of ultrasonication. Cell debris was removed from the crude extract, and the supernatant was subjected to purification. The column used for the first step was self-packed (Phenylsepharose CL-4B). For the rest of the steps, commercially available pre-packed columns were used.

1.2.1.2.3 Hydrophobic Interaction Chromatography (Step 1)

The self-packed phenyl sepharose column was used. This step was repeatable, and the enzyme activity was always detected in the fractions corresponding to the second peak, which appeared after the end of the salt (ammonium sulfate) gradient, in water. The chromatogram diagram obtained is given in FIG. 2.

Figure 2:
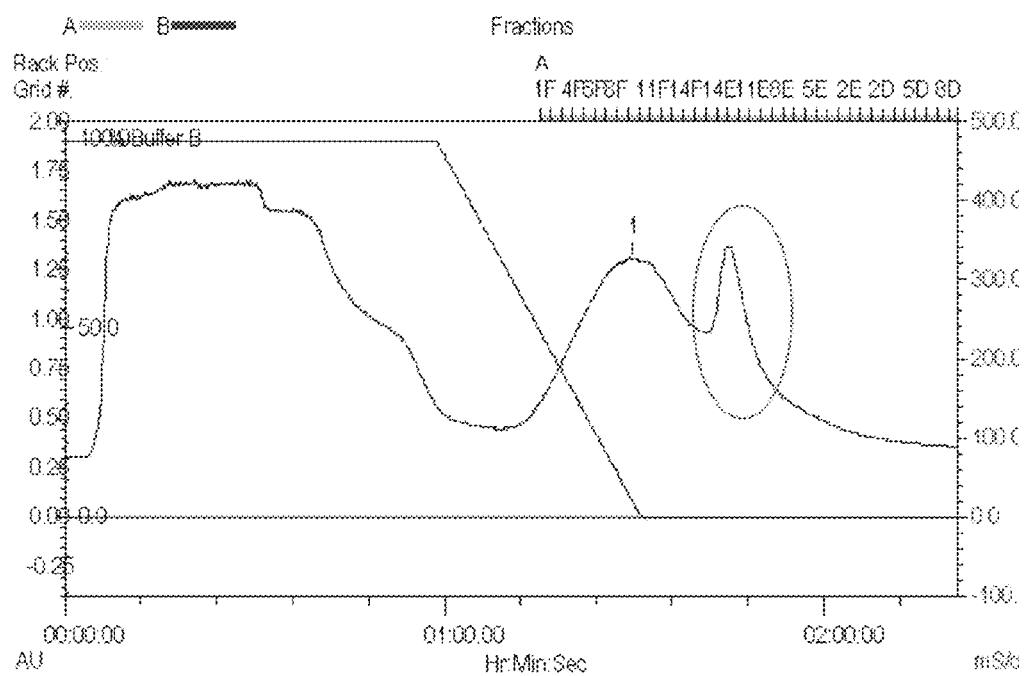
FIG. 2 shows the chromatogram of hydrophobic interaction chromatography performed as a first purification step.

The circled region in FIG. 2 is where enzyme activity is always found (second peak after the end of the salt gradient). The fractions corresponding to this region were pooled for the next step of purification.

1.2.1.2.4 Anion Exchange Chromatography (Step 2)

The commercially available HiTrap® FF Q, anion-exchange column (1 mL) was used in this step. The pooled positive fractions from the previous step (45 mL) was loaded onto the column for further purification. Positive fractions were tested by addition of minimum amounts (0.4 mM) of Mn(III) acetate, which did not in itself catalyze the alkene cleavage. After the second step of purification, enzymatic activity was observed for the first time.

Figure 3:
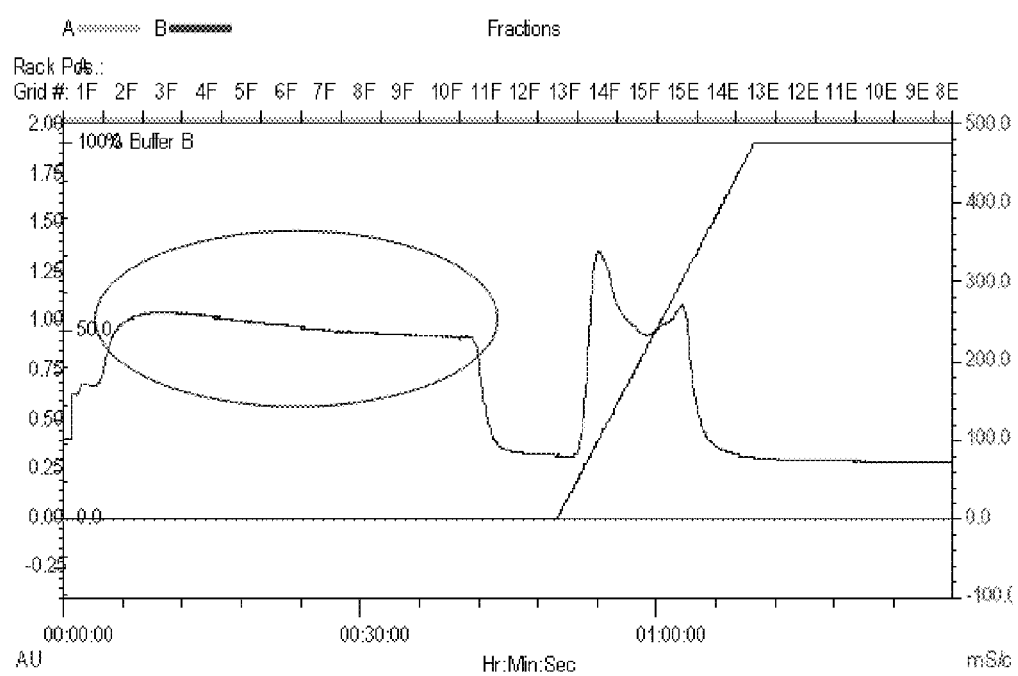
FIG. 3 shows the chromatogram of anion exchange chromatography performed as a second purification step.

The enzyme was eluted from the flow-through fractions, which means that the enzyme did not bind to the column. The other proteins, which did bind to the column, were eluted with an increasing linear salt (NaCl) concentration gradient. Samples from the fractions were collected for protein concentration evaluation and for SDS-PAGE. The positive fractions (flow-through) were then pooled for further purification. The chromatogram is shown in FIG. 3. The average protein concentration of the flow-through fractions (2 to 11) were found to be 428 μg protein/mL. The circled area is where enzyme activity occurred (flow-through fractions).

Figure 4:
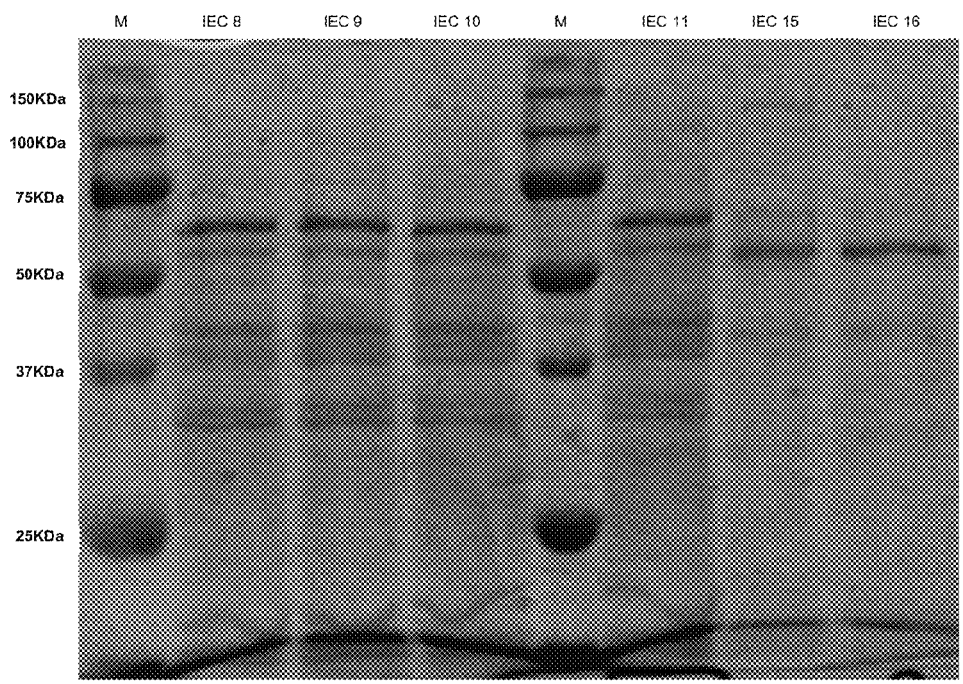
FIG. 4 shows the electropherogram of SDS-PAGE on anion exchange chromatography samples.

FIG. 4 shows the electropherogram of an SDS-PAGE of anion exchange chromatography samples. Fractions 8, 9, 10 and 11 were the active fractions (flow-through). Fractions 15 and 16 were negative fractions.

1.2.1.2.5 Hydrophobic Interaction Chromatography (Step 3)

Figure 5:
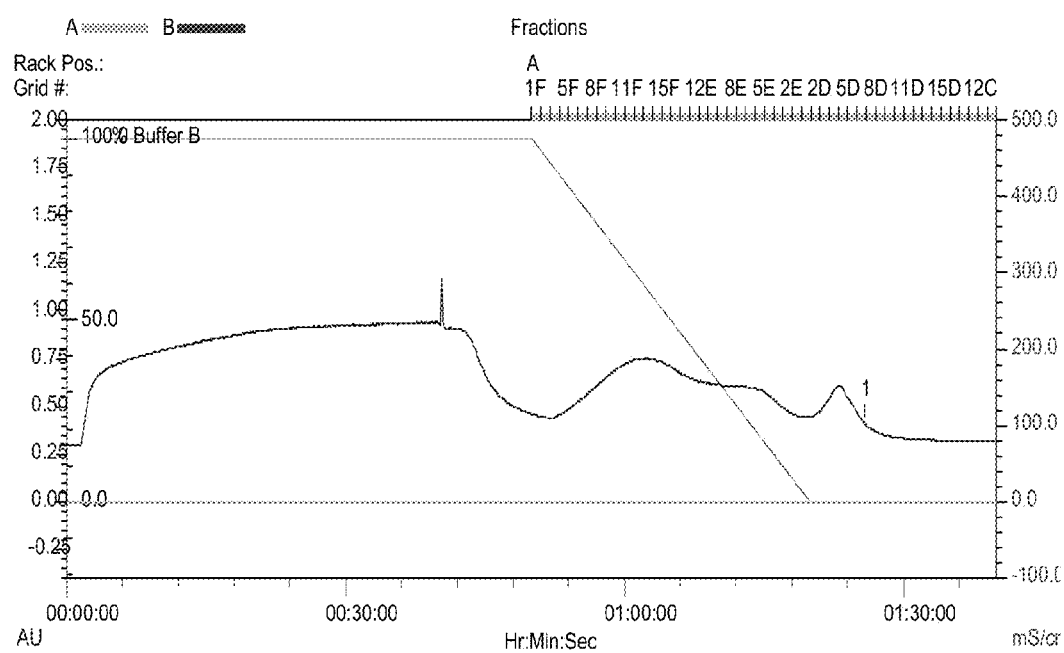
FIG. 5 shows the chromatogram of hydrophobic interaction chromatography performed as a third purification step.
Figure 6:
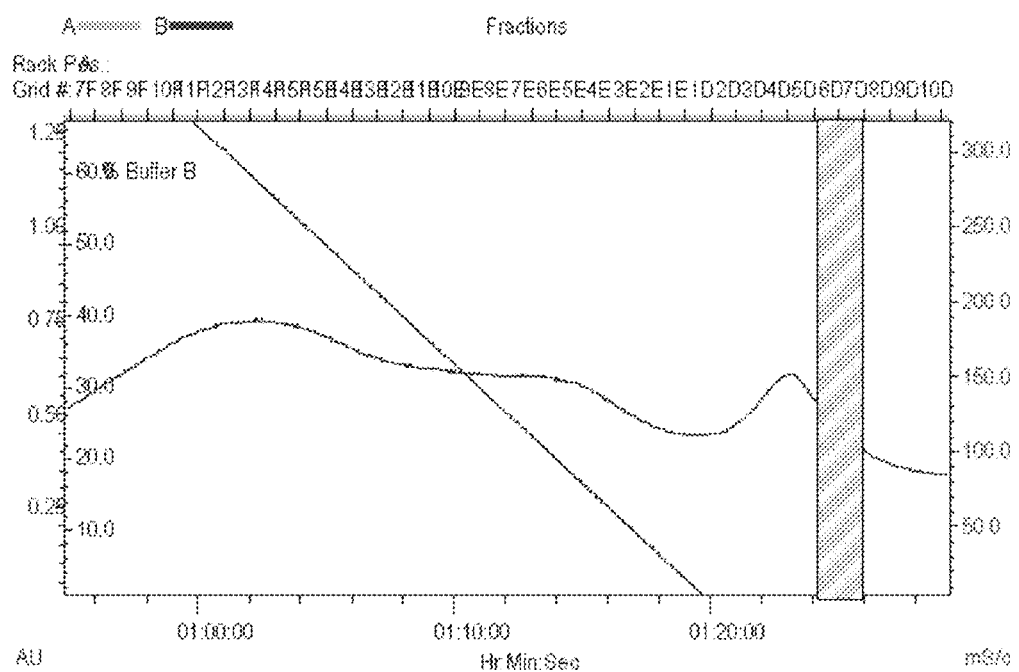
FIG. 6 is an enlarged view of a part of the chromatogram of FIG. 5.

A commercially available Hitrap® Phenyl HP (1 mL) hydrophobic interaction column was used for the final step of purification. Steps 1 and 2 were performed twice to get sufficient amounts of sample for step 3 (the final step). The pooled sample from the anion exchange chromatography (performed twice, resulting in a volume of about 80 mL with about 428 μg protein/mL) was loaded onto the HIC column. The first time the experiment was performed all fractions were tested for activity. It was then clear where the enzyme of interest eluted. The region was similar to where it eluted in Step-1 HIC (after the end of the ammonium sulfate gradient, in water). When the entire experiment was repeated for the second time, part of the fractions (700 μL) after the ammonium sulfate concentration gradient were collected and tested for activity to find the active fractions. The remaining amount in the fractions was stored for protein concentration estimation and for SDS-PAGE. Fraction 36 showed the highest activity (16% conversion from t-anethole to p-anisaldehyde under reaction conditions). It had a protein concentration of approximately 150 μg protein/mL The chromatogram obtained is given in FIG. 5. Enzyme activity was found in two fractions after the end of the ammonium sulfate concentration gradient. FIG. 6 is a magnified view of the chromatogram in FIG. 5. The hatched area shows the fractions in which enzyme activity was found (fractions 36 and 37).

1.2.1.3 SDS-PAGE of the Active Fraction and Amino Acid Sequence Analysis

Figure 7:
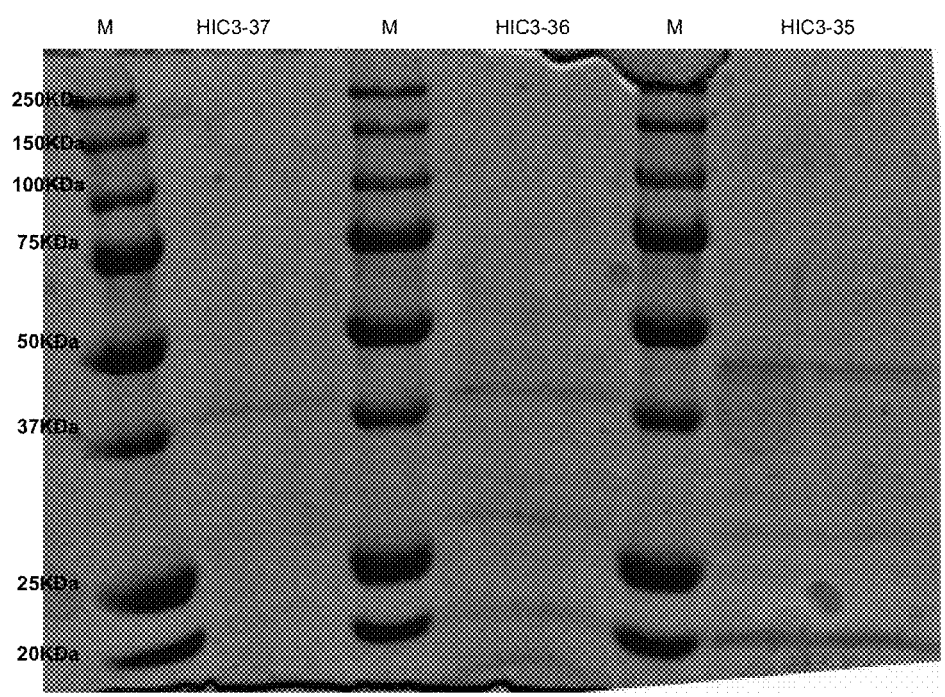
FIG. 7 shows the electropherogram of SDS-PAGE of the hydrophobic interaction chromatography samples of the third purification step.
Figure 8:
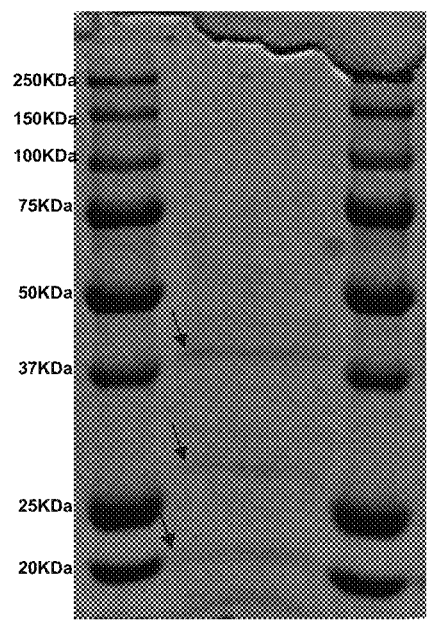
FIG. 8 shows the electropherogram of SDS-PAGE of the most active fraction after hydrophobic interaction chromatography.

SDS-PAGE of the active fraction revealed three main bands. One was in the area of 37 kDa, one was in the area of 25 kDa and the last one was in the area of 20 kDa. FIG. 7 is the electropherogram of fractions 35, 36 and 37 of the purification by hydrophobic interaction chromatography as purification step 3. Fraction 6 was the most active fraction. As the protein concentration of the fractions was low, two indentations in the gel were connected in order to achieve one larger indentation, and 80 μL of sample (fraction/loading buffer=50/50) were filled into each indentation. Comparison between the positive fraction (HIC3-36) and the negative fraction (HIC3-35) suggests that the band at approximately 37 kDa was a unique band for the positive fraction. The band at approximately 37 kDa was excised from the gel and sent to PROTAGEN AG in Dortmund, Germany for MALDI MS-MS analysis and de novo sequencing.

1.2.2 Amino Acid Sequencing of the Obtained SDS Gel Band

This section is partly a copy of the data and report received from PROTAGEN AG.

1.2.2.1 Protein Identification by MALDI-MS/MS and De Novo Sequencing

1.2.2.1.1 In-Gel Digestion

The selected protein spot was excised from the gel. The gel plug was washed alternately three times with 15 μL 10 mM NH$_4$HCO$_3$ and 5 mM NH$_4$HCO$_3$/50% acetonitrile. After drying the gel segment, trypsin solution (33 ng/μL in 10 mM NH$_4$HCO$_3$, pH 7.8) was added to digest the protein for several hours at 37° C.

1.2.2.1.2 MALDI Sample Preparation

The peptides were extracted from the gel segment using 0.1% trifluoroacetic acid (TFA) and purified using C18 material (ZipTip™, Millipore, Bedford, Mass., USA) before spotting them onto the MALDI target.

1.2.2.1.3 MALDI Spectrum Acquisition

The protein identification was performed using an Ultraflex III TOF/TOF mass spectrometer (Bruker Daltonics). For the acquisition of peptide mass fingerprint spectra (PMF, MS), 200 single shot spectra were averaged and peak picking was performed using the SNAP algorithm. The resulting mass list was sent to the ProteinScape™ database for protein identification. Peptide fragmentation spectra (PFF, MS/MS) were acquired where possible. The peaks for fragmentation were selected by the ProteinScape database based upon the results of the protein identification by PMF.

1.2.2.1.4 Protein Identification Using a Public Database

Protein identification was performed by searching the mass spectra against the NCBI protein database (website: www.ncbi.nlm.nih.gov) using several external search algorithms (ProFound™, Mascot™, Sequest™). For PMF spectra, the mass tolerance was set to 50 ppm. The protein identification was based on the metascore1 calculated from the individual search results by the ProteinScape™ database and on manual inspection of the data where needed. PFF spectra were either used to confirm the protein already identified by PMF or for identification of proteins that eluded the PMF identification.

1.2.2.1.5 Automated De Novo Sequencing

The MS/MS data sets were automatically de-novo sequenced using the PEAKS 4.5 software package. The top scoring sequences are reported for each MS/MS spectrum.

1.2.2.1.6 Database Search

The following protein was identified by database search: gi|170091822|ref|XP_001877133.1| aspartic peptidase A1 [*Laccaria bicolors* S238NH82]. The peptide EPGLAFAFGK (SEQ ID NO: 5) could be identified by database search and could be mapped to this protein.

1.2.2.1.7 De Novo Sequencing

Sample PG379-U11-2010-001

The following peptide sequences (SEQ ID NOs: 5-13) were obtained by de novo sequencing. The amino acids, shown in bold, are identified with very high confidence (PEAKS Score of this sequence part >90%).

| Parent mass | Peptide |
|---|---|
| 1036.5482 | E P G L A F A F G K* |
| 1166.6215 | L V D S P V F S F R |
| 1301.6235 | K Y Y T V Y D H G R |
| 2041.0100 | N Q D F A E A T K E P G L A F A F G K |
| 1173.5321 | Y Y T V Y D H G R |

-continued

| Parent mass | Peptide |
|---|---|
| 1366.6850 | A Y W E V E L E S I K |
| 2375.0981 | L G S S E E D G G E A L F G G V D E T A Y S G K |
| 1023.4805 | N Q D F A E A T K |
| 1494.7802 | K A Y W E V E L E S I K |

*Also found by database searching

These peptides were identified by de novo sequencing and could be mapped to gi|17009182 by high sequence homology between the peptide identified by de novo sequencing and a sequence region of gi|17009182. Thus, it is assumed that all peptides are part of the same protein.

1.2.3 Identification of the Gene Sequence of the Alkene Cleaving Enzyme

1.2.3.1 PCR Using Designed Degenerate Primers and cDNA of *Trametes hirsuta* as the Template

1.2.3.1.1 Initial PCR Reaction Optimization

PCR using the different combinations of designed forward and reverse degenerated primers were carried out. Based on the mapping of the obtained sequences with the amino acid sequence of aspartic peptidase A1 of *Laccaria bicolor*, three forward primers and two reverse primers were designed. Using these, six different combinations of forward and reverse primers were made. In order to check which temperature was suitable for the PCR, three temperatures lower than the melting points of the primers were tested. The different combinations of the primers are given in Table 2. The PCR conditions used are given in Table 3. The program of PCR reactions is given in Table 4.
Key:

Fwd primer 1:
(SEQ ID NO: 14)
AAY CAR GAY TTY GCN GAR GC (SEQ ID NO: 19)
NQDFAEA

Fwd primer 2:
(SEQ ID NO: 15)
GAR GAR GAY GGN GGN GAR GCN (SEQ ID NO: 20)
EEDGGEA

Fwd primer 3:
(SEQ ID NO: 16)
AAR GCN TAY TGG GAR GTN GA (SEQ ID NO: 21)
KAYWEVE

Reverse primer 1:
(SEQ ID NO: 17)
TC NAC YTC CCA RTA NGC YTT (SEQ ID NO: 22)
KAYWEVE

Reverse primer 2:
(SEQ ID NO: 18)
C RTG RTC RTA NAC NGT RTA RTA YT (SEQ ID NO: 23)
KYYTVYDHG

TABLE 2

Sample numbering for the different combinations of forward and reverse degenerate primers

| Sample No. | Primer combination |
|---|---|
| 1 | Fwd primer 1 and reverse primer 1 |
| 2 | Fwd primer 1 and reverse primer 2 |
| 3 | Fwd primer 2 and reverse primer 1 |
| 4 | Fwd primer 2 and reverse primer 2 |
| 5 | Fwd primer 3 and reverse primer 1 |
| 6 | Fwd primer 3 and reverse primer 2 |

TABLE 3

Reaction components for PCR using the different combinations of primers

| | Primer combinations (1-6) | | |
|---|---|---|---|
| Contents | a (47.1° C.) (µL) | b (50.2° C.) (µL) | c (53° C.) (µL) |
| Buffer (5X HF) | 10 | 10 | 10 |
| dNTPs (10 mM) | 1 | 1 | 1 |
| Forward primer (1/10 diluted) | 1 | 1 | 1 |
| Reverse primer (1/10 diluted) | 1 | 1 | 1 |
| cDNA (180.5 ng/µL) | 1 | 1 | 1 |
| Sterile water | 35.5 | 35.5 | 35.5 |
| DNA polymerase (Phusion) | 0.5 | 0.5 | 0.5 |

TABLE 4

PCR program used to assay different temperatures with degenerate primers

| Step | Temperature (° C.) | Time | Number of cycles |
|---|---|---|---|
| Initial denaturation | 98 | 2 min | 1 |
| Denaturation | 98 | 30 s | 40 |
| Annealing | T = 50 Gradient = 3° C. Rate = 3° C./s | 30 s | |
| Extension | 72 | 45 s | |
| Final extension | 72 | 7 min | 1 |

Figure 9:
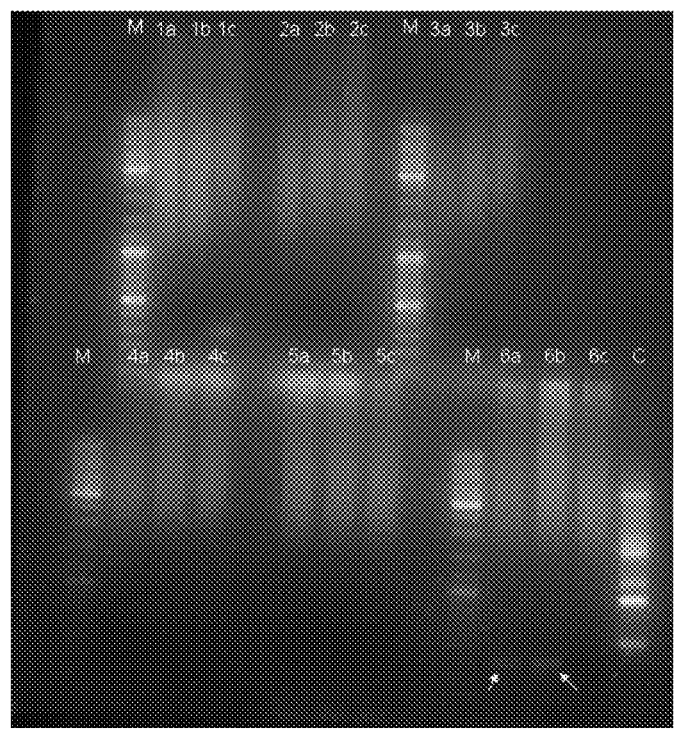
FIG. 9 shows an electropherogram of PCR products on agarose gel.

After carrying out the PCR, the samples (50 µL each) were analyzed preparatively on agarose gel (1% agarose). Three bands were visible (1c, 6a and 6b). All products were around 200 bp in size. The agarose gel picture is shown in FIG. 9. A PCR product was obtained for combinations 1c, 6a and 6b, as indicated by arrows in FIG. 9.

1.2.3.1.2 Extraction and Amplification of PCR Products

The extractions of the DNA from the bands cut out from the gel were done using the QIAGEN QIAquick® (50) Gel Extraction Kit. The DNA concentrations of the three samples (50 µL volume) were measured. The elution buffer from the kit was used as a blank.

1c—8.9 ng/µL (around 200 bp)
6a—7.6 ng/µL (around 200 bp)
6b—7.8 ng/µL (around 200 bp)

The DNA fragments were cloned and then transformed into TOP 10 *E. coli* cells for amplification of the DNA. Cloning of the DNA fragments (1c, 6a and 6b) was done using CloneJET™ PCR Cloning kit. The amount of DNA sample taken for each sample was based on the size of the fragment and the concentration of the purified DNA sample. The procedure followed the kit manual.

Overnight cultures (5 mL LB+100 µg/L Amp in each 50 mL tube) for the transformants were started (3 colonies were picked from each transformant plate). A total of 9 tubes were incubated at 37° C. with shaking at 120 rpm overnight. The backup of each of the colonies was also made on agar plates (LB+100 µg/L Amp). The plates were removed the next day and stored at 4° C.

Figure 10:
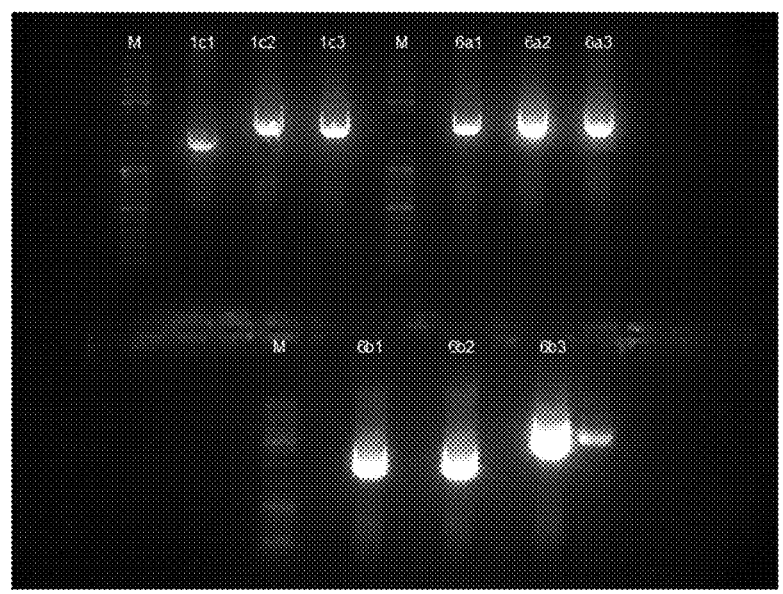
FIG. 10 shows an electropherogram of the PCR products inserted into a cloning vector.

The QIAGEN QIAprep® (250) Spin Miniprep Kit was used for performing a miniprep. The procedure followed the manual. The DNA eluted from the minipreps (50 µL each) were mixed with 6× loading buffer (8.3 µL), and the whole sample was loaded on the agarose gel (1%); see FIG. 10 showing the amplified PCR products in the CloneJET™ cloning vector. The bands of the plasmids were excised from each lane and filled into tubes (15 mL). The gel segments were weighed and the DNA was extracted using the QIAGEN QIAquick® (50) Gel Extraction Kit. The DNA concentration of the 9 samples (50 µL volume) were measured. The elution buffer from the kit was used as a blank.

1c1—20.7 ng/µL, 1c2—12.1 ng/µL, 1c3—22.8 ng/µL, 6a1—16.7 ng/µL, 6a2—14.3 ng/l, 6a3—11.8 ng/µL, 6b1—25.4 ng/µL, 6b2—20 ng/µL, 6b3—61.9 ng/µL.

1.2.3.1.3 Analysis of Insert Sequences and Design of Definite Primers for Primer Walking The sequencing results for 1c1, 6a1 and 6b1 were individually compared with the sequence of the plasmid pJET1.2 using BLAST. The non-identical region was taken as the sequence of the insert in the plasmid. This region was isolated and translated into its amino acid sequence. Using the different reading frames, the presence of the forward and reverse primers used (Fwd 1 and rev 1 in case of 1c1 and Fwd 3 and rev 2 in case of 6a1 and 6b1) was checked. It was found that both primers were only present in the 6a1 sequence. A protein BLAST with this amino acid sequence gave certain similarities to several fungal proteins belonging to the pepsin-retropepsin superfamily (the second best result was aspartic peptidase A1 from *Laccaria bicolor*). The sequence of sample 6a1 is shown below. The criteria for designing the definite primers were that both primers have GC content at the end and the melting point of both the primers should be similar. The melting point and the probability of self-complementarity on behalf of the primers were checked using the Oligo-Calc online program. In the case of the reverse primer, the reverse complement of the original DNA segment was prepared and the length was altered to suit the requirement. The primers were designed to comprise the initial degenerate primer region (to double-check the accuracy in primer walking).

```
>6a1-forward.pJET1.2-F
                                            (SEQ ID NO: 24)
TTTTTCAGCAAGAT AAGGCTTATTGGGAGGTGGA GCTGGAATCG

ATCAAACTCGGAGAC GACGAGCTTGAGCTCGATAACACCGGCGCT

GCCATCGACACTGGAACCTCGTTGATTGCTCTCCCCTCCGATCTGG

CGGAGATGCTCAATGTGCAAATCGGTGCCAAGAAGTCCTGGAATGG

TCAGTACACCGTCGACTGCGCGAAGGTCCCTACCCTCCCCGACCTC

ACCTTCTACTTCAGCGGCAAGCCTTACACTCTCAAGGGTACCGACT

ACGTCCTCGAAGTTCAGGGAACTTGCATGTCCTCGTTCACCGGCAT

CGACATCAATCTGCCCGGCGGTGGTGCTC TGTGGATCATTGGTGA

TGTCTTCCTGC GCA AGTACTACACAGTTTACGATCACG AT CT

TTCTAGAAGATCTCC TACAATATTCTCAGCTGCCATGGAAAATCG

ATGTTCTTCTTTTATTCTCTCAAGATTTTCAGGCTGTATATTAAAA

CTTATATTAAGAACTATGCTAACCACCTCATCAGGAACCGTTGTAG

GTGGCGTGGGTTTTCTTGGCAATCGACTCTCATGAAAACTACGAGC

TAAATATTCAATATGTTCCTCTTGACCAACTTTATTCTGCATTTTT

TTTGAACGAGGTTTAGAGCAAGCTTCAGGAAACTGAGACAGGAATT

TTATTAAAAATTTAAATTTTGAAGAAAGTTCAGGGTTAATAGCATC

CATTTTTTGCTTTGCAAGTTCCTCAGCATTCTTAACAAAAGACGTC

TCTTTTGACATGTTTAAAGTTTAAACCTCCTGTGTGAAATTATTAT

CCGCTCATAATTCCACACATTATACGAGCCGGAAGCATAAAGTGTA

AAGCCTGGGGTGCCTAATGAGTGAGCTAACTCACATTAATTGCGTT

GCGCTCACTGCCAATTGCTTTCCAGTCGGGAACCTGTCGTGCCAGC

TGCATTAATG
```

Amino acid sequence obtained by translation of the insert DNA sequence:

```
>EMBOSS_001_3
                                            (SEQ ID NO: 25)
FQQD KAYWEVE LESIKLGD DELELDNTGAAIDTGTSLIALPSD

LAEMLNVQIGAKKSWNGQYTVDCAKVPTLPDLTFYFSGKPYTLKGT

DYVLEVQGTCMSSFTGIDINLPGGGAL WIIGDV FLR KYYTVYD

H D
```

The underlined sequences each represent one of the following primers:
forward degenerate Primer
reverse degenerate Primer
start of vector sequence
designed definite forward primer (PW-1 Fwd)
designed definite reverse primer (PW-1 Rev)

1.2.3.2 Primer Walking 1

1.2.3.2.1 Design of Primers for the cDNA End

Figure 11:
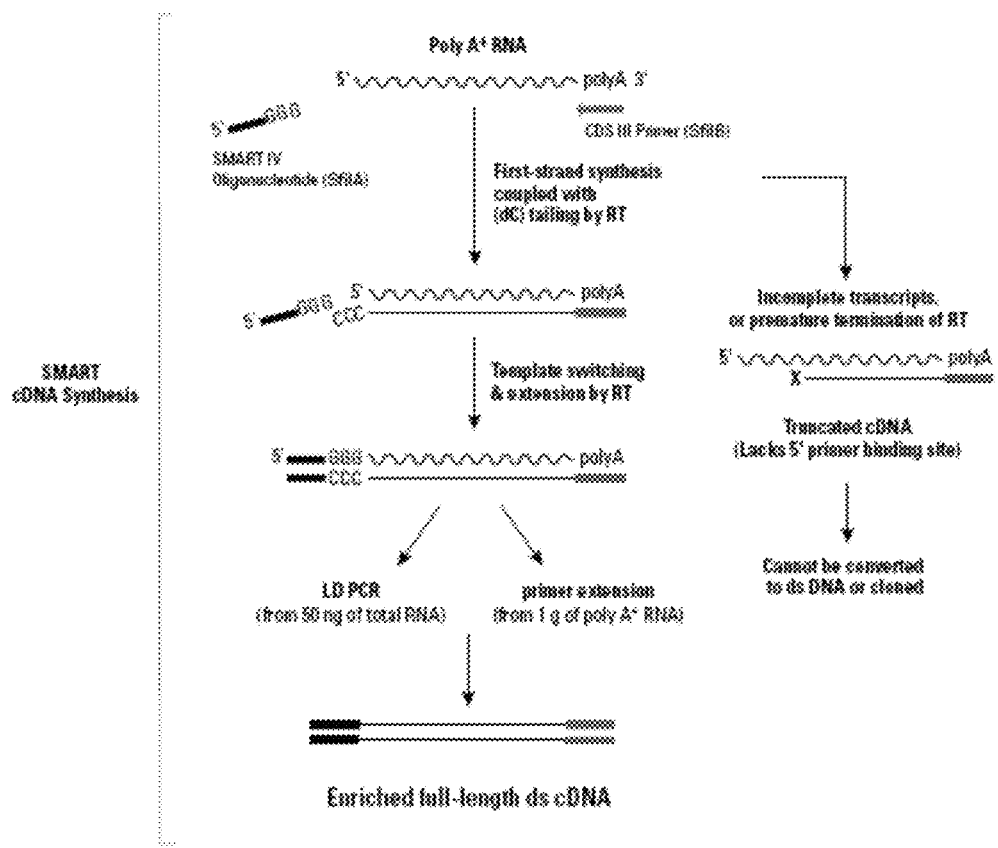
FIG. 11 shows a flow diagram of the cDNA construction used for de novo sequencing.

The attempt to carry out a PCR with just one primer (the definite forward and reverse primers each) did not yield any PCR product. There had to be a combination of both forward and reverse primers in a PCR. In order the design another set of forward and reverse primers, the construction of the cDNA was revisited. The SMART™ cDNA library construction kit was used to get the cDNA from the mRNA of *Trametes hirsuta*. Initially, the CDS III primer was used for the first cDNA strand synthesis, starting from the poly A$^+$ tail of the mRNA. For the second strand synthesis, the SMART IV oligonucleotide was used. Thus, every cDNA fragment will contain the sequence of CDSIII primer at the 3' end and the sequence of SMART IV primer at the 5' end (see FIG. 11). Hence a forward primer based on the sequence of SMART IV oligonucleotide and a reverse primer based on CDS III primer were designed to both have melting point similar to that of the definite forward and reverse primers previously designed. A flowchart of the cDNA construction from the user manual of the kit is given in FIG. 11. The new primers were designed on this basis. The two forward and reverse primers designed are given below:

```
PW1-Fwd
                                            (SEQ ID NO: 26)
TGTGGATCATTGGTGATGTCTTCCTGC

PW1-Rev
                                            (SEQ ID NO: 27)
GTCTCCGAGTTTGATCGATTCCAGC

SMART-IV
                                            (SEQ ID NO: 28)
GTATCAACGCAGAGTGGCCATTACG

CDS III
                                            (SEQ ID NO: 29)
CGAGGCGGCCGACATGTTTTTTTT
```

1.2.3.2.2 PCR Primer Walking 1

PCR using the different combinations of forward and reverse primers were carried out. The main change made in the PCR program was that of the annealing temperature. Since all the primers had similar melting temperatures, two different temperatures were tested. The different primer combinations are given in Table 5. The different reaction ingredients are summarized in Table 6. The PCR reaction program is given in Table 7.

TABLE 5

Different primer combinations and sample numbering

| Sample No. | Primer combination |
|---|---|
| 1 | Pw1-Fwd and SMART IV fwd |
| 2 | Pw1-fwd and CDS III rev |
| 3 | Pw1-rev and SMART IV fwd |
| 4 | Pw1-rev and CDS III rev |

TABLE 6

Reaction ingredients for PCR using the different combinations of primers for primer walking 1

| | Primer combinations (1-4) | |
|---|---|---|
| Contents | a (59.3° C.) (μL) | b (63.4° C.) (μL) |
| Buffer (5X HF) | 10 | 10 |
| dNTP's (10 mM) | 1 | 1 |
| Forward primer (1/10 diluted) | 1 | 1 |
| Reverse primer (1/10 diluted) | 1 | 1 |
| cDNA (180.5 ng/μL) | 1 | 1 |
| Sterile water | 35.5 | 35.5 |
| DNA polymerase (Phusion) | 0.5 | 0.5 |

TABLE 7

PCR program used to assay different temperatures for primer walking 1

| Step | Temperature (° C.) | Duration | Number of cycles |
|---|---|---|---|
| Initial denaturation | 98 | 2 min | 1 |
| Denaturation | 98 | 30 s | 40 |
| Annealing | T = 60 Gradient = 4° C. Rate = 3° C./s | 45 s | |
| Extension | 72 | 45 s | |
| Final extension | 72 | 7 min | 1 |

Figure 12:
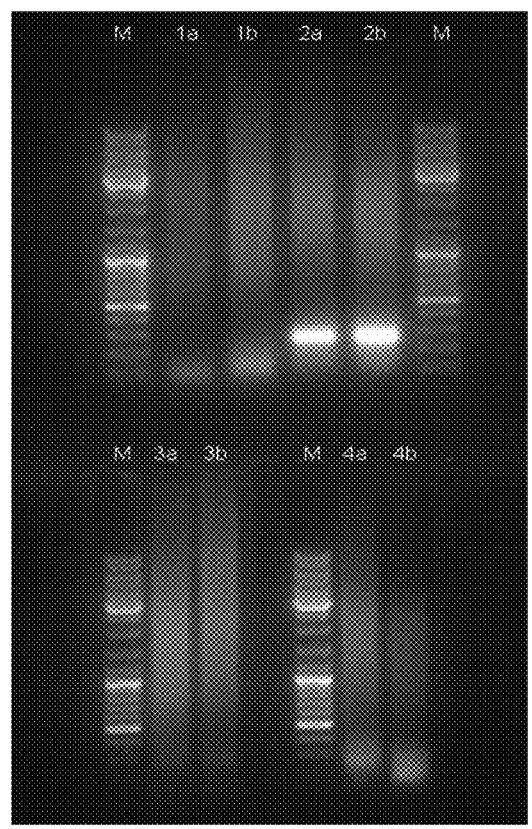
FIG. 12 shows an electropherogram of the PCR products of primer walking 1.
Figure 13:
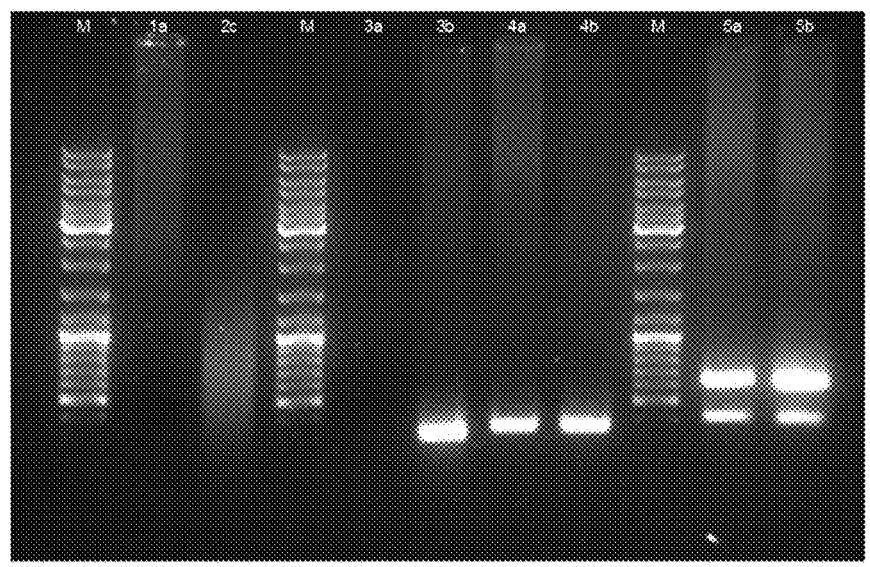
FIG. 13 shows an electropherogram of the PCR products of primer walking 2.

After carrying out the PCR, the samples (50 μL each) were analyzed preparatively on agarose gel (1% agarose). Clear bands were visible (around 300 bp) for combination no. 2 for both the tested temperatures. Faint bands were also visible (around 300 bp) for combination no. 3 for both temperatures. Combinations 2 and 3 were the sensible combinations as they each contained one forward and one reverse primer. Some other products were also obtained, but the sizes were low and hence they were not excised. The agarose gel picture is shown in FIG. 12. Thus, in primer walking 1, PCR products were obtained for products 2a, 2b, 3a and 3b. Extraction and amplification of the PCR products 2a, 2b, 3a and 3b were done in a similar manner as explained in segment 1.2.3.2.3.

1.2.3.2.3 Sequence Analysis for Primer Walking 1

Out of all the samples given for sequencing, clear results could be obtained for one of the samples of 2a insert and two samples of 3b insert. Since sequencing can be in both forward and reverse directions, the sequences were checked for the actual primer sequence and also the reverse complement sequence of the primers.

```
PW1-Fwd
                                            (SEQ ID NO: 26)
TGTGGATCATTGGTGATGTCTTCCTGC

CDS III
                                            (SEQ ID NO: 29)
CGAGGCGGCCGACATGTTTTTTTT

PW1-Rev
                                            (SEQ ID NO: 27)
GTCTCCGAGTTTGATCGATTCCAGC

SMART-IV
                                            (SEQ ID NO: 28)
GTATCAACGCAGAGTGGCCATTACG

PW1-Fwd rev
                                            (SEQ ID NO: 30)
GCAGGAAGACATCACCAATGATCCACA CDS III rev
                                            (SEQ ID NO: 31)
AAAAAAAACATGTCGGCCGCCTCG PW1-Rev rev
                                            (SEQ ID NO: 32)
GCTGGAATCGATCAAACTCGGAGAC SMART-IV rev
                                            (SEQ ID NO: 33)
CGTAATGGCCACTCTGCGTTGATAC >PW-1-2a3.pJET1.2-F
                                            (SEQ ID NO: 34)
TGTGGATCATTGGTGATGTCTTCCTGC GCAAGTACTACACTGTGTAC
GACCATGGTCGCGATGCCGTTGGCTTCGCTCTTGCCAAGTGAAGGCGT
```

-continued

```
AGTGTATCTCCCGAAGACAGTTCTACCGTACGACGCGTCGTGTTACGG

TTTCTTGATACCTGCATGTACAATACTTAGTCTCCGTTGGAACCATAC

CTTCTGTGTGTTGCCCAAAAAAAAAAAAAAAAA AAAAAAAACATGT

CGGCCGCCTCG ATCTTTCTAAAAAATCTCCTACAATATTCTCAGCTG

CCATGGAAAATCGATGTTCTTCTTTTATTCTCTCAAGATTTTCAGGCT

GTATATTAAAACTTATATTAAAAACTATGCTAACCACCTCATCAGGAA

CCGTTGTAGGTGGCGTGGGTTTTCTTGGCAATCGACTCTCATGAAAAC

TACGAGCTAAATATTCAATATGTTCCTCTTGACCAACTTTATTCTGCA

TTTTTTTTGAACGAGGTTTAGAGCAAGCTTCAGGAAACTGAGACAGGA

ATTTTATTAAAAATTTAAATTTTGAAGAAAGTTCAGGGTTAATAGCAT

CCATTTTTTGCTTTGCAAGTTCCTCAGCATTCTTAACAAAAGACGTCT

CTTTTGACATGTTTAAAGTTTAAACCTCCTGTGTGAAATTATTATCCG

CTCATAATTCCACACATTATACGAGCCGGAAGCATAAAGTGTAAAGCC

TGGGGTGCCTAATGAGTGAGCTAACTCACATTAATTGCGTTGCGCTCA

CTGCCAATTGCTTTCCAGTCGGGAAACCTGTCGTGCCAGCTGCATTAA

TGAATCGGCCAACGCGCGGGGAGAGGCGGTT
```

Translation of Insert 2a3
>EMBOSS_001_3
(SEQ ID NO: 35)
WIIGDV FLR KYYTVYDH GRDAVGFALAK*RRSVSPEDSSTVRRVV

LRFLDTCMYNT*SPLEPYLLCVAQKKKKKKKKHVGRLX

>PW-1-3b2.pJET1.2-F
(SEQ ID NO: 36)
```
GTCTCCGAGTTTGATCGATTCCAGC GGGACATGGGACAGTCAATTA

GGCTACGCGGATGTACTGCGCAGCAAGGCATGCCGACCGGCCTTCATC

ATGTTATAGCTATAGCTAGAGCAGCGCGAGAGACCCTGTAGAGTCACT

GATGAATCACTCGTGCTCCCTTCTGTGCCTTGGCTGAATAAGTTTTCC

ACAAGTTGTCGTGGAGAGTCGTGCAGGAGGGAGGCAACTTGCCCCCGG

C CGTAATGGCCACTCTGCGTTGATAC ATCTTTCTAGAAGATCTCCT

ACAATATTCTCAGCTGCCATGGAAAATCGATGTTCTTCTTTTATTCTC

TCAAGATTTTCAGGCTGTATATTAAAACTTATATTAAGAACTATGCTA

ACCACCTCATCAGGAACCGTTGTAGGTGGCGTGGGTTTTCTTGGCAAT

CGACTCTCATGAAAACTACGAGCTAAATATTCAATATGTTCCTCTTGA

CCAACTTTATTCTGCATTTTTTTGAACGAGGTTTAGAGCAAGCTTCA

GGAAACTGAGACAGGAATTTTATTAAAAATTTAAATTTTGAAGAAAGT

TCAGGGTTAATAGCATCCATTTTTTGCTTTGCAAGTTCCTCAGCATTC

TTAACAAAAGACGTCTCTTTTGACATGTTTAAAGTTTAAACCTCCTGT

GTGAAATTATTATCCGCTCATAATTCCACACATTATACGAGCCGGAAG

CATAAAGTGTAAAGCCTGGGGTGCCTAATGAGTGAGCTAACTCACATT

AATTGCGTTGCGCTCACTGCCAATTGCTTTCCAGTCGGGAAACCTGTC

GTGCCAGCTGCATTAATGAATCGGCCAACGCGCGG
```

Translation of Insert 3b1
(SEQ ID NO: 37)
YQRRVA ITAGGKLPPSCTTLHDNLWKTYSAKAQKGARVIHQ*LYRVS

RAALAIAIT**RPVGMPCCAVHPRSLIDCPHVP LESIKLGD

Analysis of the sequences showed that the insert 2a had both the PW-I fwd primer sequence and the original degenerate reverse primer sequence. Hence it is part of the protein of interest. The translation of the sequence gave a sequence with a stop codon in between. Hence the end of the protein of interest has been reached. In the case of the sequence of the insert 3b, the PW-I reverse primer was present but did not comprise the initial degenerate forward primer sequence. Hence it was quite clear that the designed reverse primer PW-1 rev was not specific enough and had bound to some other part of the cDNA. Thus, three other reverse primers were designed, which were used for primer walking 2. A total of 84 amino acid residues could be deduced at the end of primer walking 1 and the end of the protein had been reached. The sequence of the peptide obtained until this step is given below:

(SEQ ID NO: 38)
KAYWEVE LESIKLGD DELELDNTGAAIDTGTSLIALPSDLA

EMLNVQIGAKKSWNGQYTVDCAKVPTLPDLTFYFSGKPYTLKG

TDYVLEVQGTCMSSFTGIDINLPGGGAL WIIGDV FLR KYY

TVYDH GRDAVGFALAK

1.2.3.3 Primer Walking 2

1.2.3.3.1 Design of Alternative Reverse Primers

Since the reverse primer (PW-1 rev) from primer walking 1 was not specific enough for the PCR, alternative reverse primers had to be designed. Three alternative reverse primers were designed. Further it was also noticed (based on the BLAST search) that the reverse primers were situated at the end of the entire protein sequence. As a consequence, the degenerate primer (Fwd-1) from the first step (expected to be in the middle of the sequence in the BLAST search) was used as the forward primer.

>6a1-forward.pJET1.2-F (result of 2.1)
(SEQ ID NO: 24)
```
TTTTTCAGCAAGAT AAGGCTTATTGGGAGGTGGA GCTGGA

ATCGATCAAACT CGGAGACGACGAGCTTGAGCT CGATAAC

A CCGGCGCTGCCATCGACACT GGAACCTCGTTGATTGCTC

TCCCCTCCGATCT GGCGGAGATGCTCAATGTGCAAATC GG

TGCCAAGAAGTCCTGGAATGGTCAGTACACCGTCGACTGCGC

GAAGGTCCCTACCCTCCCCGACCTCACCTTCTACTTCAGCGG

CAAGCCTTACACTCTCAAGGGTACCGACTACGTCCTCGAAGT

TCAGGGAACTTGCATGTCCTCGTTCACCGGCATCGACATCAA

TCTGCCCGGCGGTGGTGCTC TGTGGATCATTGGTGATGTCT

TCCTGC GCA AGTACTACACAGTTTACGATCACG ATCTTT

CTAGAAGATCTCCTACAATATTCTCAGCTGCCATGGAAAATC
```

-continued

```
GATGTTCTTCTTTTATTCTCTCAAGATTTTCAGGCTGTATAT

TAAAACTTATATTAAGAACTATGCTAACCACCTCATCAGGAA

CCGTTGTAGGTGGCGTGGGTTTTCTTGGCAATCGACTCTCAT

GAAAACTACGAGCTAAATATTCAATATGTTCCTCTTGACCAA

CTTTATTCTGCATTTTTTTGAACGAGGTTTAGAGCAAGCTT

CAGGAAACTGAGACAGGAATTTTATTAAAAATTTAAATTTTG

AAGAAAGTTCAGGGTTAATAGCATCCATTTTTTGCTTTGCAA

GTTCCTCAGCATTCTTAACAAAAGACGTCTCTTTTGACATGT

TTAAAGTTTAAACCTCCTGTGTGAAATTATTATCCGCTCATA

ATTCCACACATTATACGAGCCGGAAGCATAAAGTGTAAAGCC

TGGGGTGCCTAATGAGTGAGCTAACTCACATTAATTGCGTTG

CGCTCACTGCCAATTGCTTTCCAGTCGGGAACCTGTCGTGCC

AGCTGCATTAATG
```

The reverse complements of the sequences marked in the above:

```
1) PW-2 rev Pri-1:
                                      (SEQ ID NO: 39)
AGCTCAAGCTCGTCGTCTCCG 2) PW-2 rev Pri-2:
                                      (SEQ ID NO: 40)
AGTGTCGATGGCAGCGCCG 3) PW-2 rev Pri-3:
                                      (SEQ ID NO: 41)
GATTTGCACATTGAGCATCTCCGCC
```

1.2.3.3.2 PCR Primer Walking 2

PCR using the combinations of the three new reverse primers designed with the forward degenerated primer (Fwd-1) was attempted. As a test, one of the reverse primers were also tested with the primer which binds to the end of the cDNA (SMART IV fwd) to check if any clear bands could be obtained (owing to the long distance to the beginning of the protein). As a recheck, the combination of degenerate forward primer (Fwd-1) and degenerate reverse primer (Rev-2) from step 1 was also repeated. The different combinations of primers used are given in Table 8. The PCR components are summarized in Table 9, and the PCR program used is indicated in Table 10.

TABLE 8

Numbering of the different primer combinations tested for PW-2

| Sample no. | Primer combination |
|---|---|
| 1 | degenerate Fwd-1 and degenerate Rev-1 |
| 2 | SMART IV Fwd and PW-2-Rev-Pri-2 |
| 3 | degenerate Fwd-1 and PW-2-Rev-Pri-1 |
| 4 | degenerate Fwd-1 and PW-2-Rev-Pri-2 |
| 5 | degenerate Fwd-1 and PW-2-Rev-Pri-3 |

TABLE 9

Reaction components for PCR using the different combinations of primers for primer walking 2

| | Primer combinations (1-5) | | |
|---|---|---|---|
| Contents | a (53.2° C.) (µL) | b (56.5° C.) (µL) | c (59.4° C.) (µL) |
| Buffer (5X HF) | 10 | 10 | 10 |
| dNTPs (10 mM) | 1 | 1 | 1 |
| Forward primer (1/10 diluted) | 1 | 1 | 1 |
| Reverse primer (1/10 diluted) | 1 | 1 | 1 |
| cDNA (180.5 ng/µL) | 1 | 1 | 1 |
| Sterile water | 35.5 | 35.5 | 35.5 |
| DNA polymerase (Phusion) | 0.5 | 0.5 | 0.5 |

TABLE 10

PCR program used for checking different temperatures for primer walking 2

| Step | Temperature (° C.) | Time | Number of cycles |
|---|---|---|---|
| Initial denaturation | 98 | 2 min | 1 |
| Denaturation | 98 | 30 s | 40 |
| Annealing | T = 55 Gradient = 4° C. Rate = 3° C./s | 45 s | |
| Extension | 72 | 1 min | |
| Final extension | 72 | 7 min | 1 |

After carrying out the PCR, the samples (50 µL each) were analyzed preparatively on agarose gel (1% agarose). Clear bands (PCR product) were visible (around 400 bp) for samples 3b, 4a, 4b, 5a and 5b. Additionally, distinct bands were visible (around 600 bp) for combinations 5a and 5b. However, no distinct bands were observed in combination no. 2. It is possible that the distance between the 5' end of the cDNA and the reverse primer was too long. It is also possible that the duration of the DNA strand extension step was too short for the long distance extension to reach completion.

The extraction and amplification of the PCR products 3b, 4a, 4b, 5a small band, 5b small band, 5a big band and 5b big band were performed in a manner similar to that explained in segment 1.2.3.1.2. Unfortunately, the transformation plates of 3b, 4a and 5a big band were contaminated. As a result, only the samples 4b, 5a small band, 5b small band and 5b big band were sequenced.

1.2.3.3.3 Sequence Analysis for Primer Walking 2

The DNA sequences obtained were analyzed for identifying the primers and hence the sequence of the inserts. All the inserts resulted in the same sequence. The identities of the sequences obtained were compared. The sequences were found to be completely identical.

Key:

```
PW-2-Reverse primers
1) PW-2 rev Pri-1:
                                      (SEQ ID NO: 39)
AGCTCAAGCTCGTCGTCTCCG 2) PW-2 rev Pri-2:
                                      (SEQ ID NO: 40)
AGTGTCGATGGCAGCGCCG
```

3) PW-2 rev Pri-3:
(SEQ ID NO: 41)
GATTTGCACATTGAGCATCTCCGCC

Reverse complement of reverse primers:
2) PW-2 rev Pri-2:
(SEQ ID NO: 42)
CGGCGCTGCCATCGACACT 3) PW-2 rev Pri-3:
(SEQ ID NO: 43)
GGCGGAGATGCTCAATGTGCAAATC Fwd-1 degenerated primer
(SEQ ID NO: 14)
AAYCARGAYTTYGCNGARGC >4b1.pJET1.2-F
(SEQ ID NO: 44)
<u>AACCAGGATTTTGCGGAGGC</u> CACCAAGGAGCCCGGCCTCGCATTT
GCCTTTGGCAAGTTTGATGGTATCCTCGGCCTCGGGTATGACACCA
TTTCCGTGAACCACATCACTCCTCCCTTCTACCAGATGATGAACCA
GAAGCTCGTCGATTCTCCTGTGTTCTCTTTCCGCCTCGGTAGCTCG
GAAGAGGACGGTGGTGAAGCCATCTTCGGAGGAGTCGATGAGACCG
CGTACAGTGGCAAGATCGAATACGTCCCTGTCAGGAGGAAGGCGTA
CTGGGAGGTGGAGCTGGAATCGATCAAACTCGGAGACGACGAGCTT
GAGCTCGATAACAC <u>CGGCGCTGCCATCGACACT</u> ATCTTTCTAGA
AGATCTCCTACAATATTCTCAGCTGCCATGGAAAATCGATGTTCTT
CTTTTATTCTCTCAAGATTTTCAGGCTGTATATTAAAACTTATATT
AAGAACTATGCTAACCACCTCATCAGGAACCGTTGTAGGTGGCGTG
GGTTTTCTTGGCAATCGACTCTCATGAAAACTACGAGCTAAATATT
CAATATGTTCCTCTTGACCAACTTTATTCTGCATTTTTTTGAACG
AGGTTTAGAGCAAGCTTCAGGAAACTGAGACAGGAATTTTATTAAA
AATTTAAATTTTGAAGAAAGTTCAGGGTTAATAGCATCCATTTTTT
GCTTTGCAAGTTCCTCAGCATTCTTAACAAAAGACGTCTCTTTTGA
CATGTTTAAAGTTTAAACCTCCTGTGTGAAATTATTATCCGCTCAT
AATTCCACACATTATACGAGCCGGAAGCATAAAGTGTAAAGCCTGG
GGTGCCTAATGAGTGAGCTAACTCACATTAATTGCGTTGCGCTCAC
TGCCAATTGCTTTCCAGTCGGGAAACCTGTCGTG >Translation of insert 4b1
(SEQ ID NO: 45)
<u>NQDFAEA</u> TKEPGLAFAFGKFDGILGLYDTISVNHITPPFYQMMN
QKLVDSPVFSFRLGSSEEDGGEAIFGGVDETAYSGKIEYVPVRR <u>K</u>
<u>AYWEVE</u> LESIKLGDDELELDNT <u>GAAIDT</u>

>5a1smallband.pJET1.2-F
(SEQ ID NO: 46)
<u>GATTTGCACATTGAGCATCTCCGCC</u> AGATCGGAGGGGAGAGCAAT
CAACGAGGTTCC <u>AGTGTCGATGGCAGCGCCG</u> GTGTTATCGAGCT
CAAGCTCGTCGTCTCCGAGTTTGATCGATTCCAGCTCCACCTCCCA
GTACGCCTTCCTCCTGACAGGGACGTATTCGATCTTGCCACTGTAC
GCGGTCTCATCGACTCCTCCGAAGATGGCTTCACCACCGTCCTCTT
CCGAGCTACCGAGGCGGAAAGAGAACACAGGAGAATCGACGAGCTT
CTGGTTCATCATCTGGTAGAAGGGAGGAGTGATGTGGTTCACGGAA
ATGGTGTCATACCCGAGGCCGAGGATACCATCAAACTTGCCAAAGG
CAAATGCGAGGCCGGGCTCCTTGGTG <u>GCCTCAGCAAAATCCTGAT</u>
<u>T</u> ATCTTTCTAGAAGATCTCCTACAATATTCTCAGCTGCCATGGAA
AATCGATGTTCTTCTTTTATTCTCTCAAGATTTTCAGGCTGTATAT
TAAAACTTATATTAAGAACTATGCTAACCACCTCATCAGGAACCGT
TGTAGGTGGCGTGGGTTTTCTTGGCAATCGACTCTCATGAAAACTA
CGAGCTAAATATTCAATATGTTCCTCTTGACCAACTTTATTCTGCA
TTTTTTTTGAACGAGGTTTAGAGCAAGCTTCAGGAAACTGAGACAG
GAATTTTATTAAAAATTTAAATTTTGAAGAAAGTTCAGGGTTAATA
GCATCCATTTTTTGCTTTGCAAGTTCCTCAGCATTCTTAACAAAAG
ACGTCTCTTTTGACATGTTTAAAGTTTAAACCTCCTGTGTGAAATT
ATTATCCGCTCATAATTCCACACATTATACGAGCCGGAAGCATAAA
GTGTAAAGCCTGGGGTGCCTAATGAGTGAGCTAACTCACATT >Translation of insert 5a1 small band
(SEQ ID NO: 47)
<u>NQDFAEA</u> TKEPGLAFAFGKFDGILGLYDTISVNHITPPFYQMMN
QKLVDSPVFSFRLGSSEEDGGEAIFGGVDETAYSGKIEYVPVRR <u>K</u>
<u>AYWEVE</u> LESIKLGDDELELDNT <u>GAAIDT</u> GTSLIALPSDL <u>AEM</u>
<u>LNVQI</u>

>5b2bigband.pJET1.2-F
(SEQ ID NO: 48)
<u>GATTTGCACATTGAGCATCTCCGCC</u> AGATCGGAGGGGAGAGCAAT
CAACGAGGTTCC <u>AGTGTCGATGGCAGCGCCG</u> GTGTTATCGAGCT
CAAGCTCGTCGTCTCCGAGTTTGATCGACTCCAGCTCCACCTCCCA
GTACGCCTTCCTCCTGACAGGGACGTATTCGATCTTGCCACTGTAC
GCGGTCTCATCGACTCCTCCGAAGATGGCTTCACCACCGTCCTCTT
CCGAGCTACCGAGGCGGAAAGAGAACACAGGAGAATCGACGAGCTT
CTGGTTCATCATCTGGTAGAAGGGAGGAGTGATGTGGTTCACGGAA
ATGGTGTCATAACCCAGGCCGAGGATACCATCGAACTT <u>GCCAAAG</u>
<u>GCAAATGCGAG</u> GCCGGGCTCCTTGGTG <u>GCCTCAGCGAAGTCCTG</u>
<u>ATA</u> TCTTTCTAGAAGATCTCCTACAATATTCTCAGCTGCCATGGA
AAATCGATGTTCTTCTTTTATTCTCTCAAGATTTTCAGGCTGTATA
TTAAAACTTATATTAAGAACTATGCTAACCACCTCATCAGGAACCG
TTGTAGGTGGCGTGGGTTTTCTTGGCAATCGACTCTCATGAAAACT
ACGAGCTAAATATTCAATATGTTCCTCTTGACCAACTTTATTCTGC
ATTTTTTTGAACGAGGTTTAGAGCAAGCTTCAGGAAACTGAGACA
GGAATTTTATTAAAAATTTAAATTTGAAGAAAGTTCAGGGTTAAT
AGCATCCATTTTTTGCTTTGCAAGTTCCTCAGCATTCTTAACAAAA
GACGTCTCTTTTGACATGTTTAAAGTTTAAACCTCCTGTGTGAAAT -continued

```
TATTATCCGCTCATAATTCCACACATTATACGAGCCGGAAGCATAA

AGTGTAAAGCCTGGGGTGCCTAATGAGTGAGCTAACT

>Translation of insert 5b2 bigband
                                       (SEQ ID NO: 49)
YQDFAEA TKEPGLAFAFGKFDGILGLGYDTISVNHITPPFYQMMN

QKLVDSPVFSFRLGSSEEDGGEAIFGGVDETAYSGKIEYVPVRR K

AYWEVE LESIKLGDDELELDNT GAAIDTGT SLIALPSDL AEM

LNVQI

Protein sequence after primer walking step 1:
>EMBOSS_001_3
                                       (SEQ ID NO: 38)
KAYWEVE LESIKLGD DELELDNT GAAIDT GTSLIALPSDL A

EMLNVQI GAKKSWNGQYTVDCAKVPTLPDLTFYFSGKPYTLKGTD

YVLEVQGTCMSSFTGIDINLPGGGAL WIIGDV FLR KYYTVYDH

GRDAVGFALAK*

Protein sequence from primer walking step 2:
                                       (SEQ ID NO: 50)
NQDFAEA TKEPGLAFAFGKFDGILGLGYDTISVNHITPPFYQMMN

QKLVDSPVFSFRLGSSEEDGGEAIFGGVDETAYSGKIEYVPVRR K

AYWEVE LESIKLGDDELELDNT GAAIDT GTSLIALPSDLAEML

NVQI GAKKSWNGQYTVDCAKVPTLPDLTFYFSGKPYTLKGTDYVL

EVQGTCMSSFTGIDINLPGGGAL WIIGDV FLR KYYTVYDH GR

DAVGFALAK*
```

Primer walking 2 using the newly designed reverse primers and the degenerate forward primers was successful. The sequence could be easily verified as it comprised several primer sequences which had been previously designed. Additional 89 amino acid residues were determined from primer walking 2. After primer walking 2, 173 amino acid residues of the protein were determined and half the stretch of the protein was achieved (based on BLAST similarity search). The protein sequence after primer walking 2 is given below (SEQ ID NO: 50):

```
NQDFAEA TKEPGLAFAFGKFDGILGLGYDTISVNHITPPFYQ

MMNQKLVDSPVFSFRLGSSEEDGGEAI FGGVDETAYSGKIEY

VPVRR KAYWEVE LESIKLGDDELELDNT GAAIDT GTSLI

ALPSDL AEMLNVQI GAKKSWNGQYTVDCAKVPTLPDLTFYF

SGKPYTLKGTDYVLEVQGTCMSSFTGIDINLPGGGAL WIIGD

V FLR KYYTVYDH GRDAVGFALAK*
```

1.2.3.4 Primer Walking 3

1.2.3.4.1 Design of Primers for Primer Walking 3

The first two primer walking steps were successful. The situation in the next step was a little more complicated, as there was a possibility that the 5' end of the cDNA was still too far away for PCR. Hence, as a second option, degenerated forward primers were designed in addition to the definite reverse primer. For the design of the degenerated primers, the top ten complete consensus full sequence hits related to the obtained sequence were compared and primers were designed from the best conserved regions of these sequences, which were upstream to the position to be resolved. In case of PW-3 degenerated forward primers 1 and 3, the degree of degeneracy was very high. In order to reduce degeneracy, the base deoxyinosine (which binds to A, T, G and C) was used in the synthesis. The PW-3 degenerated forward primer 2 has the lowest amount of degeneracy and is the most promising candidate among the designed degenerated primers. Additionally, two reverse primers were designed from the DNA sequence of the currently obtained sequence. A comparison of these sequences and the conserved regions selected for primer design is shown below. Definite reverse primers were also designed. Shorter versions of the reverse1 and reverse2 primers were also designed, in case the temperatures of annealing of the degenerate forward primers would be low. Additionally, a third reverse primer was designed, which comprised a segment of each of primers reverse 1 and reverse 2.

```
PW-3-Degenerate Fwd Primer 1:
                                       (SEQ ID NO: 51)
    CAN ARR HTIAARYTISANAA (SEQ ID NO: 59)
    -HRMKLEK PW-3-Degenerate Fwd Primer 2:
                                       (SEQ ID NO: 52)
    AAYTWYATGAAYGCNCARTA (SEQ ID NO: 60)
    -NYMNAQY PW-3-Degenerate Fwd Primer 3:
                                       (SEQ ID NO: 53)
    TTYAARGTIRTNYTTIGAYAC (SEQ ID NO: 61)
    -FKVILDT PW-3-definite Reverse Primer1:
                                       (SEQ ID NO: 54)
    GCCAAAGGCAAATGCGAG (SEQ ID NO: 62)
    -LAFAFG
    (rev. complement)

Pw3-RevPrimer1short:
                                       (SEQ ID NO: 55)
    GCCAAAGGCAAATGCG PW-3-definite Reverse Primer2:
                                       (SEQ ID NO: 56)
    CAGGCCGAGGATACCATC (SEQ ID NO: 63)
    -DGILGL
    (rev. complement)

Pw3-RevPrimer2short:
                                       (SEQ ID NO: 57)
    CAGGCCGAGGATACC Pw3-RevPrimer23x:
                                       (SEQ ID NO: 58)
    CATCGAACTTGCCAAAG (SEQ ID NO: 64)
    -FGKFDX
```

The ClutaW sequence alignment results of the top pBLAST best ten hits are shown in FIGS. 14a and 14b. The conserved sequences used for designing the degenerate forward primers for primer walking 3 and the relative positioning of the definite reverse primers are marked.

1.2.3.4.2 Optimization of Temperature and Buffer Conditions

The reaction buffer and the temperature of primer annealing had to be optimized for the PCR since degenerate forward primers were used. Different combination of forward and reverse primers were carried out. For optimizing the conditions, a degenerate forward 2 primer was used in combination with the short reverse primers. The nomenclature used for the different primer combinations/annealing temperature and buffer usage are given below. The components of the different PCR reactions carried out are summarized in the Table.
Numbering of Primer Combinations
Primer combination-I: PW-3-degenerate Fwd-2 and PW-3-Rev1_short(a)
Primer combination-II: PW-3-degenerate Fwd-2 and PW-3-Rev2_short(a)
Primer combination-III: SMART IV Fwd and PW-3-Rev2 (b)
PCR with primer combination III was performed such that it could be used as a template for nested primer PCR in the next step.
Temperature of Annealing
a—45.4° C.
b—59.8° C.
Buffer Usage
1-5×HF buffer
2-5×GC buffer
3-5×HF buffer+DMSO

TABLE 11

Reaction components for PCR using the different combinations of primers for primer walking 3

| Contents | I (45.4° C.) (µL) | | | II (45.4° C.) (µL) | | | III (59.8° C.) (µL) |
|---|---|---|---|---|---|---|---|
|  | 1 | 2 | 3 | 1 | 2 | 3 | 1 |
| Buffer (5X HF) | 10 | 10 | 10 | 10 | 10 | 10 | 10 |
| dNTP's (10 mM) | 1 | 1 | 1 | 1 | 1 | 1 | 1 |
| Forward primer (undiluted/ 1/10 dil.) | 1 | 1 | 1 | 1 | 1 | 1 | 1 |
| Reverse primer (1/10 diluted) | 1 | 1 | 1 | 1 | 1 | 1 | 1 |
| cDNA (350 ng/µL) | 0.5 | 0.5 | 0.5 | 0.5 | 0.5 | 0.5 | 0.5 |
| DMSO | — | — | 1.5 | — | — | 1.5 | — |
| Sterile water | 36 | 36 | 34.5 | 36 | 36 | 34.5 | 36 |
| DNA polymerase (Phusion) | 0.5 | 0.5 | 0.5 | 0.5 | 0.5 | 0.5 | 0.5 |

TABLE 12

PCR program used for the buffer and annealing temperature optimization in primer walking-III

| Step | Temperature (° C.) | Time | Number of cycles |
|---|---|---|---|
| Initial denaturation | 98 | 2 min | 1 |
| Denaturation | 98 | 30 s | 35 |
| Annealing | T = 50 Gradient = 10° C. Rate = 3° C./s | 45 s | |
| Extension | 72 | 1 min | |
| Final extension | 72 | 7 min | 1 |

Figure 15:
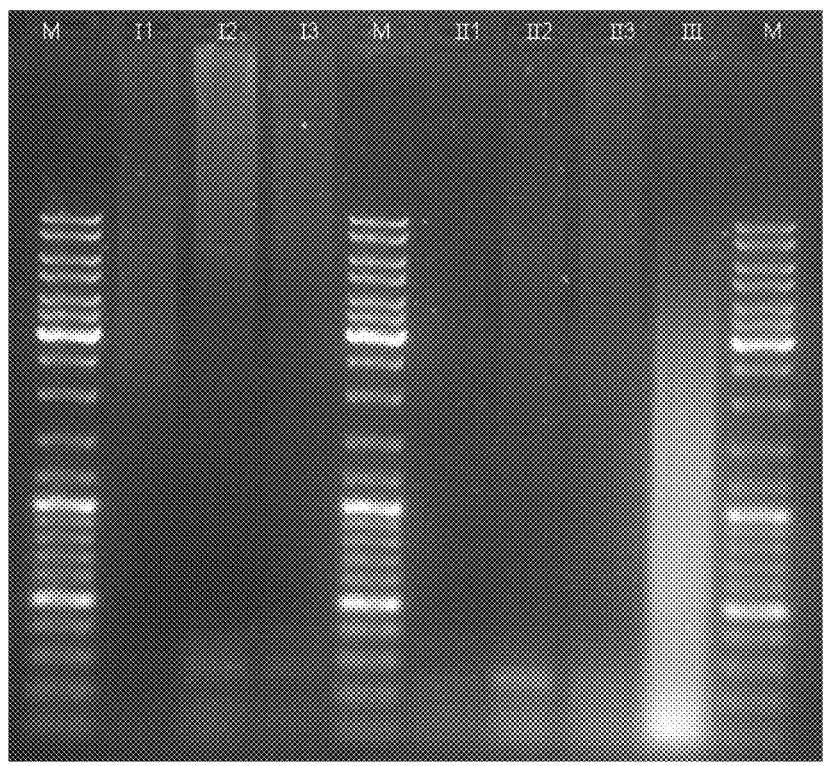
FIG. 15 shows an electropherogram of the products of optimized PCR reactions of primer walking 3.

FIG. 15 is an electropherogram of the PCR reactions on 1% agarose gel optimized concerning buffers and annealing temperatures. The samples (30 µL) were each analyzed on agarose gel. The PCR product III was used as template DNA for further nested PCR reactions. Since a PCR product was observed when GC buffer was used but not observed when only HF buffer was used for primer combinations I and II, GC buffer was taken as the preferred buffer for the nested PCR. The temperature of annealing was chosen to be 45.4° C. for the nested primer PCR, as product formation could be observed at this temperature.

1.2.3.4.3 Nested Primer PCR

The product III from the PCR reaction on the previous day was used as template DNA for the nested PCR. All primer combinations suspected to be lying within the template were tested. In addition, the best suited reaction buffer for nested primer PCR was also tested for the combination of degenerate PW-3-forward-2 primer (primer with least degree of degeneracy) and PW-3-reverse1-short primer. The nomenclature for the primer combinations and the buffer that were used is given below. The PCR reaction components are summarized in Table 13.
Primer Combinations/Template DNA
I—Pw3-Fw Primer 1 and Pw3-RevPrimer1short/PCR product III from previous step
II—Pw3-FwPrimer2 and Pw3-RevPrimer1short/PCR product III from previous step
III—Pw3-FwPrimer3 and Pw3-RevPrimer1short/PCR product III from previous step
IV—Pw3-FwPrimer3 and Pw3-RevPrimer1short/PCR product II 2 from previous step
V—Pw3-FwPrimer2 and Pw3-RevPrimer23x/PCR product III from previous step
PCR Reaction Buffer
1—GC buffer
2—GC buffer with DMSO
3—HF buffer
4—HF buffer with DMSO

TABLE 13

Reaction components for PCR using the different combination of primers for Primer walking-3

| Contents | Reaction components for different primer combinations (µL) (at 45.4° C. annealing temperature) | | | | | | | |
|---|---|---|---|---|---|---|---|---|
|  | I1 | II1 | III1 | II2 | II3 | II4 | IV1 | V1 |
| Buffer (5X 1 (or) 2) | 10 | 10 | 10 | 10 | 10 | 10 | 10 | 10 |
| dNTP's (10 mM) | 1 | 1 | 1 | 1 | 1 | 1 | 1 | 1 |
| Forward primer (undiluted) | 1 | 1 | 1 | 1 | 1 | 1 | 1 | 1 |
| Reverse primer (1/10 diluted) | 1 | 1 | 1 | 1 | 1 | 1 | 1 | 1 |
| Template DNA | 1 | 1 | 1 | 1 | 1 | 1 | 5 | 1 |

TABLE 13-continued

Reaction components for PCR using the different combination of primers for Primer walking-3

| Contents | Reaction components for different primer combinations (μL) (at 45.4° C. annealing temperature) | | | | | | | |
|---|---|---|---|---|---|---|---|---|
| | I1 | II1 | III1 | I2 | II3 | II4 | IV1 | V1 |
| DMSO | — | — | — | 1.5 | — | 1.5 | — | — |
| Sterile water | 36 | 36 | 36 | 34.5 | 36 | 34.5 | 32 | 36 |
| DNA polymerase (Phusion) | 0.5 | 0.5 | 0.5 | 0.5 | 0.5 | 0.5 | 0.5 | 0.5 |

Figure 16:
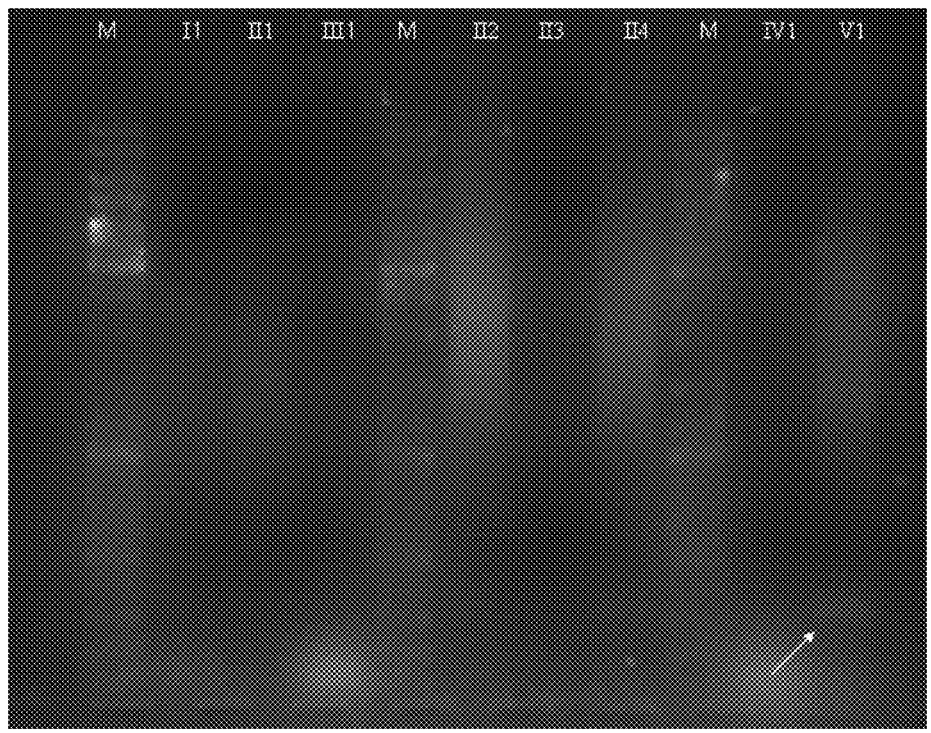
FIG. 16 shows an electropherogram of the products of nested primer PCR reactions of primer walking 3.

FIG. 16 shows an electropherogram of the nested primer PCR reaction on 1% agarose gel. The band from sample V1 was excised for extraction of DNA, amplification of the PCR product by cloning and transformation and sequence analysis.

1.2.3.4.4 Sequence Analysis for Primer Walking 3

The DNA sequences obtained were analyzed for identifying the primers and hence the sequence of the inserts. All inserts resulted in the same sequence. The identities of the sequences obtained were compared. The sequences were found to be completely identical.

```
Fw Primer 1:
                                    (SEQ ID NO: 51)
CANARRHTIAARYTISANAA (SEQ ID NO: 59)
-HRMKLEK FwPrimer2:
                                    (SEQ ID NO: 52)
AAYTWYATGAAYGCNCARTA (SEQ ID NO: 60)
-NYMNAQY FwPrimer3:
                                    (SEQ ID NO: 53)
TTYAARGTIRTNYTTIGAYAC (SEQ ID NO: 61)
-FKVILDT RevPrimer1:
                                    (SEQ ID NO: 54)
GCCAAAGGCAAATGCGAG (SEQ ID NO: 62)
-LAFAFG
(rev complement)

RevPrimer1short:
                                    (SEQ ID NO: 55)
GCCAAAGGCAAATGCG RevPrimer2:
                                    (SEQ ID NO: 56)
CAGGCCGAGGATACCATC (SEQ ID NO: 63)
-DGILGL
(rev complement)

RevPrimer2short:
                                    (SEQ ID NO: 57)
CAGGCCGAGGATACC RevPrimer23x:
                                    (SEQ ID NO: 58)
CATCGAACTTGCCAAAG (SEQ ID NO: 64)
-FGKFDX >PW-3-V2-2.pJET1.2-F
                                    (SEQ ID NO: 65)
CATCGAACTTGCCAAAG GCAAATGCG AGGCCGGGCTCCTTGGT
GGCCTCTGCGAAATCTTGGTTCTTGATGGTGATGTCACCGATTGT
CAAGACATCTTGCGAGACGAAGCCCTCCATGGAGCCAGAGCCATA
CTGGATCGAGAACTCGGAGCCGTTCGCCTTGTATGTCGACGAAGC
GGTCGAGTCATACTTGGCGTGTAGGAAGCACGCAATGGAGGTACA
CTTGGTGCTCGGAACCCAGAGGTTGCTCGACCCAGTGTCCAGGAT
GACCTTGAACGATTGCGGGGAGTGCCCAAGGTGATTTCAGCGAA
GTACTGTGCA TTCAT GAAGTTATCTTTCTAGAAGATCTCCTAC
AATATTCTCAGCTGCCATGGAAAATCGATGTTCTTCTTTTATTCT
CTCAAGATTTTCAGGCTGTATATTAAAACTTATATTAAGAACTAT
GCTAACCACCTCATCAGGAACCGTTGTAGGTGGCGTGGGTTTTCT
TGGCAATCGACTCTCATGAAAACTACGAGCTAAATATTCAATATG
TTCCTCTTGACCAACTTTATTCTGCATTTTTTTGAACGAGGTTT
AGAGCAAGCTTCAGGAAACTGAGACAGGAATTTTATTAAAAATTT
AAATTTTGAAGAAAGTTCAGGGTTAATAGCATCCATTTTTTGCTT
TGCAAGTTCCTCAGCATTCTTAACAAAAGACGTCTCTTTTGACAT
GTTTAAAGTTTAAACCTCCTGTGTGAAATTATTATCCGCTCATAA
TTCCACACATTATACGAGCCGGAAGCATAAAGTGTAAAGCCTGGG
GTGCCTAATGAGTGAGCTAACTCACATTAATTGCGTTGCGCTCAC
TGCCAATTGCTTTCCAGTCGGGAAACCTGTCGTGCCAGCTGC >EMBOSS_001_5
                                    (SEQ ID NO: 66)
NFMNAQY FAEITLGTPPQS FKVILDT GSSNLWVPSTKCTSIA
CFLHAKYDSTASSTYKANGSEFSIQYGSGSMEGFVSQDVLTIGDI
TIK NQDFAEA TKEPG LAFAFG KFDX
```

Protein Sequence after Primer Walking Step 1:

```
>EMBOSS_001_3
                                    (SEQ ID NO: 38)
KAYWEVE LESIKLGD DELELDNT GAAIDT GTSLIALPSDL
AEMLNVQI GAKKSWNGQYTVDCAKVPTLPDLTFYFSGKPYTLK
GTDYVLEVQGTCMSSFTGIDINLPGGGAL WIIGDV FLR KYY
TVYDH GRDAVGFALAK*
```

Protein Sequence from Primer Walking Step 2:

```
                                    (SEQ ID NO: 50)
NQDFAEA TKEPGLAFAFGKFDGILGLGYDTISVNHITPPFY
QMMNQKLVDSPVFSFRLGSSEEDGGEAIFGGVDETAYSGKIE
YVPVRR KAYWEVE LESIKLGDDELELDNT GAAIDT GTS
```

-continued

LIALPSDL AEMLNVQI GAKKSWNGQYTVDCAKVPTLPDLT

FYFSGKPYTLKGTDYVLEVQGTCMSSFTGIDINLPGGGAL W

IIGDV FLR KYYTVYDH GRDAVGFALAK*

Protein Sequence from Primer Walking Step 3:

(SEQ ID NO: 67)
NFMNAQY FAEITLGTPPQS FKVILDT GSSNLWVPSTKCTSIAC

FLHAKYDSTASSTYKANGSEFSIQYGSGSMEGFVSQDVLTIGDITI

K NQDFAEA TKEPG LAFAFG KFDX

Protein Sequence after Primer Walking Step 3:

(SEQ ID NO: 68)
NFMNAQY FAEITLGTPPQS FKVILDT GSSNLWVPSTKCTSIAC

FLHAKYDSTASSTYKANGSEFSIQYGSGSMEGFVSQDVLTIGDITI

K NQDFAEA TKEPG LAFAFG KFD GILGL GYDTISVNHITPP

FYQMMNQKLVDSPVFSFRLGSSEEDGGEAIFGGVDETAYSGKIEYV

PVRR KAYWEVE LESIKLGDDELELDNT GAAIDT GTSLIALPS

DL AEMLNVQI GAKKSWNGQYTVDCAKVPTLPDLTFYFSGKPYTL

KGTDYVLEVQGTCMSSFTGIDINLPGGGAL WIIGDV FLR KYYT

VYDH GRDAVGFALAK*

Primer walking 3 using the newly designed reverse primers and the degenerate forward primers was successful. The sequence could be verified, as it comprised the primer sequences previously constructed. Another 102 amino acid residues were determined by primer walking 3. After primer walking 3, 263 amino acid residues of the protein had been determined. The protein sequence after primer walking 3 is given again below in a contiguous manner:

(SEQ ID NO: 68)
NFMNAQYFAEITLGTPPQSFKVILDTGSSNLWVPSTKCTSIACFLH

AKYDSTASSTYKANGSEFSIQYGSGSMEGFVSQDVLTIGDITIKNQ

DFAEATKEPGLAFAFGKFDGILGLGYDTISVNHITPPFYQMMNQKL

VDSPVFSFRLGSSEEDGGEAIFGGVDETAYSGKIEYVPVRRKAYWE

VELESIKLGDDELELDNTGAAIDTGTSLIALPSDLAEMLNVQIGAK

KSWNGQYTVDCAKVPTLPDLTFYFSGKPYTLKGTDYVLEVQGTCMS

SFTGIDINLPGGGALWIIGDVFLRKYYTVYDHGRDAVGFALAK*

1.2.3.5 Primer Walking 4

For primer walking 4, new reverse primers were constructed, and PCR was performed using the SMART IV primer (the beginning of every cDNA) as a forward primer. Various conditions concerning buffers, temperatures and extension/annealing times were studied, but while none of the conditions tested resulted in the formation of clear bands, blurring was observed each time. Possibly, SMART IV, which was contained in all DNA segments, bound at several sites and thus underwent extension. Based on the failure of all testing conditions, the SpeedUp™ Premix Kit II for DNA Walking (cat. no. K1503, Seegene, South Korea) was used in the last step of primer walking.

The kit consists of a PCT master mix an unique DNA walking ACP primers, which are constructed to capture unknown target sites with high specificity. One of the four ACP primers and the target-specific primer 1 (TSP1) constructed by the inventors themselves were used to amplify the target region from the template in the first PCR. In the second PCR (the first nested PCR), the DW-ACPN primer and the target-specific primer 2 (TSP2) constructed by the inventors themselves were then used to amplify the target from the first PCR product. In the third PCR (the second nested PCR), universal primers and the third target-specific primer 2 (TSP3) constructed by the inventors themselves were used as was the second PCR product as a template.

Figure 17:
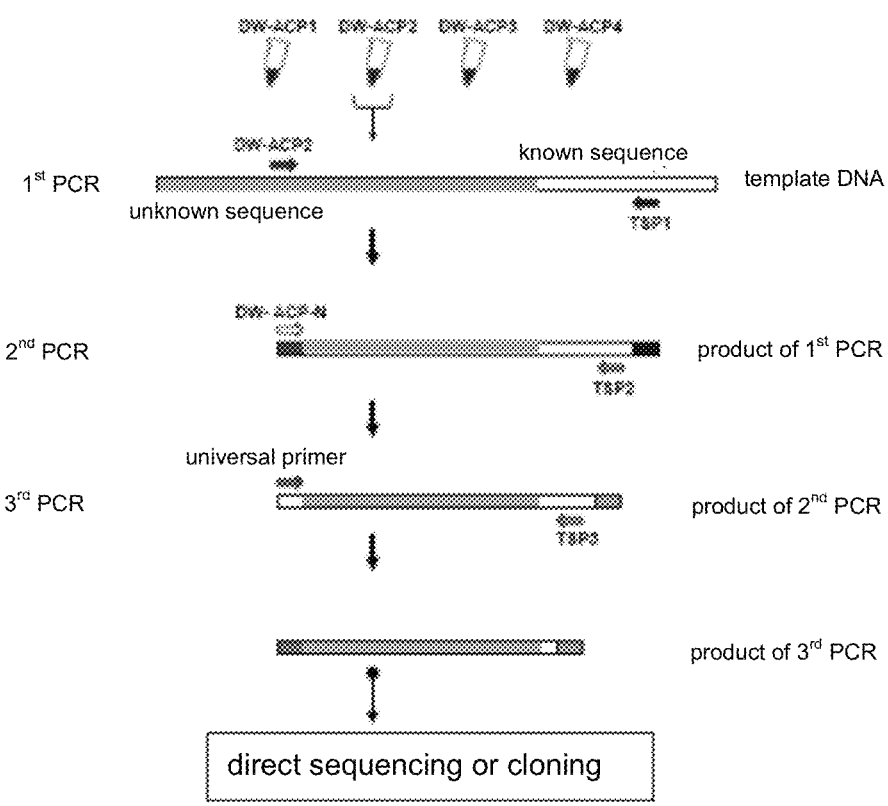
FIG. 17 shows the general procedure of primer walking 4.

FIG. 17 shows this general procedure in DNA walking using ACP™ PCR technology.

1.2.3.5.1 Design of Target-Specific Primers

The requirements for constructing TSPs were the following:
1. The primers should not form hairpin structures.
2. Their 3' ends should not to base-pair with each other.
3. Repetitive sequences or regions containing segments of the same nucleotide had to be avoided.
4. Overlapping of TSP primers was permitted.
5. No ACP primer binding sites (5'-AACGG; 5'-CTCGA; 5'-CTACG; 5'-ACGTG) should be located upstream of the TSP1 primer.
6. The primers should have a length of 18 to 23 bp, a GC content of between 40% and 60% and a Tm of from 60° C. to 65° C.

In the first trial, three TSP1 primers (1.1, 1.2, 1.3) were constructed to have several of them available in case one or the other would not work. The target-specific primers are given below.

TSP1.3 primer:
(SEQ ID NO: 69)
CCC AGT GTC CAG GAT GAC

TSP1.2 primer:
(SEQ ID NO: 70)
ACC TTG AAC GAT TGC GGG

TSP1.1 primer:
(SEQ ID NO: 71)
GGG AGT GCC CAA GGT GA

TSP2 primer:
(SEQ ID NO: 72)
GAG TGC CCA AGG TGA TTT C

TSP3 primer:
(SEQ ID NO: 73)
GGT GAT TTC AGC GAA GTA CT

1.2.3.5.2 Nested Primer PCR

Three PCR reactions were performed successively. The first PCR reaction was performed in four different parallel tubes using primer pairs that were combinations of the TSP1.1 primer with one of the primers DW2-ACP1, -2, -3 and -4, respectively. To save time, the same procedure was chosen for TSP1.2 as well. Altogether, PCR was performed in 8 reaction tubes with the contents given in Table 14 below.

TABLE 14

Contents of 8 reaction tubes for the first PCR of primer walking 4

| | Content | Volume (µL) |
|---|---|---|
| 1. | T. hirsuta cDNA template (350 ng/µL) | 0.2 |
| 2. | DW2-ACP (one of DW2-ACP1, -2, -3, and -4) (5 uM) | 2 |
| 3. | TSP1 (1.1 or 1.2) | 1 |
| 4. | Distilled water | 6.8 |
| 5. | 2X SeeAmp ™ACP ™ Master Mix II | 10 |

The PCR was carried out in a thermal cycler which was pre-heated to 94° C. (Hotstart). The PCR program for the first PCR is indicated in Table 15.

TABLE 15

PCR program used for the first PCR of primer walking 4

| Step | Temperature (° C.) | Time | Number of cycles |
|---|---|---|---|
| Initial denaturation | 94 | 5 min | 1 |
| Initial annealing | 42 | 1 min | 1 |
| Initial extension | 72 | 2 min | 1 |
| Denaturation | 94 | 30 s | 30 |
| Annealing | 55 | 30 s | |
| Extension | 72 | 100 s | |
| Final extension | 72 | 7 min | 1 |

The PCR products obtained were purified using PCR purification kit (QIAGEN, cat. No. 28106). The purified products (8 tubes in total) were used as the template DNA for the second PCR. The contents for the second PCR carried out are given in Table 16.

TABLE 16

Contents of the 8 reaction tubes for the second PCR of primer walking 4

| Contents | Volume (µL) |
|---|---|
| 1. Purified first PCR product | 3 |
| 2. DW2-ACPN (5 uM) | 2 |
| 3. TSP 2 | 1 |
| 4. Distilled water | 4 |
| 5. 2X SeeAmp ™ACP ™Master Mix II | 10 |

The thermal cycler was pre-heated to 94° C. for carrying out the PCR. The PCR program is given in Table 17.

TABLE 17

PCR program used for the second PCR of primer walking 4

| Step | Temperature (° C.) | Time | Number of cycles |
|---|---|---|---|
| Initial denaturation | 94 | 3 min | 1 |
| Denaturation | 94 | 30 s | 35 |
| Annealing | 60 | 30 s | |
| Extension | 72 | 100 s | |
| Final extension | 72 | 7 min | 1 |

The third PCR, i.e. the second nested PCR, was carried out using the PCR product from the second step as the DNA template and universal primers as primer pairs. The PCR tube contents are given in Table 18 and the PCR program is given in Table 19. Again, the thermal cycler was pre-heated to 94° C.

TABLE 18

Contents of the 8 reaction tubes for the third PCR of primer walking 4

| Contents | Volume (µL) |
|---|---|
| 1. Purified second PCR products | 2 |
| 2. UniP2 (5 uM) | 1 |
| 3. TSP 3 | 1 |
| 4. Distilled water | 6 |
| 5. 2X SeeAmp ™ACP ™ Master Mix II | 10 |

TABLE 19

PCR program used for the third PCR of primer walking 4

| Step | Temperature (° C.) | Time | Number of cycles |
|---|---|---|---|
| Initial denaturation | 94 | 3 min | 1 |
| Denaturation | 94 | 30 s | 30 |
| Annealing | 60 | 30 s | |
| Extension | 72 | 100 s | |
| Final extension | 72 | 7 min | 1 |

Figure 18:
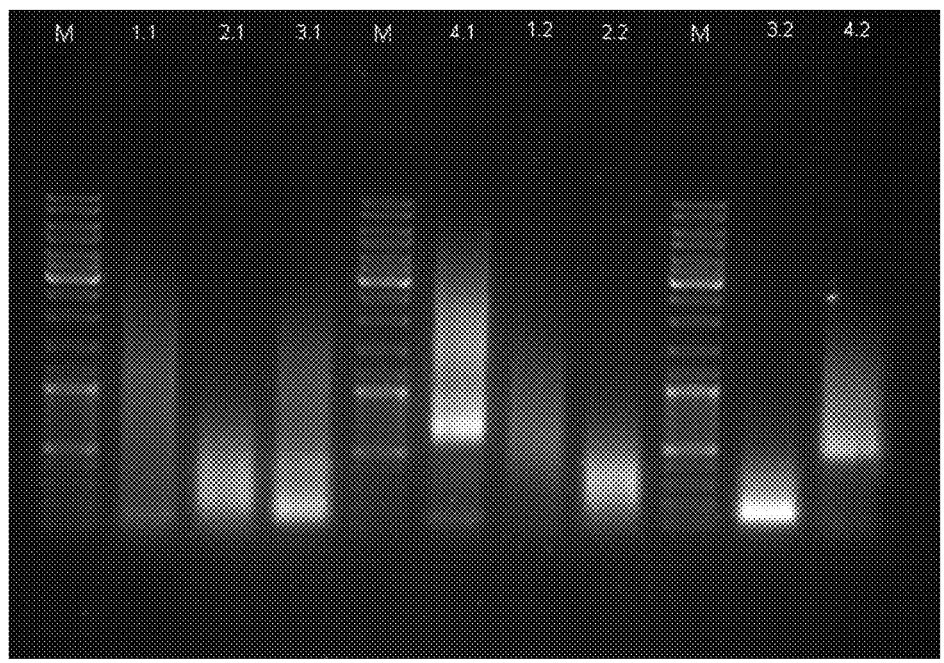
FIG. 18 shows an electropherogram of the products of a third PCR reaction of primer walking 4.

Finally, 10 µL of the sample were analyzed on agarose gel (1%). The results are shown in FIG. 18. The bands in lane 3.1 (around 400 bp), lane 4.1 (around 700 bp), lane 2.2 (around 300 bp) and lane 4.2 (around 500 bp) were excised from the gel, and the DNA was extracted using the QIAGEN gel extraction kit. The excised PCR products had sticky ends, thus, before cloning them into the pJET1.2 vector (blunt end ligation), the ends had to be blunted with a blunting enzyme. The blunting enzyme was provided in the CLONEJET™ PCR cloning kit. The ligation mixture was transformed into competent TOP10 cells. Transformants were picked, overnight cultures were made therewith, the plasmids were isolated and the DNA sequences were analyzed.

1.2.3.5.3 Analysis of DNA Sequences

The sequence of the plasmids carrying the insert was analyzed. One of the products did in fact contain the part of the gene of interest. The TSP3 primer and the universal primer could be identified in the sequence. The translation of the DNA sequence comprised the part of the gene of interest which was previously known, which confirmed that it was contained in the gene. The beginning of the gene of interest was now reached. The obtained DNA sequencing results are indicated below.

```
>Seegene-2-band-4-1-1-3-forward.pJET1.2-F
                                    (SEQ ID NO: 74)
GATGAGTTTAGGTCCAGCGTCCGTGGGGGGGCGTGCGGACGGATC

TGCGAGCGGAACATATCCTCCGCCATATGGGAGCTTTCTTCGTCTT

GAGAGCTGTACATTATCCACTCCAGCTCCTGCAACTTCGCCCCCGC

CAAAAAAAAAAAAAAAAAAAACATGTCGGCCGCCTCGGCCTCTAGA

ATGGGGAAGCAGTGGTATCAACGCAGAGTGGAAGCAGTGGTATCAA

CGCAGAGTGGCCATTACGGCCGGGAAGCAGTGGTATCAACGCAGAG

TGGCCATTACGAAGCAGTGGTATAAACGCAGAGTGGCCATTAAGCA

GTGGTATCAACGCAGAGTGACCATGATACTCTCCAGATTCGCCCCC

CTCGCCCTGCTCCCCTTCGTGGCCGCCGACGGCGTCCACAAGCTGA

AGCTCACCAAGCTTCCTCCCGCAACTTCCAACCCGTTGTTGGAGAG
```

-continued

```
TGCTTACCTGGCTGAGAAGTATGGTGGTGGTTCCCAGATGCCCCTT

AGCGCGGGCATTGGCCGCAACGTCCGCGTGTCGCGCCCGACCGTCA

AGGACGGCGAGGAGCTCTTCTGGACTCAGGACGAGTTTTCGACCGA

GGGCGGTCACAACGTTCCCTTGAGTAACTTCATGAACGCTAGTAC

TTCGCTGAAATCACCATCTTTCTAGAAGATCTCCTACAATATTCTC

AGCTGCCATGGAAAATCGATGTTCTTCTTTTATTCTCTCAAGATTT

TCAGGCTGTATATTAAAACTTATATTAAGAACTATGCTAACCACCT

CATCAGGAACCGTTGTAGGTGGCGTGGGTTTTCTTGGCAATCGACT

CTCATGAAAACTACGAGCTAAATATTCAATATGTTCCTCTTGACCA

ACTTTATTCTGCATTTTTTT

Translation:
>EMBOSS_001_3
                                    (SEQ ID NO: 75)
V*VQRPWGGRADGSASGTYPPPYGSFLRLESCTLSTPAPATSPPPK

KKKKKTCRPPRPLEWGSSGINAEWKQWYQRRVAITAGKQWYQRRVA

ITKQWYKRRVAIKQWYQRRVTMILSRFAPLALLPFVAADGVHKLKL

TKLPPATSNPLLESAYLAEKYGGGSQMPLSAGIGRNVRVSRPTVKD

GEELFWTQDEFSTEGGHNVPLSNFMNAQYFAEIT

>Seegene-2-band-4-1-1-3-reverse.pJET1.2-R
                                    (SEQ ID NO: 76)
GGTGATTTCAGCGAAGTACTGAGCGTTCATGAAGTTACTCAAGGGA

ACGTTGTGACCGCCCTCGGTCGAAAACTCGTCCTGAGTCCAGAAGA

GCTCCTCGCCGTCCTTGACGGTCGGGCGACACGCGGACGTTGCG

GCCAATGCCCGCGCTAAGGGGCATCTGGGAACCACCACCATACTTC

TCAGCCAGGTAAGCACTCTCCAACAACGGGTTGGAAGTTGCGGGAG

GAAGCTTGGTGAGCTTCAGCTTGTGGACGCCGTCGGCGGCCACGAA

GGGGAGCAGGGCGAGGGGGCGAATCTGGAGAGTATCATGGTCACT

CTGCGTTGATACCACTGCTTAATGGCCACTCTGCGTTTATACCACT

GCTTCGTAATGGCCACTCTGCGTTGATACCACTGCTTCCCGGCCGT

AATGGCCACTCTGCGTTGATACCACTGCTTCCACTCTGCGTTGATA

CCACTGCTTCCCCATTCTAGAGGCCGAGGCGGCCGACATGTTTTTT

TTTTTTTTTTTTTGGCGGGGCGAAGTTGCAGGAGCTGGAGTGGA

TAATGTACAGCTCTCAAGACGAAGAAAGCTCCCATATGGCGGAGGA

TATGTTCCGCTCGCAGATCCGTCCGCACGCCCCCCCCACGGACGCT

GGACCTAAACTCATCTTGCTGAAAAACTCGAGCCATCCGGAAGATC

TGGCGGCCGCTCTCCCTATAGTGAGTCGTATTACGCCGGATGGATA

TGGTGTTCAGGCACAAGTGTTAAAGCAGTTGATTTTATTCACTATG

ATGAAAAAACAATGAATGGAACCTGCTCCAAGTTAAAATAGAGAT

AATACCGAAAACTCATCGAGTAGTAAGATTAGAGATAATACAACAA

TAAAAAATGGTTTAGAACTTACTCACAGCGTGATGCTACT
```

Translation:
>EMBOSS_001_4
                                    (SEQ ID NO: 77)
V*VQRPWGGRADGSASGTYPPPYGSFLRLESCTLSTPAPATSPPPK

KKKKKTCRPPRPLEWGSSGINAEWKQWYQRRVAITAGKQWYQRRVA

ITKQWYKRRVAIKQWYQRRVTMILSRFAPLALLPFVAADGVHKLKL

TKLPPATSNPLLESAYLAEKYGGGSQMPLSAGIGRNVRVSRPTVKD

GEELFWTQDEFSTEGGHNVPLSNFMNAQYFAEIT

1) Universal primer:
                                    (SEQ ID NO: 78)
GAGTTTAGGTCCAGCGTCCGT Reverse complement:
                                    (SEQ ID NO: 79)
ACGGACGCTGGACCTAAACTC 2) PW-4 TSP-3:
                                    (SEQ ID NO: 73)
GGTGATTTCAGCGAAGTACT Reverse complement:
                                    (SEQ ID NO: 80)
AGTACTTCGCTGAAATCACC The protein sequence obtained in primer walking step 4 (using the Seegene kit) is given below.

Protein Sequence after Primer Walking Step 4:

(SEQ ID NO: 81)
MILSRFAPLALLPFVAADGVHKLKLTKLPPATSNPLLESAYLAEKY

GGGSQMPLSAGIGRNVRVSRPTVKDGEELFWTQDEFSTEGGHNVPL

S NFMNAQY FAEITLGTPPQS FKVILDT GSSNLWVPSTKCTSI

ACFLHAKYDSTASSTYKANGSEFSIQYGSGSMEGFVSQDVLTIGDI

TIK NQDFAEA TKEPG LAFAFG KFD GILGL GYDTISVNHIT

PPFYQMMNQKLVDSPVFSFRLGSSEEDGGEAIFGGVDETAYSGKIE

YVPVRR KAYWEVE LESIKLGDDELELDNT GAAIDT GTSLIAL

PSDL AEMLNVQI GAKKSWNGQYTVDCAKVPTLPDLTFYFSGKPY

TLKGTDYVLEVQGTCMSSFTGIDINLPGGGAL WIIGDV FLR KY

YTVYDH GRDAVGFALAK*

After primer walking 4, in which 100 amino acid residues were obtained, the peptide sequence of the gene of interest was complete. The whole protein contained 412 amino acid residues starting with the start codon and ending before the stop codon.

The entire amino acid sequence was designated SEQ ID NO: 1 and is indicated below once again using one-letter code, but in a contiguous manner.

SEQ ID NO: 1
MILSRFAPLALLPFVAADGVHKLKLTKLPPATSNPLLESAYLAEKY

GGGSQMPLSAGIGRNVRVSRPTVKDGEELFWTQDEFSTEGGHNVPL

SNFMNAQYFAEITLGTPPQSFKVILDTGSSNLWVPSTKCTSIACFL

HAKYDSTASSTYKANGSEFSIQYGSGSMEGFVSQDVLTIGDITIKN

QDFAEATKEPGLAFAFGKFDGILGLGYDTISVNHITPPFYQMMNQK

-continued

LVDSPVFSFRLGSSEEDGGEAIFGGVDETAYSGKIEYVPVRR<u>KAYW</u>

<u>EVE</u>LESIKLGDDELELDNT<u>GAAIDTGTSLIALPSDLAEMLNVQI</u>GA

KKSWNGQYTVDCAKVPTLPDLTFYFSGKPYTLKGTDYVLEVQGTCM

SSFTGIDINLPGGGAL<u>WIIGDVFLRKYYTVYDHG</u>RDAVGFALAK*

The corresponding sequence in three-letter code is found in the attached sequence listing.

1.2.3.6 Deducing the Complete Gene Sequence

The portions of the gene obtained from an initial PCR and the different steps of primer walking that followed were put together in order to deduce the complete gene sequence. The complete gene sequence was designated SEQ ID NO: 3 and is given below:

```
                                         SEQ ID NO: 3
ATGATACTCTCCAGATTCGCCCCCCTCGCCCTGCTCCCCTTCGTGG

CCGCCGACGGCGTCCACAAGCTGAAGCTCACCAAGCTTCCTCCCGC

AACTTCCAACCCGTTGTTGGAGAGTGCTTACCTGGCTGAGAAGTAT

GGTGGTGGTTCCCAGATGCCCCTTAGCGCGGGCATTGGCCGCAACG

TCCGCGTGTCGCGCCCGACCGTCAAGGACGGCGAGGAGCTCTTCTG

GACTCAGGACGAGTTTTCGACCGAGGGCGGTCACAACGTTCCCTTG

AGTAACTTCATGAACGCTCAGTACTTCGCTGAAATCACCTTGGGCA

CTCCCCCGCAATCGTTCAAGGTCATCCTGGACACTGGGTCGAGCAA

CCTCTGGGTTCCGAGCACCAAGTGTACCTCCATTGCGTGCTTCCTA

CACGCCAAGTATGACTCGACCGCTTCGTCGACATACAAGGCGAACG

GCTCCGAGTTCTCGATCCAGTATGGCTCTGGCTCCATGGAGGGCTT

CGTCTCGCAAGATGTCTTGACAATCGGTGACATCACCATCAAGAAC

CAAGATTTCGCAGAGGCCACCAAGGAGCCCGGCCTCGCATTTGCCT

TTGGCAAGTTTGATGGTATCCTCGGCCTCGGGTATGACACCATTTC

CGTGAACCACATCACTCCTCCCTTCTACCAGATGATGAACCAGAAG

CTCGTCGATTCTCCTGTGTTCTCTTTCCGCCTCGGTAGCTCGGAAG

AGGACGGTGGTGAAGCCATCTTCGGAGGAGTCGATGAGACCGCGTA

CAGTGGCAAGATCGAATACGTCCCTGTCAGGAGGAAGGCGTACTGG

GAGGTGGAGCTGGAATCGATCAAACTCGGAGACGACGAGCTTGAGC

TCGATAACACCGGCGCTGCCATCGACACTGGAACCTCGTTGATTGC

TCTCCCCTCCGATCTGGCGGAGATGCTCAATGTGCAAATCGGTGCC

AAGAAGTCCTGGAATGGTCAGTACACCGTCGACTGCGCGAAGGTCC

CTACCCTCCCCGACCTCACCTTCTACTTCAGCGGCAAGCCTTACAC

TCTCAAGGGTACCGACTACGTCCTCGAAGTTCAGGGAACTTGCATG

TCCTCGTTCACCGGCATCGACATCAATCTGCCCGGCGGTGGTGCTC

TGTGGATCATTGGTGATGTCTTCCTGCGCAAGTACTACACTGTGTA

CGACCATGGTCGCGATGCCGTT<u>GGCTTCGCTCTTGCCAAGT</u>
```

1.2.3.7 Isolation of the Complete Gene from cDNA and Genomic DNA

New primers were now designed for isolating the complete gene from cDNA and genomic DNA. The gene also had to be isolated from genomic DNA in order to compare the two sequences and check if there were any mutations when the reverse transcription was conducted. The designed primers comprised an NdeI restriction site at the forward primer and a XhoI restriction site at the reverse primer. The primer sequences are marked in SEQ ID NO: 2 above.

```
Forward primer:
                                       (SEQ ID NO: 82)
AAT TAC ATA TGA TAC TCT CCA GAT TCG CCC CC
(NdeI site)

Reverse primer:
                                       (SEQ ID NO: 83)
AATTCTC GAG TCA CTT GGC AAG AGC GAA GCC
(XhoI site)
```

Two PCRs were carried out, one with cDNA of *T. hirsuta* as the template and the other with genomic DNA of *T. hirsuta* as the template. peqGOLD Tissue DNA Mini Kit (order no. 12-3396-00) was used to isolate the genomic DNA of the fungus. The attached manufacturer's protocol in the kit was accurately followed, with 35 μg of genomic DNA being isolated, starting from 40 mg of lyophilized cells. The composition of the PCR reaction mixtures is given in Table 20, and the PCR program is given in Table 21.

TABLE 20

PCR reaction mixtures for obtaining the complete gene from cDNA as well as genomic DNA

| | Volume (μL) | |
|---|---|---|
| Contents | cDNA template | Genomic DNA template |
| Phusion Buffer 5X HF | 10 | 10 |
| dNTPs (10 mM) | 1 | 1 |
| Forward primer (1/10 diluted) | 1 | 1 |
| Reverse primer (1/10 diluted) | 1 | 1 |
| Template DNA (350 ng/μL) | 0.5 | 0.5 |
| Sterile water | 36 | 36 |
| DNA polymerase (Phusion) | 0.5 | 0.5 |

TABLE 21

PCR program for amplifying the gene from cDNA and genomic DNA

| Step | Temperature (° C.) | Time | Number of cycles |
|---|---|---|---|
| Initial denaturation | 98 | 3 min | 1 |
| Denaturation | 98 | 30 s | 40 |
| Annealing | 65 | 30 s | |
| Extension | 72 | 100 s | |
| Final extension | 72 | 7 min | 1 |

Figure 19:
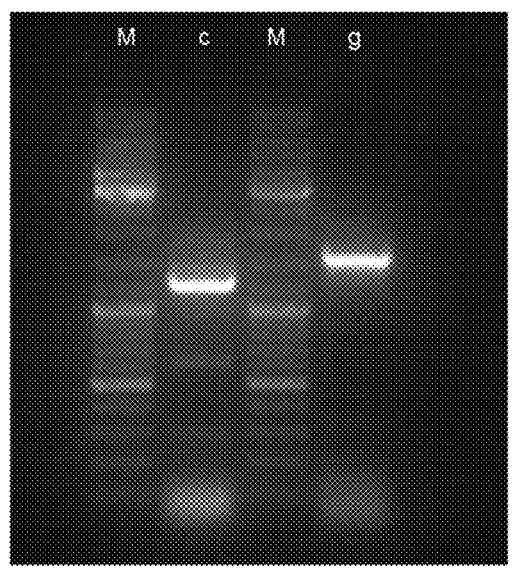
FIG. 19 shows an electropherogram of the complete gene encoding the enzyme.

After PCR, the samples were analyzed on agarose gel (1%) alongside a marker. The gene could be amplified from both the cDNA template and the genomic DNA template. Analysis results are shown in FIG. 19, where "c" represents cDNA and "g" represents genomic DNA as the template.

1.2.3.8 Sequence Verification of the Obtained Gene

Figure 20B:
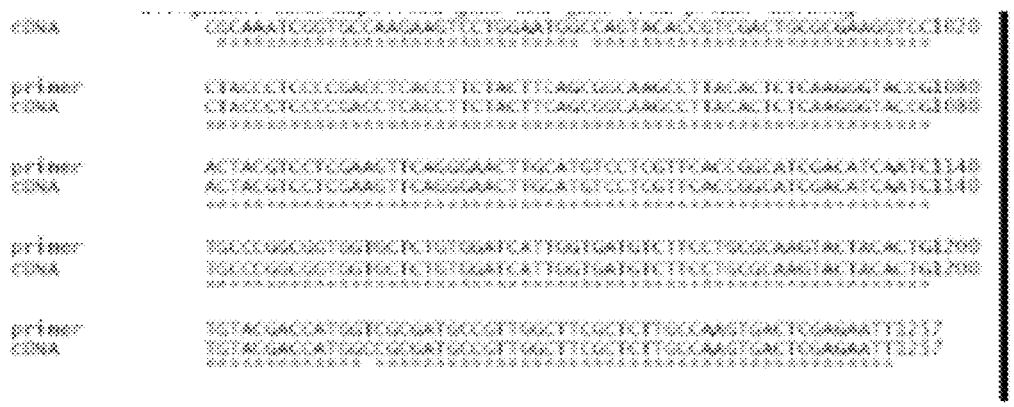
FIG. 20 shows a sequence alignment of the complete gene as isolated (SEQ ID NO: 4) and as assembled from partial primer walking segments (SEQ ID NO: 3) using Clustal 2.1 software.

The two bands were cut out from the gel and the DNA was eluted out, the genes were ligated into the pJET 1.2 vectors (CLONEJET™, blunt vector) and transformed into E. coli TOP 10 cells. The overnight cultures of three picked colonies were made and the samples were sequenced to verify the gene sequence. The sequencing results showed that there were seven base pair differences between the final gene isolated and the gene sequence acquired by putting the segments together from the four primer walking steps. Sequence comparison between the two sequences using the Clustal 2.1 multiple sequence alignment software is given in FIG. 20.

These differences, however, resulted in only a single amino acid difference at position 318, where valine is found instead of alanine. FIG. 21 shows a comparison between the amino acid sequences using the Clustal 2.1 software. The difference in amino acids can be discerned from the missing asterisk in position 318. The actual amino acid sequence of the isolated enzyme thus determined was designated SEQ ID NO: 2, and the sequence encoding the same was designated SEQ ID NO: 4. Both are given in the attached sequence listing.

In addition, overlapping of the gene sequence obtained from genomic DNA as the template with the gene sequence obtained from the cDNA template revealed the presence of six intron sequences dispersed within the gene, as this can be well seen in the Clustal 2.1 sequence alignment shown in FIG. 22.

1.2.3.9 Ligation of the Gene into pET-21(a) Vector

Additionally some amount of the gene from the cDNA template were restricted with Nde I and Xho I from the pJET1.2 vector. The reaction mixture for the restriction digestion step is given in Table 22 below.

TABLE 22

Reaction mixture for the restriction digestion of the gene from cDNA template from pJET1.2 vector

| Component | Quantity (µL) |
| --- | --- |
| Water (nuclease-free) | 13 |
| Fast Digest ® Green buffer (Fermentas) | 7.7 |
| Mini-prep sample (16 ng/µL) | 8 (50 ng) |
| Fast Digest ® Xho I | 1 |
| Fast Digest ® Nde I | 1 |

Figure 23:
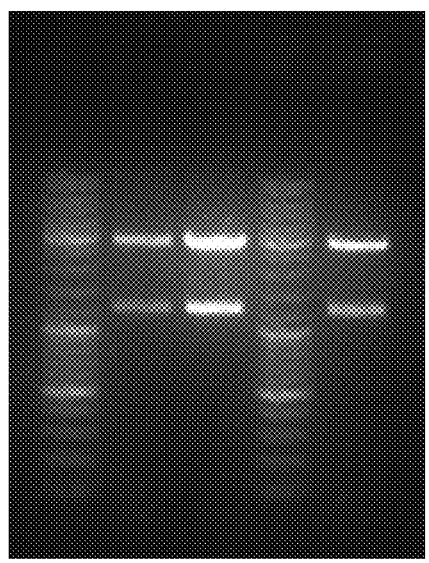
FIG. 23 shows an electropherogram of three reaction mixtures for restriction digestion of the gene from the pJET1.2 vector.

The samples were then analyzed on agarose gel, and the results are shown in FIG. 23.

The restricted gene was then ligated into a pET-21(a) vector previously restricted with the same pair of restriction enzymes. The ligation reaction mixture is given in Table 1.24. The vector was then transformed into E. coli XL1-Blue cells in order to amplify the gene containing the vector.

TABLE 23

Subcloning of the gene cleaved with NdeI and XhoI into pET-21(a)

| Component | Amount (µL) |
| --- | --- |
| T4 Ligation buffer (10X) (Fermentas) | 2 |
| Gene from cDNA template (12.8 ng/µL) | 4.5 |
| pET-21a(+) plasmid vector (17.8 ng/µL) | 2.8 |

TABLE 23-continued

Subcloning of the gene cleaved with NdeI and XhoI into pET-21(a)

| Component | Amount (µL) |
| --- | --- |
| Sterile water | 1.3 |
| T4 DNA ligase (Fermentas) | 1 |

The recombinant plasmid was then transformed into E. coli BL(21).pTf16 cells. Certain transformant colonies were picked up, overnight cultures were made therewith. These were then used as the seed culture for a larger culture. Expression of the enzyme was induced by the addition of IPTG. The resulting cell pellet was resuspended in Bis-Tris buffer (pH 6, 50 mM), ultrasonicated in order to break open the cells and then centrifuged in order to separate the soluble PF1 protein fraction, which was then examined for catalytic activity in alkene cleavage.

The PF1 fraction was tested for alkene cleavage activity in duplicates under standard reaction conditions (6 mM t-anethole substrate, 0.4 mM Mn(III) acetate; 2 bar oxygen pressure, shaking at 170 rpm, room temperature, 36 h). On an average, 38 conversion of the substrate to the corresponding alkene cleavage product, i.e. p-anisaldehyde, were found.

1.2.3.10 Recombinant Production of the Gene

For expression using a His tag, the gene was again ligated into the pET-21(a) vector and transformed into E. coli BL21 Codon Plus (DE3). The cells were cultured with ampicillin (100 µg/L) in LB media (250 mL in 1 L shaking flasks) at 37° C. and 120 rpm, until the $OD_{600}$ reached the value of 0.6. Following induction with IPTG (isopropyl-β-thiogalactoside; 0.3 mM), the reaction mixture was incubated for 16 h at 20° C. The cells were then centrifuged (8,000 rpm, 4° C., 20 min), the cell pellet was resuspended in Bis-Tris buffer (pH 6, 50 mM) and lyophilized. For subsequent catalyzed reaction, cell-free extracts were used, for which the cells were resuspended in buffer and solubilized in ice using ultrasound (30% amplitude; 1 s pulse on, 4 s pulse off; 2 min 30 s).

From this stock, the soluble fraction, PF2, was again purified according to standard protocols, and then the purified enzyme was tested for activity in alkene cleavage as described above for PF2. An average conversion to p-anisaldehyde of 67% could be achieved.

The inventors have thus managed to isolate a new enzyme from Trametes hirsuta, which is effective as a catalyst in alkene cleavage, and to completely clarify (SEQ ID NO: 1) and verify (SEQ ID NO: 2) its structure and amino acid sequence. The catalytic effectiveness of the enzyme can be considerably increased by adding $Mn^{3+}$ ions, which suggests that manganese(III) is a co-factor for the enzyme. In addition, the sequence of the gene encoding the enzyme was determined (SEQ ID NO: 3), after which the gene could be isolated from the fungal strain as well and its sequence could be verified (SEQ ID NO: 4). With this enzyme, the present invention is a highly efficient catalyst for the biologically catalyzed cleavage of alkenes.

Deposit of Biological Material

According to the provisions of the Budapest Treaty on the International Recognition of the Deposit of Microorganisms for the Purposes of Patent Procedure, a vital sample of the Trametes stain Trametes hirsuta FCC 047 was deposited with the National Collection of Agricultural and Industrial Microorganisms (NCAIM) at the Corvinus University in Budapest, Somlói út 14-16, 1118, Hungary, on Apr. 11, 2012. The stain was assigned the accession number NCAIM (P) F 001404.

SEQUENCE LISTING

<160> NUMBER OF SEQ ID NOS: 96

<210> SEQ ID NO 1
<211> LENGTH: 412
<212> TYPE: PRT
<213> ORGANISM: Trametes hirsuta

<400> SEQUENCE: 1

```
Met Ile Leu Ser Arg Phe Ala Pro Leu Ala Leu Leu Pro Phe Val Ala
1               5                   10                  15

Ala Asp Gly Val His Lys Leu Lys Leu Thr Lys Leu Pro Pro Ala Thr
            20                  25                  30

Ser Asn Pro Leu Leu Glu Ser Ala Tyr Leu Ala Glu Lys Tyr Gly Gly
        35                  40                  45

Gly Ser Gln Met Pro Leu Ser Ala Gly Ile Gly Arg Asn Val Arg Val
    50                  55                  60

Ser Arg Pro Thr Val Lys Asp Gly Glu Leu Phe Trp Thr Gln Asp
65                  70                  75                  80

Glu Phe Ser Thr Glu Gly Gly His Asn Val Pro Leu Ser Asn Phe Met
                85                  90                  95

Asn Ala Gln Tyr Phe Ala Glu Ile Thr Leu Gly Thr Pro Pro Gln Ser
            100                 105                 110

Phe Lys Val Ile Leu Asp Thr Gly Ser Ser Asn Leu Trp Val Pro Ser
        115                 120                 125

Thr Lys Cys Thr Ser Ile Ala Cys Phe Leu His Ala Lys Tyr Asp Ser
130                 135                 140

Thr Ala Ser Ser Thr Tyr Lys Ala Asn Gly Ser Glu Phe Ser Ile Gln
145                 150                 155                 160

Tyr Gly Ser Gly Ser Met Glu Gly Phe Val Ser Gln Asp Val Leu Thr
                165                 170                 175

Ile Gly Asp Ile Thr Ile Lys Asn Gln Asp Phe Ala Glu Ala Thr Lys
            180                 185                 190

Glu Pro Gly Leu Ala Phe Ala Phe Gly Lys Phe Asp Gly Ile Leu Gly
        195                 200                 205

Leu Gly Tyr Asp Thr Ile Ser Val Asn His Ile Thr Pro Pro Phe Tyr
    210                 215                 220

Gln Met Met Asn Gln Lys Leu Val Asp Ser Pro Val Phe Ser Phe Arg
225                 230                 235                 240

Leu Gly Ser Ser Glu Glu Asp Gly Gly Glu Ala Ile Phe Gly Gly Val
                245                 250                 255

Asp Glu Thr Ala Tyr Ser Gly Lys Ile Glu Tyr Val Pro Val Arg Arg
            260                 265                 270

Lys Ala Tyr Trp Glu Val Glu Leu Glu Ser Ile Lys Leu Gly Asp Asp
        275                 280                 285

Glu Leu Glu Leu Asp Asn Thr Gly Ala Ala Ile Asp Thr Gly Thr Ser
    290                 295                 300

Leu Ile Ala Leu Pro Ser Asp Leu Ala Glu Met Leu Asn Val Gln Ile
305                 310                 315                 320

Gly Ala Lys Lys Ser Trp Asn Gly Gln Tyr Thr Val Asp Cys Ala Lys
                325                 330                 335

Val Pro Thr Leu Pro Asp Leu Thr Phe Tyr Phe Ser Gly Lys Pro Tyr
            340                 345                 350

Thr Leu Lys Gly Thr Asp Tyr Val Leu Glu Val Gln Gly Thr Cys Met
        355                 360                 365
```

```
Ser Ser Phe Thr Gly Ile Asp Ile Asn Leu Pro Gly Gly Ala Leu
    370                 375                 380

Trp Ile Ile Gly Asp Val Phe Leu Arg Lys Tyr Tyr Thr Val Tyr Asp
385                 390                 395                 400

His Gly Arg Asp Ala Val Gly Phe Ala Leu Ala Lys
                405                 410

<210> SEQ ID NO 2
<211> LENGTH: 412
<212> TYPE: PRT
<213> ORGANISM: Trametes hirsuta

<400> SEQUENCE: 2

Met Ile Leu Ser Arg Phe Ala Pro Leu Ala Leu Pro Phe Val Ala
1               5                   10                  15

Ala Asp Gly Val His Lys Leu Lys Leu Thr Lys Leu Pro Ala Thr
                20                  25                  30

Ser Asn Pro Leu Leu Glu Ser Ala Tyr Leu Ala Glu Lys Tyr Gly Gly
                35                  40                  45

Gly Ser Gln Met Pro Leu Ser Ala Gly Ile Gly Arg Asn Val Arg Val
    50                  55                  60

Ser Arg Pro Thr Val Lys Asp Gly Glu Glu Leu Phe Trp Thr Gln Asp
65                  70                  75                  80

Glu Phe Ser Thr Glu Gly Gly His Asn Val Pro Leu Ser Asn Phe Met
                85                  90                  95

Asn Ala Gln Tyr Phe Ala Glu Ile Thr Leu Gly Thr Pro Pro Gln Ser
                100                 105                 110

Phe Lys Val Ile Leu Asp Thr Gly Ser Ser Asn Leu Trp Val Pro Ser
            115                 120                 125

Thr Lys Cys Thr Ser Ile Ala Cys Phe Leu His Ala Lys Tyr Asp Ser
130                 135                 140

Thr Ala Ser Ser Thr Tyr Lys Ala Asn Gly Ser Glu Phe Ser Ile Gln
145                 150                 155                 160

Tyr Gly Ser Gly Ser Met Glu Gly Phe Val Ser Gln Asp Val Leu Thr
                165                 170                 175

Ile Gly Asp Ile Thr Ile Lys Asn Gln Asp Phe Ala Glu Ala Thr Lys
            180                 185                 190

Glu Pro Gly Leu Ala Phe Ala Phe Gly Lys Phe Asp Gly Ile Leu Gly
            195                 200                 205

Leu Gly Tyr Asp Thr Ile Ser Val Asn His Ile Thr Pro Pro Phe Tyr
210                 215                 220

Gln Met Met Asn Gln Lys Leu Val Asp Ser Pro Val Phe Ser Phe Arg
225                 230                 235                 240

Leu Gly Ser Ser Glu Glu Asp Gly Gly Glu Ala Ile Phe Gly Gly Val
                245                 250                 255

Asp Glu Thr Ala Tyr Ser Gly Lys Ile Glu Tyr Val Pro Val Arg Arg
            260                 265                 270

Lys Ala Tyr Trp Glu Val Glu Leu Glu Ser Ile Lys Leu Gly Asp Asp
            275                 280                 285

Glu Leu Glu Leu Asp Asn Thr Gly Ala Ala Ile Asp Thr Gly Thr Ser
        290                 295                 300

Leu Ile Ala Leu Pro Ser Asp Leu Ala Glu Met Leu Asn Ala Gln Ile
305                 310                 315                 320

Gly Ala Lys Lys Ser Trp Asn Gly Gln Tyr Thr Val Asp Cys Ala Lys
                325                 330                 335
```

Val Pro Thr Leu Pro Asp Leu Thr Phe Tyr Phe Ser Gly Lys Pro Tyr
                340                 345                 350

Thr Leu Lys Gly Thr Asp Tyr Val Leu Glu Val Gln Gly Thr Cys Met
            355                 360                 365

Ser Ser Phe Thr Gly Ile Asp Ile Asn Leu Pro Gly Gly Ala Leu
        370                 375                 380

Trp Ile Ile Gly Asp Val Phe Leu Arg Lys Tyr Tyr Thr Val Tyr Asp
385                 390                 395                 400

His Gly Arg Asp Ala Val Gly Phe Ala Leu Ala Lys
                405                 410

<210> SEQ ID NO 3
<211> LENGTH: 1237
<212> TYPE: DNA
<213> ORGANISM: Trametes hirsuta

<400> SEQUENCE: 3
atgatactct ccagattcgc cccctcgcc ctgctcccct cgtggccgc cgacggcgtc      60 cacaagctga agctcaccaa gcttcctccc gcaacttcca acccgttgtt ggagagtgct    120
tacctggctg agaagtatgg tggtggttcc cagatgcccc ttagcgcggg cattggccgc   180
aacgtccgcg tgtcgcgccc gaccgtcaag gacggcgagg agctcttctg gactcaggac   240
gagttttcga ccgagggcgg tcacaacgtt cccttgagta acttcatgaa cgctcagtac   300
ttcgctgaaa tcaccttggg cactcccccg caatcgttca aggtcatcct ggacactggg   360
tcgagcaacc tctgggttcc gagcaccaag tgtacctcca ttgcgtgctt cctacacgcc   420
aagtatgact cgaccgcttc gtcgacatac aaggcgaacg gctccgagtt ctcgatccag   480
tatggctctg gctccatgga gggcttcgtc tcgcaagatg tcttgacaat cggtgacatc   540
accatcaaga ccaagatttt cgcagaggcc accaaggagc ccggcctcgc atttgccttt   600
ggcaagtttg atggtatcct cggcctcggg tatgacacca tttccgtgaa ccacatcact   660 cctccttct accagatgat gaaccagaag ctcgtcgatt ctcctgtgtt ctctttccgc   720
ctcggtagct cggaagagga cggtggtgaa gccatcttcg gaggagtcga tgagaccgcg   780
tacagtggca agatcgaata cgtccctgtc aggaggaagg cgtactggga ggtggagctg   840
gaatcgatca aactcggaga cgacgagctt gagctcgata caccggcgc tgccatcgac   900 actggaacct cgttgattgc tctcccctcc gatctggcgg agatgctcaa tgtgcaaatc   960
ggtgccaaga agtcctggaa tggtcagtac accgtcgact gcgcgaaggt ccctaccctc  1020
cccgacctca ccttctactt cagcggcaag ccttacactc tcaagggtac cgactacgtc  1080
ctcgaagttc agggaacttg catgtcctcg ttcaccggca tcgacatcaa ctgcccggc   1140 ggtggtgctc tgtggatcat tggtgatgtc ttcctgcgca agtactacac tgtgtacgac  1200
catggtcgcg atgccgttgg cttcgctctt gccaagt                            1237

<210> SEQ ID NO 4
<211> LENGTH: 1237
<212> TYPE: DNA
<213> ORGANISM: Trametes hirsuta

<400> SEQUENCE: 4
atgatactct ccagattcgc cccctcgcc ctgctcccct cgtggccgc cgacggcgtc      60 cacaagctga agctcaccaa gcttcctccc gcaacttcca acccgttgtt ggagagtgct    120
tacctggctg agaagtatgg tggtggttcc cagatgcccc ttagcgcggg cattggccgc   180

```
aacgtccgcg tgtcgcgccc gaccgtcaag gacggcgagg agctcttctg gactcaggac    240
gagttttcga ccgagggcgg tcacaacgtt cccttgagta acttcatgaa cgctcagtac    300
ttcgctgaaa tcaccttggg cactcccccg caatcgttca aggtcatcct ggacactggg    360
tcgagcaacc tctgggttcc gagcaccaag tgtacctcca ttgcgtgctt cctacacgcc    420
aagtatgact cgaccgcttc gtcgacatac aaggcgaacg gctccgagtt ctcgatccag    480
tatggctctg gctccatgga gggcttcgtc tcgcaagatg tcttgacaat cggtgacatc    540
accatcaaga accaagattt cgcagaggcc accaaggagc ccggcctcgc atttgccttt    600
ggcaagtttg atggtatcct cggcctcggg tatgacacca tttccgtgaa ccacatcact    660
cctcccttct accagatgat gaaccagaag ctcgtcgatt ctcctgtgtt ctctttccgc    720
ctcggtagct cggaagagga cggtggtgaa gccatcttcg gaggagtcga tgagaccgcg    780
tacagtggca agatcgaata cgtccctgtc aggaggaagg cgtactggga ggtggagctg    840
gaatcgatca aactcggaga cgacgagctt gagctcgata caccggcgc tgccatcgac    900 actggaaacct cgttgattgc tctcccctcc gatctggcgg agatgctcaa tgcgcaaatc    960
ggtgccaaga agtcctggaa tggtcagtac accgtcgact gcgcgaaggt ccctacccctc   1020 cccgacctca ccttctactt cagcggcaag ccttacactc tcaagggtac cgactacgtc   1080
ctcgaagttc agggaacttg catgtcctcg ttcaccggca tcgacatcaa tctgcccggc   1140
ggtggtgctc tgtggatcat tggtgatgtc ttcctgcgca agtactacac tgtgtacgac   1200
catggtcgcg atgccgttgg cttcgctctt gccaagt                              1237
```

```
<210> SEQ ID NO 5
<211> LENGTH: 10
<212> TYPE: PRT
<213> ORGANISM: Artificial Sequence
<220> FEATURE:
<223> OTHER INFORMATION: peptide identified by de novo sequencing

<400> SEQUENCE: 5

Glu Pro Gly Leu Ala Phe Ala Phe Gly Lys
1               5                   10

<210> SEQ ID NO 6
<211> LENGTH: 10
<212> TYPE: PRT
<213> ORGANISM: Artificial Sequence
<220> FEATURE:
<223> OTHER INFORMATION: peptide identified by de novo sequencing

<400> SEQUENCE: 6

Leu Val Asp Ser Pro Val Phe Ser Phe Arg
1               5                   10

<210> SEQ ID NO 7
<211> LENGTH: 10
<212> TYPE: PRT
<213> ORGANISM: Artificial Sequence
<220> FEATURE:
<223> OTHER INFORMATION: peptide identified by de novo sequencing

<400> SEQUENCE: 7

Lys Tyr Tyr Thr Val Tyr Asp His Gly Arg
1               5                   10

<210> SEQ ID NO 8
<211> LENGTH: 19
```

```
<212> TYPE: PRT
<213> ORGANISM: Artificial Sequence
<220> FEATURE:
<223> OTHER INFORMATION: peptide identified by de novo sequencing

<400> SEQUENCE: 8

Asn Gln Asp Phe Ala Glu Ala Thr Lys Glu Pro Gly Leu Ala Phe Ala
1               5                   10                  15

Phe Gly Lys

<210> SEQ ID NO 9
<211> LENGTH: 9
<212> TYPE: PRT
<213> ORGANISM: Artificial Sequence
<220> FEATURE:
<223> OTHER INFORMATION: peptide identified by de novo sequencing

<400> SEQUENCE: 9

Tyr Tyr Thr Val Tyr Asp His Gly Arg
1               5

<210> SEQ ID NO 10
<211> LENGTH: 11
<212> TYPE: PRT
<213> ORGANISM: Artificial Sequence
<220> FEATURE:
<223> OTHER INFORMATION: peptide identified by de novo sequencing

<400> SEQUENCE: 10

Ala Tyr Trp Glu Val Glu Leu Glu Ser Ile Lys
1               5                   10

<210> SEQ ID NO 11
<211> LENGTH: 24
<212> TYPE: PRT
<213> ORGANISM: Artificial Sequence
<220> FEATURE:
<223> OTHER INFORMATION: peptide identified by de novo sequencing

<400> SEQUENCE: 11

Leu Gly Ser Ser Glu Glu Asp Gly Gly Glu Ala Leu Phe Gly Gly Val
1               5                   10                  15

Asp Glu Thr Ala Tyr Ser Gly Lys
            20

<210> SEQ ID NO 12
<211> LENGTH: 9
<212> TYPE: PRT
<213> ORGANISM: Artificial Sequence
<220> FEATURE:
<223> OTHER INFORMATION: peptide identified by de novo sequencing

<400> SEQUENCE: 12

Asn Gln Asp Phe Ala Glu Ala Thr Lys
1               5

<210> SEQ ID NO 13
<211> LENGTH: 12
<212> TYPE: PRT
<213> ORGANISM: Artificial Sequence
<220> FEATURE:
<223> OTHER INFORMATION: peptide identified by de novo sequencing

<400> SEQUENCE: 13

Lys Ala Tyr Trp Glu Val Glu Leu Glu Ser Ile Lys
1               5                   10
```

<210> SEQ ID NO 14
<211> LENGTH: 20
<212> TYPE: DNA
<213> ORGANISM: Artificial Sequence
<220> FEATURE:
<223> OTHER INFORMATION: degenerate forward primer 1
<220> FEATURE:
<221> NAME/KEY: misc_feature
<222> LOCATION: (15)..(15)
<223> OTHER INFORMATION: n is a, c, g, or t

<400> SEQUENCE: 14
aaycargayt tygcngargc                                          20

<210> SEQ ID NO 15
<211> LENGTH: 21
<212> TYPE: DNA
<213> ORGANISM: Artificial Sequence
<220> FEATURE:
<223> OTHER INFORMATION: degenerate forward primer 2
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 15
gargargayg gnggngargc n                                        21

<210> SEQ ID NO 16
<211> LENGTH: 20
<212> TYPE: DNA
<213> ORGANISM: Artificial Sequence
<220> FEATURE:
<223> OTHER INFORMATION: degenerate forward primer 3
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 16
aargcntayt gggargtnga                                          20

<210> SEQ ID NO 17
<211> LENGTH: 20
<212> TYPE: DNA
<213> ORGANISM: Artificial Sequence
<220> FEATURE:
<223> OTHER INFORMATION: degenerate reverse primer 1
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 17

```
tcnacytccc artangcytt                                                     20
```

<210> SEQ ID NO 18
<211> LENGTH: 24
<212> TYPE: DNA
<213> ORGANISM: Artificial Sequence
<220> FEATURE:
<223> OTHER INFORMATION: degenerate reverse primer 2
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t

<400> SEQUENCE: 18

```
crtgrtcrta nacngtrtar tayt                                                24
```

<210> SEQ ID NO 19
<211> LENGTH: 7
<212> TYPE: PRT
<213> ORGANISM: Artificial Sequence
<220> FEATURE:
<223> OTHER INFORMATION: translation of degenerate forward primer 1
      nucleotide sequence

<400> SEQUENCE: 19

Asn Gln Asp Phe Ala Glu Ala
1               5

<210> SEQ ID NO 20
<211> LENGTH: 7
<212> TYPE: PRT
<213> ORGANISM: Artificial Sequence
<220> FEATURE:
<223> OTHER INFORMATION: translation of degenerate forward primer 2
      nucleotide sequence

<400> SEQUENCE: 20

Glu Glu Asp Gly Gly Glu Ala
1               5

<210> SEQ ID NO 21
<211> LENGTH: 7
<212> TYPE: PRT
<213> ORGANISM: Artificial Sequence
<220> FEATURE:
<223> OTHER INFORMATION: translation of degenerate forward primer 3
      nucleotide sequence

<400> SEQUENCE: 21

Lys Ala Tyr Trp Glu Val Glu
1               5

<210> SEQ ID NO 22
<211> LENGTH: 7
<212> TYPE: PRT
<213> ORGANISM: Artificial Sequence
<220> FEATURE:
<223> OTHER INFORMATION: translation of degenerate reverse primer 1
      nucleotide sequence

<400> SEQUENCE: 22

Lys Ala Tyr Trp Glu Val Glu
1               5

```
<210> SEQ ID NO 23
<211> LENGTH: 9
<212> TYPE: PRT
<213> ORGANISM: Artificial Sequence
<220> FEATURE:
<223> OTHER INFORMATION: translation of degenerate reverse primer 2
      nucleotide sequence

<400> SEQUENCE: 23

Lys Tyr Tyr Thr Val Tyr Asp His Gly
1               5

<210> SEQ ID NO 24
<211> LENGTH: 967
<212> TYPE: DNA
<213> ORGANISM: Artificial Sequence
<220> FEATURE:
<223> OTHER INFORMATION: nucleotide sequence of insert in pJET1.2
      plasmid isolated from sample 6a1

<400> SEQUENCE: 24 ttttcagca agataaggct tattgggagg tggagctgga atcgatcaaa ctcggagacg      60
acgagcttga gctcgataac accggcgctg ccatcgacac tggaacctcg ttgattgctc    120 tccccctccga tctggcggag atgctcaatg tgcaaatcgg tgccaagaag tcctggaatg   180
gtcagtacac cgtcgactgc gcgaaggtcc ctaccctccc cgacctcacc ttctacttca    240
gcggcaagcc ttacactctc aagggtaccg actacgtcct cgaagttcag ggaacttgca    300
tgtcctcgtt caccggcatc gacatcaatc tgcccggcgg tggtgctctg tggatcattg    360
gtgatgtctt cctgcgcaag tactacacag tttacgatca cgatctttct agaagatctc    420
ctacaatatt ctcagctgcc atggaaaatc gatgttcttc ttttattctc tcaagatttt    480
caggctgtat attaaaactt atattaagaa ctatgctaac cacctcatca ggaaccgttg    540
taggtggcgt gggttttctt ggcaatcgac tctcatgaaa actacgagct aaatattcaa    600
tatgttcctc ttgaccaact ttattctgca ttttttttga acgagtttta gagcaagctt    660
caggaaactg agacaggaat tttattaaaa atttaaattt tgaagaaagt tcagggttaa    720
tagcatccat ttttttgcttt gcaagttcct cagcattctt aacaaaagac gtctcttttg    780
acatgtttaa agtttaaacc tcctgtgtga aattattatc cgctcataat ccacacatt    840 atacgagccg gaagcataaa gtgtaaagcc tggggtgcct aatgagtgag ctaactcaca    900
ttaattgcgt tgcgctcact gccaattgct ttccagtcgg gaacctgtcg tgccagctgc    960
attaatg                                                              967

<210> SEQ ID NO 25
<211> LENGTH: 134
<212> TYPE: PRT
<213> ORGANISM: Artificial Sequence
<220> FEATURE:
<223> OTHER INFORMATION: translation of nucleotide sequence of insert in
      pJET1.2 plasmid isolated from sample 6a1

<400> SEQUENCE: 25

Phe Gln Gln Asp Lys Ala Tyr Trp Glu Val Glu Leu Glu Ser Ile Lys
1               5                  10                  15

Leu Gly Asp Asp Glu Leu Glu Leu Asp Asn Thr Gly Ala Ala Ile Asp
            20                  25                  30

Thr Gly Thr Ser Leu Ile Ala Leu Pro Ser Asp Leu Ala Glu Met Leu
        35                  40                  45

Asn Val Gln Ile Gly Ala Lys Lys Ser Trp Asn Gly Gln Tyr Thr Val
```

```
            50                  55                  60
Asp Cys Ala Lys Val Pro Thr Leu Pro Asp Leu Thr Phe Tyr Phe Ser
 65                  70                  75                  80

Gly Lys Pro Tyr Thr Leu Lys Gly Thr Asp Tyr Val Leu Glu Val Gln
                 85                  90                  95

Gly Thr Cys Met Ser Ser Phe Thr Gly Ile Asp Ile Asn Leu Pro Gly
            100                 105                 110

Gly Gly Ala Leu Trp Ile Ile Gly Asp Val Phe Leu Arg Lys Tyr Tyr
        115                 120                 125

Thr Val Tyr Asp His Asp
    130

<210> SEQ ID NO 26
<211> LENGTH: 27
<212> TYPE: DNA
<213> ORGANISM: Artificial Sequence
<220> FEATURE:
<223> OTHER INFORMATION: primer walking 1 forward primer (PW1-Fwd)

<400> SEQUENCE: 26
tgtggatcat tggtgatgtc ttcctgc                                       27

<210> SEQ ID NO 27
<211> LENGTH: 25
<212> TYPE: DNA
<213> ORGANISM: Artificial Sequence
<220> FEATURE:
<223> OTHER INFORMATION: primer walking 1 reverse primer (PW1-Rev)

<400> SEQUENCE: 27
gtctccgagt ttgatcgatt ccagc                                         25

<210> SEQ ID NO 28
<211> LENGTH: 25
<212> TYPE: DNA
<213> ORGANISM: Artificial Sequence
<220> FEATURE:
<223> OTHER INFORMATION: SMART-IV forward primer sequence

<400> SEQUENCE: 28
gtatcaacgc agagtggcca ttacg                                         25

<210> SEQ ID NO 29
<211> LENGTH: 24
<212> TYPE: DNA
<213> ORGANISM: Artificial Sequence
<220> FEATURE:
<223> OTHER INFORMATION: CDS III reverse primer sequence

<400> SEQUENCE: 29
cgaggcggcc gacatgttttt tttt                                         24

<210> SEQ ID NO 30
<211> LENGTH: 27
<212> TYPE: DNA
<213> ORGANISM: Artificial Sequence
<220> FEATURE:
<223> OTHER INFORMATION: reverse complement of primer walking 1 forward
      primer (PW1-Rev rev)

<400> SEQUENCE: 30
gcaggaagac atcaccaatg atccaca                                       27
```

```
<210> SEQ ID NO 31
<211> LENGTH: 24
<212> TYPE: DNA
<213> ORGANISM: Artificial Sequence
<220> FEATURE:
<223> OTHER INFORMATION: reverse complement of CDS III reverse primer

<400> SEQUENCE: 31
aaaaaaaaca tgtcggccgc ctcg                                          24

<210> SEQ ID NO 32
<211> LENGTH: 25
<212> TYPE: DNA
<213> ORGANISM: Artificial Sequence
<220> FEATURE:
<223> OTHER INFORMATION: reverse complement of primer walking 1 reverse
      primer (PW1-Rev rev)

<400> SEQUENCE: 32
gctggaatcg atcaaactcg gagac                                         25

<210> SEQ ID NO 33
<211> LENGTH: 25
<212> TYPE: DNA
<213> ORGANISM: Artificial Sequence
<220> FEATURE:
<223> OTHER INFORMATION: reverse complement of SMART-IV forward primer
      (SMART-IV rev)

<400> SEQUENCE: 33
cgtaatggcc actctgcgtt gatac                                         25

<210> SEQ ID NO 34
<211> LENGTH: 844
<212> TYPE: DNA
<213> ORGANISM: Artificial Sequence
<220> FEATURE:
<223> OTHER INFORMATION: nucleotide sequence of insert in pJET1.2
      plasmid after primer walking 1 (2a3 insert)

<400> SEQUENCE: 34
tgtggatcat tggtgatgtc ttcctgcgca agtactacac tgtgtacgac catggtcgcg    60
atgccgttgg cttcgctctt gccaagtgaa ggcgtagtgt atctcccgaa gacagttcta   120
ccgtacgacg cgtcgtgtta cggtttcttg atacctgcat gtacaatact tagtctccgt   180
tggaaccata ccttctgtgt gttgcccaaa aaaaaaaaaa aaaaaaaaaa aaacatgtcg   240
gccgcctcga tctttctaaa aaatctccta caatattctc agctgccatg gaaaatcgat   300
gttcttcttt tattctctca agattttcag gctgtatatt aaaacttata ttaaaaacta   360
tgctaaccac ctcatcagga accgttgtag gtggcgtggg ttttcttggc aatcgactct   420
catgaaaact acgagctaaa tattcaatat gttcctcttg accaactttta ttctgcattt   480 tttttgaacg aggtttagag caagcttcag gaaactgaga caggaattt attaaaaatt   540 taaattttga agaaagttca gggttaatag catccatttt ttgctttgca agttcctcag   600
cattcttaac aaaagacgtc tcttttgaca tgtttaaagt ttaaacctcc tgtgtgaaat   660
tattatccgc tcataattcc acacattata cgagccggaa gcataaagtg taagcctgg   720 ggtgcctaat gagtgagcta actcacatta attgcgttgc gctcactgcc aattgctttc   780
cagtcgggaa acctgtcgtg ccagctgcat taatgaatcg ccaacgcgc ggggagaggc   840 ggtt                                                                844
```

```
<210> SEQ ID NO 35
<211> LENGTH: 81
<212> TYPE: PRT
<213> ORGANISM: Artificial Sequence
<220> FEATURE:
<223> OTHER INFORMATION: translation of nucleotide sequence of insert in
      pJET1.2 plasmid after primer walking 1 (2a3 insert)
<220> FEATURE:
<221> NAME/KEY: misc_feature
<222> LOCATION: (81)..(81)
<223> OTHER INFORMATION: Xaa can be any naturally occurring amino acid

<400> SEQUENCE: 35
```

Trp Ile Ile Gly Asp Val Phe Leu Arg Lys Tyr Tyr Thr Val Tyr Asp
1               5                   10                  15

His Gly Arg Asp Ala Val Gly Phe Ala Leu Ala Lys Arg Arg Ser Val
            20                  25                  30

Ser Pro Glu Asp Ser Ser Thr Val Arg Arg Val Val Leu Arg Phe Leu
        35                  40                  45

Asp Thr Cys Met Tyr Asn Thr Ser Pro Leu Glu Pro Tyr Leu Leu Cys
    50                  55                  60

Val Ala Gln Lys Lys Lys Lys Lys Lys Lys His Val Gly Arg Leu
65                  70                  75                  80

Xaa

```
<210> SEQ ID NO 36
<211> LENGTH: 848
<212> TYPE: DNA
<213> ORGANISM: Artificial Sequence
<220> FEATURE:
<223> OTHER INFORMATION: nucleotide sequence of insert in pJET1.2
      plasmid after primer walking 1 (3b2 insert)

<400> SEQUENCE: 36
gtctccgagt tgatcgatt ccagcgggac atggggacag tcaattaggc tacgcggatg      60
tactgcgcag caaggcatgc cgaccggcct tcatcatgtt atagctatag ctagagcagc    120
gcgagagacc ctgtagagtc actgatgaat cactcgtgct cccttctgtg ccttggctga    180
ataagttttc cacaagttgt cgtggagagt cgtgcaggag ggaggcaact tgccccggc     240 cgtaatggcc actctgcgtt gatacatctt tctagaagat ctcctacaat attctcagct    300
gccatggaaa tcgatgttc ttctttat ctctcaagat tttcaggctg tatattaaaa       360
cttatattaa gaactatgct aaccacctca tcaggaaccg ttgtaggtgg cgtgggtttt    420
cttggcaatc gactctcatg aaaactacga gctaaatatt caatatgttc ctcttgacca    480
actttattct gcattttttt tgaacgaggt ttagagcaag cttcaggaaa ctgagacagg    540
aattttatta aaaatttaaa ttttgaagaa agttcagggt taatagcatc catttttgc     600 tttgcaagtt cctcagcatt cttaacaaaa gacgtctctt ttgacatgtt taaagtttaa    660
acctcctgtg tgaaattatt atccgctcat aattccacac attatacgag ccggaagcat    720
aaagtgtaaa gcctggggtg cctaatgagt gagctaactc acattaattg cgttgcgctc    780
actgccaatt gctttccagt cgggaaacct gtcgtgccag ctgcattaat gaatcggcca    840
acgcgcgg                                                              848

<210> SEQ ID NO 37
<211> LENGTH: 85
<212> TYPE: PRT
<213> ORGANISM: Artificial Sequence
<220> FEATURE:
<223> OTHER INFORMATION: translation of nucleotide sequence of insert in
``` pJET1.2 plasmid after primer walking 1 (3b1 insert)

<400> SEQUENCE: 37

Tyr Gln Arg Arg Val Ala Ile Thr Ala Gly Gly Lys Leu Pro Pro Ser
1               5                   10                  15

Cys Thr Thr Leu His Asp Asn Leu Trp Lys Thr Tyr Ser Ala Lys Ala
            20                  25                  30

Gln Lys Gly Ala Arg Val Ile His Gln Leu Tyr Arg Val Ser Arg Ala
        35                  40                  45

Ala Leu Ala Ile Ala Ile Thr Arg Pro Val Gly Met Pro Cys Cys Ala
    50                  55                  60

Val His Pro Arg Ser Leu Ile Asp Cys Pro His Val Pro Leu Glu Ser
65                  70                  75                  80

Ile Lys Leu Gly Asp
            85

<210> SEQ ID NO 38
<211> LENGTH: 140
<212> TYPE: PRT
<213> ORGANISM: Artificial Sequence
<220> FEATURE:
<223> OTHER INFORMATION: sequence of protein obtained from primer
      walking step 1

<400> SEQUENCE: 38

Lys Ala Tyr Trp Glu Val Glu Leu Glu Ser Ile Lys Leu Gly Asp Asp
1               5                   10                  15

Glu Leu Glu Leu Asp Asn Thr Gly Ala Ala Ile Asp Thr Gly Thr Ser
            20                  25                  30

Leu Ile Ala Leu Pro Ser Asp Leu Ala Glu Met Leu Asn Val Gln Ile
        35                  40                  45

Gly Ala Lys Lys Ser Trp Asn Gly Gln Tyr Thr Val Asp Cys Ala Lys
    50                  55                  60

Val Pro Thr Leu Pro Asp Leu Thr Phe Tyr Phe Ser Gly Lys Pro Tyr
65                  70                  75                  80

Thr Leu Lys Gly Thr Asp Tyr Val Leu Glu Val Gln Gly Thr Cys Met
            85                  90                  95

Ser Ser Phe Thr Gly Ile Asp Ile Asn Leu Pro Gly Gly Gly Ala Leu
            100                 105                 110

Trp Ile Ile Gly Asp Val Phe Leu Arg Lys Tyr Tyr Thr Val Tyr Asp
        115                 120                 125

His Gly Arg Asp Ala Val Gly Phe Ala Leu Ala Lys
    130                 135                 140

<210> SEQ ID NO 39
<211> LENGTH: 21
<212> TYPE: DNA
<213> ORGANISM: Artificial Sequence
<220> FEATURE:
<223> OTHER INFORMATION: primer walking 2 reverse primer 1 (PW-2 rev
      Pri-1)

<400> SEQUENCE: 39
agctcaagct cgtcgtctcc g                                          21

<210> SEQ ID NO 40
<211> LENGTH: 19
<212> TYPE: DNA
<213> ORGANISM: Artificial Sequence
<220> FEATURE:

<223> OTHER INFORMATION: primer walking 2 reverse primer 2 (PW-2 rev Pri-2)

<400> SEQUENCE: 40
agtgtcgatg gcagcgccg                                                    19

<210> SEQ ID NO 41
<211> LENGTH: 25
<212> TYPE: DNA
<213> ORGANISM: Artificial Sequence
<220> FEATURE:
<223> OTHER INFORMATION: primer walking 2 reverse primer 3 (PW-2 rev Pri-3)

<400> SEQUENCE: 41
gatttgcaca ttgagcatct ccgcc                                             25

<210> SEQ ID NO 42
<211> LENGTH: 19
<212> TYPE: DNA
<213> ORGANISM: Artificial Sequence
<220> FEATURE:
<223> OTHER INFORMATION: reverse complement of primer walking 2 reverse primer 2

<400> SEQUENCE: 42
cggcgctgcc atcgacact                                                    19

<210> SEQ ID NO 43
<211> LENGTH: 25
<212> TYPE: DNA
<213> ORGANISM: Artificial Sequence
<220> FEATURE:
<223> OTHER INFORMATION: reverse complement of primer walking 2 reverse primer 3

<400> SEQUENCE: 43
ggcggagatg ctcaatgtgc aaatc                                             25

<210> SEQ ID NO 44
<211> LENGTH: 905
<212> TYPE: DNA
<213> ORGANISM: Artificial Sequence
<220> FEATURE:
<223> OTHER INFORMATION: nucleotide sequence of insert in pJET1.2 plasmid after primer walking 2 (4b1 insert)

<400> SEQUENCE: 44
aaccaggatt tgcggaggc caccaaggag cccggcctcg catttgcctt tggcaagttt        60
gatggtatcc tcggcctcgg gtatgacacc atttccgtga accacatcac tcctcccttc       120
taccagatga tgaaccagaa gctcgtcgat tctcctgtgt tctctttccg cctcggtagc       180
tcggaagagg acggtggtga agccatcttc ggaggagtcg atgagaccgc gtacagtggc       240
aagatcgaat acgtccctgt caggaggaag gcgtactggg aggtggagct ggaatcgatc       300
aaactcggag acgacgagct tgagctcgat aacaccggcg ctgccatcga cactatcttt       360
ctagaagatc tcctacaata ttctcagctg ccatggaaaa tcgatgttct tcttttattc       420
tctcaagatt ttcaggctgt atattaaaac ttatattaag aactatgcta accacctcat       480
caggaaccgt tgtaggtggc gtgggttttc ttggcaatcg actctcatga aaactacgag       540
ctaaatattc aatatgttcc tcttgaccaa cttattctg catttttttt gaacgaggtt        600
tagagcaagc ttcaggaaac tgagacagga attttattaa aaatttaaat tttgaagaaa       660

-continued

```
gttcagggtt aatagcatcc attttttgct ttgcaagttc ctcagcattc ttaacaaaag    720
acgtctcttt tgacatgttt aaagtttaaa cctcctgtgt gaaattatta tccgctcata    780
attccacaca ttatacgagc cggaagcata aagtgtaaag cctggggtgc ctaatgagtg    840
agctaactca cattaattgc gttgcgctca ctgccaattg ctttccagtc gggaaacctg    900
tcgtg                                                                905
```

<210> SEQ ID NO 45
<211> LENGTH: 118
<212> TYPE: PRT
<213> ORGANISM: Artificial Sequence
<220> FEATURE:
<223> OTHER INFORMATION: translation of nucleotide sequence of insert in pJET1.2 plasmid after primer walking 2 (4b1 insert)

<400> SEQUENCE: 45

```
Asn Gln Asp Phe Ala Glu Ala Thr Lys Glu Pro Gly Leu Ala Phe Ala
1               5                   10                  15

Phe Gly Lys Phe Asp Gly Ile Leu Gly Leu Gly Tyr Asp Thr Ile Ser
            20                  25                  30

Val Asn His Ile Thr Pro Pro Phe Tyr Gln Met Met Asn Gln Lys Leu
        35                  40                  45

Val Asp Ser Pro Val Phe Ser Phe Arg Leu Gly Ser Ser Glu Glu Asp
    50                  55                  60

Gly Gly Glu Ala Ile Phe Gly Gly Val Asp Glu Thr Ala Tyr Ser Gly
65                  70                  75                  80

Lys Ile Glu Tyr Val Pro Val Arg Arg Lys Ala Tyr Trp Glu Val Glu
                85                  90                  95

Leu Glu Ser Ile Lys Leu Gly Asp Asp Glu Leu Glu Leu Asp Asn Thr
            100                 105                 110

Gly Ala Ala Ile Asp Thr
        115
```

<210> SEQ ID NO 46
<211> LENGTH: 911
<212> TYPE: DNA
<213> ORGANISM: Artificial Sequence
<220> FEATURE:
<223> OTHER INFORMATION: nucleotide sequence of insert in pJET1.2 plasmid after primer walking 2 (5a1 smallband insert)

<400> SEQUENCE: 46

```
gatttgcaca ttgagcatct ccgccagatc ggaggggaga gcaatcaacg aggttccagt     60
gtcgatggca gcgccggtgt tatcgagctc aagctcgtcg tctccgagtt tgatcgattc    120
cagctccacc tccagtacg ccttcctcct gacaggacg tattcgatct tgccactgta    180
cgcggtctca tcgactcctc cgaagatggc ttcaccaccg tcctcttccg agctaccgag    240
gcggaaagag aacacaggag aatcgacgag cttctggttc atcatctggt agaagggagg    300
agtgatgtgg ttcacggaaa tggtgtcata cccgaggccg aggataccat caaacttgcc    360
aaaggcaaat gcgaggccgg gctccttggt ggcctcagca aaatcctgat tatctttcta    420
gaagatctcc tacaatattc tcagctgcca tggaaaatcg atgttcttct tttattctct    480
caagattttc aggctgtata ttaaaactta tattaagaac tatgctaacc acctcatcag    540
gaaccgttgt aggtggcgtg ggttttcttg gcaatcgact ctcatgaaaa ctacgagcta    600
aatattcaat atgttcctct tgaccaactt tattctgcat ttttttgaa cgaggtttag    660 agcaagcttc aggaaactga gacaggaatt ttattaaaaa tttaaatttt gaagaaagtt    720
```

```
cagggttaat agcatccatt ttttgctttg caagttcctc agcattctta acaaaagacg      780
tctcttttga catgtttaaa gtttaaacct cctgtgtgaa attattatcc gctcataatt      840
ccacacatta tacgagccgg aagcataaag tgtaaagcct ggggtgccta atgagtgagc      900
taactcacat t                                                           911
```

```
<210> SEQ ID NO 47
<211> LENGTH: 137
<212> TYPE: PRT
<213> ORGANISM: Artificial Sequence
<220> FEATURE:
<223> OTHER INFORMATION: translation of nucleotide sequence of insert in
      pJET1.2 plasmid after primer walking 2 (5a1 smallband insert)

<400> SEQUENCE: 47
```

```
Asn Gln Asp Phe Ala Glu Ala Thr Lys Glu Pro Gly Leu Ala Phe Ala
1               5                  10                  15

Phe Gly Lys Phe Asp Gly Ile Leu Gly Leu Gly Tyr Asp Thr Ile Ser
            20                  25                  30

Val Asn His Ile Thr Pro Pro Phe Tyr Gln Met Met Asn Gln Lys Leu
        35                  40                  45

Val Asp Ser Pro Val Phe Ser Phe Arg Leu Gly Ser Ser Glu Glu Asp
    50                  55                  60

Gly Gly Glu Ala Ile Phe Gly Gly Val Asp Glu Thr Ala Tyr Ser Gly
65                  70                  75                  80

Lys Ile Glu Tyr Val Pro Val Arg Arg Lys Ala Tyr Trp Glu Val Glu
                85                  90                  95

Leu Glu Ser Ile Lys Leu Gly Asp Asp Glu Leu Glu Leu Asp Asn Thr
            100                 105                 110

Gly Ala Ala Ile Asp Thr Gly Thr Ser Leu Ile Ala Leu Pro Ser Asp
        115                 120                 125

Leu Ala Glu Met Leu Asn Val Gln Ile
    130                 135
```

```
<210> SEQ ID NO 48
<211> LENGTH: 904
<212> TYPE: DNA
<213> ORGANISM: Artificial Sequence
<220> FEATURE:
<223> OTHER INFORMATION: nucleotide sequence of insert in pJET1.2
      plasmid after primer walking 2 (5b2 big band insert)

<400> SEQUENCE: 48
```

```
gatttgcaca ttgagcatct ccgccagatc ggaggggaga gcaatcaacg aggttccagt       60
gtcgatggca cgccggtgt tatcgagctc aagctcgtcg tctccgagtt tgatcgactc      120
cagctccacc tcccagtacg ccttcctcct gacagggacg tattcgatct tgccactgta      180
cgcggtctca tcgactcctc cgaagatggc ttcaccaccg tcctcttccg agctaccgag      240
gcggaaagag aacacaggag aatcgacgag cttctggttc atcatctggt agaagggagg      300
agtgatgtgg ttcacggaaa tggtgtcata acccaggccg aggataccat cgaacttgcc      360
aaaggcaaat gcgaggccgg gctccttggt ggcctcagcg aagtcctgat atctttctag      420
aagatctcct acaatattct cagctgccat ggaaaatcga tgttcttctt ttattctctc      480
aagattttca ggctgtatat taaaacttat attaagaact atgctaacca cctcatcagg      540
aaccgttgta ggtggcgtgg gttttcttgg caatcgactc tcatgaaaac tacgagctaa      600
atattcaata tgttcctctt gaccaacttt attctgcatt ttttttgaac gaggtttaga      660
```

```
gcaagcttca ggaaactgag acaggaattt tattaaaaat ttaaattttg aagaaagttc    720
agggttaata gcatccattt tttgctttgc aagttcctca gcattcttaa caaaagacgt    780
ctcttttgac atgtttaaag tttaaacctc ctgtgtgaaa ttattatccg ctcataattc    840
cacacattat acgagccgga agcataaagt gtaaagcctg gggtgcctaa tgagtgagct    900
aact                                                                 904
```

```
<210> SEQ ID NO 49
<211> LENGTH: 137
<212> TYPE: PRT
<213> ORGANISM: Artificial Sequence
<220> FEATURE:
<223> OTHER INFORMATION: translation of nucleotide sequence of insert in
      pJET1.2 plasmid after primer walking 2 (5b2 big band insert)

<400> SEQUENCE: 49
```

Tyr Gln Asp Phe Ala Glu Ala Thr Lys Glu Pro Gly Leu Ala Phe Ala
1               5                   10                  15

Phe Gly Lys Phe Asp Gly Ile Leu Gly Leu Gly Tyr Asp Thr Ile Ser
            20                  25                  30

Val Asn His Ile Thr Pro Pro Phe Tyr Gln Met Met Asn Gln Lys Leu
        35                  40                  45

Val Asp Ser Pro Val Phe Ser Phe Arg Leu Gly Ser Ser Glu Glu Asp
    50                  55                  60

Gly Gly Glu Ala Ile Phe Gly Gly Val Asp Glu Thr Ala Tyr Ser Gly
65                  70                  75                  80

Lys Ile Glu Tyr Val Pro Val Arg Arg Lys Ala Tyr Trp Glu Val Glu
                85                  90                  95

Leu Glu Ser Ile Lys Leu Gly Asp Asp Glu Leu Glu Leu Asp Asn Thr
            100                 105                 110

Gly Ala Ala Ile Asp Thr Gly Thr Ser Leu Ile Ala Leu Pro Ser Asp
        115                 120                 125

Leu Ala Glu Met Leu Asn Val Gln Ile
    130                 135

```
<210> SEQ ID NO 50
<211> LENGTH: 229
<212> TYPE: PRT
<213> ORGANISM: Artificial Sequence
<220> FEATURE:
<223> OTHER INFORMATION: sequence of protein obtained from primer
      walking step 2

<400> SEQUENCE: 50
```

Asn Gln Asp Phe Ala Glu Ala Thr Lys Glu Pro Gly Leu Ala Phe Ala
1               5                   10                  15

Phe Gly Lys Phe Asp Gly Ile Leu Gly Leu Gly Tyr Asp Thr Ile Ser
            20                  25                  30

Val Asn His Ile Thr Pro Pro Phe Tyr Gln Met Met Asn Gln Lys Leu
        35                  40                  45

Val Asp Ser Pro Val Phe Ser Phe Arg Leu Gly Ser Ser Glu Glu Asp
    50                  55                  60

Gly Gly Glu Ala Ile Phe Gly Gly Val Asp Glu Thr Ala Tyr Ser Gly
65                  70                  75                  80

Lys Ile Glu Tyr Val Pro Val Arg Arg Lys Ala Tyr Trp Glu Val Glu
                85                  90                  95

Leu Glu Ser Ile Lys Leu Gly Asp Asp Glu Leu Glu Leu Asp Asn Thr

```
                    100                 105                 110
Gly Ala Ala Ile Asp Thr Gly Thr Ser Leu Ile Ala Leu Pro Ser Asp
            115                 120                 125

Leu Ala Glu Met Leu Asn Val Gln Ile Gly Ala Lys Lys Ser Trp Asn
            130                 135                 140

Gly Gln Tyr Thr Val Asp Cys Ala Lys Val Pro Thr Leu Pro Asp Leu
145                 150                 155                 160

Thr Phe Tyr Phe Ser Gly Lys Pro Tyr Thr Leu Lys Gly Thr Asp Tyr
                    165                 170                 175

Val Leu Glu Val Gln Gly Thr Cys Met Ser Ser Phe Thr Gly Ile Asp
            180                 185                 190

Ile Asn Leu Pro Gly Gly Gly Ala Leu Trp Ile Ile Gly Asp Val Phe
                195                 200                 205

Leu Arg Lys Tyr Tyr Thr Val Tyr Asp His Gly Arg Asp Ala Val Gly
            210                 215                 220

Phe Ala Leu Ala Lys
225

<210> SEQ ID NO 51
<211> LENGTH: 20
<212> TYPE: DNA
<213> ORGANISM: Artificial Sequence
<220> FEATURE:
<223> OTHER INFORMATION: primer walking 3 (PW-3) dengerate forward
      primer 1
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: modified_base
<222> LOCATION: (15)..(15)
<223> OTHER INFORMATION: I
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 51
canarrhtna arytnsanaa                                               20

<210> SEQ ID NO 52
<211> LENGTH: 20
<212> TYPE: DNA
<213> ORGANISM: Artificial Sequence
<220> FEATURE:
<223> OTHER INFORMATION: primer walking 3 (PW-3) dengerate forward
      primer 2
<220> FEATURE:
<221> NAME/KEY: misc_feature
<222> LOCATION: (15)..(15)
<223> OTHER INFORMATION: n is a, c, g, or t

<400> SEQUENCE: 52
aaytwyatga aygcncarta                                               20
```

<210> SEQ ID NO 53
<211> LENGTH: 21
<212> TYPE: DNA
<213> ORGANISM: Artificial Sequence
<220> FEATURE:
<223> OTHER INFORMATION: primer walking 3 (PW-3) dengerate forward primer 3
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: modified_base
<222> LOCATION: (16)..(16)
<223> OTHER INFORMATION: I
<220> FEATURE:
<221> NAME/KEY: misc_feature
<222> LOCATION: (16)..(16)
<223> OTHER INFORMATION: n is a, c, g, or t

<400> SEQUENCE: 53
ttyaargtnr tnyttngaya c                                        21

<210> SEQ ID NO 54
<211> LENGTH: 18
<212> TYPE: DNA
<213> ORGANISM: Artificial Sequence
<220> FEATURE:
<223> OTHER INFORMATION: primer walking 3 (PW-3) definite reverse primer 1

<400> SEQUENCE: 54
gccaaaggca aatgcgag                                            18

<210> SEQ ID NO 55
<211> LENGTH: 16
<212> TYPE: DNA
<213> ORGANISM: Artificial Sequence
<220> FEATURE:
<223> OTHER INFORMATION: primer walking 3 (PW-3) definite reverse primer 1 short sequence

<400> SEQUENCE: 55
gccaaaggca aatgcg                                              16

<210> SEQ ID NO 56
<211> LENGTH: 18
<212> TYPE: DNA
<213> ORGANISM: Artificial Sequence
<220> FEATURE:
<223> OTHER INFORMATION: primer walking 3 (PW-3) definite reverse primer 2

<400> SEQUENCE: 56
caggccgagg ataccatc                                            18

<210> SEQ ID NO 57
<211> LENGTH: 15
<212> TYPE: DNA
<213> ORGANISM: Artificial Sequence
<220> FEATURE:

<223> OTHER INFORMATION: primer walking 3 (PW-3) definite reverse
      primer 2 short

<400> SEQUENCE: 57
caggccgagg atacc                                                    15

<210> SEQ ID NO 58
<211> LENGTH: 17
<212> TYPE: DNA
<213> ORGANISM: Artificial Sequence
<220> FEATURE:
<223> OTHER INFORMATION: primer walking 3 (PW-3) reverse primer 23x

<400> SEQUENCE: 58
catcgaactt gccaaag                                                  17

<210> SEQ ID NO 59
<211> LENGTH: 7
<212> TYPE: PRT
<213> ORGANISM: Artificial Sequence
<220> FEATURE:
<223> OTHER INFORMATION: translation of PW-3 degenerate forward
      primer 1 sequence

<400> SEQUENCE: 59

His Arg Met Lys Leu Glu Lys
1               5

<210> SEQ ID NO 60
<211> LENGTH: 7
<212> TYPE: PRT
<213> ORGANISM: Artificial Sequence
<220> FEATURE:
<223> OTHER INFORMATION: translation of PW-3 dengerate forward primer 2
      sequence

<400> SEQUENCE: 60

Asn Tyr Met Asn Ala Gln Tyr
1               5

<210> SEQ ID NO 61
<211> LENGTH: 7
<212> TYPE: PRT
<213> ORGANISM: Artificial Sequence
<220> FEATURE:
<223> OTHER INFORMATION: translation of PW-3 degenerate forward primer 3
      sequence

<400> SEQUENCE: 61

Phe Lys Val Ile Leu Asp Thr
1               5

<210> SEQ ID NO 62
<211> LENGTH: 6
<212> TYPE: PRT
<213> ORGANISM: Artificial Sequence
<220> FEATURE:
<223> OTHER INFORMATION: translation of PW-3 definite reverse primer 1
      sequence

<400> SEQUENCE: 62

Leu Ala Phe Ala Phe Gly
1               5

<210> SEQ ID NO 63
<211> LENGTH: 6
<212> TYPE: PRT

<213> ORGANISM: Artificial Sequence
<220> FEATURE:
<223> OTHER INFORMATION: translation of PW-3 definite reverse primer 2 sequence

<400> SEQUENCE: 63

Asp Gly Ile Leu Gly Leu
1               5

<210> SEQ ID NO 64
<211> LENGTH: 6
<212> TYPE: PRT
<213> ORGANISM: Artificial Sequence
<220> FEATURE:
<223> OTHER INFORMATION: translation of PW-3 reverse primer 23x sequence
<220> FEATURE:
<221> NAME/KEY: misc_feature
<222> LOCATION: (6)..(6)
<223> OTHER INFORMATION: Xaa can be any naturally occurring amino acid

<400> SEQUENCE: 64

Phe Gly Lys Phe Asp Xaa
1               5

<210> SEQ ID NO 65
<211> LENGTH: 893
<212> TYPE: DNA
<213> ORGANISM: Artificial Sequence
<220> FEATURE:
<223> OTHER INFORMATION: nucleotide sequence of insert in pJET1.2 plasmid after primer walking 3

<400> SEQUENCE: 65

```
catcgaactt gccaaaggca aatgcgaggc cgggctcctt ggtggcctct gcgaaatctt      60
ggttcttgat ggtgatgtca ccgattgtca agacatcttg cgagacgaag ccctccatgg     120
agccagagcc atactggatc gagaactcgg agccgttcgc cttgtatgtc gacgaagcgg     180
tcgagtcata cttggcgtgt aggaagcacg caatggaggt acacttggtg ctcggaaccc     240
agaggttgct cgacccagtg tccaggatga ccttgaacga ttgcggggga gtgcccaagg     300
tgatttcagc gaagtactgt gcattcatga agttatcttt ctagaagatc tcctacaata     360
ttctcagctg ccatggaaaa tcgatgttct tcttttattc tctcaagatt ttcaggctgt     420
atattaaaac ttatattaag aactatgcta accacctcat caggaaccgt tgtaggtggc     480
gtgggttttc ttggcaatcg actctcatga aaactacgag ctaaatattc aatatgttcc     540
tcttgaccaa ctttattctg cattttttt gaacgaggtt tagagcaagc ttcaggaaac     600
tgagacagga atttattaa aaatttaaat tttgaagaaa gttcagggtt aatagcatcc     660
atttttgct ttgcaagttc ctcagcattc ttaacaaaag acgtctcttt tgacatgttt     720
aaagtttaaa cctcctgtgt gaaattatta tccgctcata attccacaca ttatacgagc     780
cggaagcata aagtgtaaag cctggggtgc ctaatgagtg agctaactca cattaattgc     840
gttgcgctca ctgccaattg ctttccagtc gggaaacctg tcgtgccagc tgc            893
```

<210> SEQ ID NO 66
<211> LENGTH: 112
<212> TYPE: PRT
<213> ORGANISM: Artificial Sequence
<220> FEATURE:
<223> OTHER INFORMATION: translation of nucleotide sequence of insert in pJET1.2 plasmid after primer walking 3
<220> FEATURE:
<221> NAME/KEY: misc_feature
<222> LOCATION: (112)..(112)

<223> OTHER INFORMATION: Xaa can be any naturally occurring amino acid

<400> SEQUENCE: 66

Asn Phe Met Asn Ala Gln Tyr Phe Ala Glu Ile Thr Leu Gly Thr Pro
1               5                   10                  15

Pro Gln Ser Phe Lys Val Ile Leu Asp Thr Gly Ser Ser Asn Leu Trp
            20                  25                  30

Val Pro Ser Thr Lys Cys Thr Ser Ile Ala Cys Phe Leu His Ala Lys
        35                  40                  45

Tyr Asp Ser Thr Ala Ser Ser Thr Tyr Lys Ala Asn Gly Ser Glu Phe
    50                  55                  60

Ser Ile Gln Tyr Gly Ser Gly Ser Met Glu Gly Phe Val Ser Gln Asp
65                  70                  75                  80

Val Leu Thr Ile Gly Asp Ile Thr Ile Lys Asn Gln Asp Phe Ala Glu
                85                  90                  95

Ala Thr Lys Glu Pro Gly Leu Ala Phe Ala Phe Gly Lys Phe Asp Xaa
            100                 105                 110

<210> SEQ ID NO 67
<211> LENGTH: 112
<212> TYPE: PRT
<213> ORGANISM: Artificial Sequence
<220> FEATURE:
<223> OTHER INFORMATION: sequence of protein obtained from primer
      walking step 3
<220> FEATURE:
<221> NAME/KEY: misc_feature
<222> LOCATION: (112)..(112)
<223> OTHER INFORMATION: Xaa can be any naturally occurring amino acid

<400> SEQUENCE: 67

Asn Phe Met Asn Ala Gln Tyr Phe Ala Glu Ile Thr Leu Gly Thr Pro
1               5                   10                  15

Pro Gln Ser Phe Lys Val Ile Leu Asp Thr Gly Ser Ser Asn Leu Trp
            20                  25                  30

Val Pro Ser Thr Lys Cys Thr Ser Ile Ala Cys Phe Leu His Ala Lys
        35                  40                  45

Tyr Asp Ser Thr Ala Ser Ser Thr Tyr Lys Ala Asn Gly Ser Glu Phe
    50                  55                  60

Ser Ile Gln Tyr Gly Ser Gly Ser Met Glu Gly Phe Val Ser Gln Asp
65                  70                  75                  80

Val Leu Thr Ile Gly Asp Ile Thr Ile Lys Asn Gln Asp Phe Ala Glu
                85                  90                  95

Ala Thr Lys Glu Pro Gly Leu Ala Phe Ala Phe Gly Lys Phe Asp Xaa
            100                 105                 110

<210> SEQ ID NO 68
<211> LENGTH: 319
<212> TYPE: PRT
<213> ORGANISM: Artificial Sequence
<220> FEATURE:
<223> OTHER INFORMATION: sequence of protein after primer walking step 3

<400> SEQUENCE: 68

Asn Phe Met Asn Ala Gln Tyr Phe Ala Glu Ile Thr Leu Gly Thr Pro
1               5                   10                  15

Pro Gln Ser Phe Lys Val Ile Leu Asp Thr Gly Ser Ser Asn Leu Trp
            20                  25                  30

Val Pro Ser Thr Lys Cys Thr Ser Ile Ala Cys Phe Leu His Ala Lys
        35                  40                  45

Tyr Asp Ser Thr Ala Ser Ser Thr Tyr Lys Ala Asn Gly Ser Glu Phe
 50                  55                  60

Ser Ile Gln Tyr Gly Ser Gly Ser Met Glu Gly Phe Val Ser Gln Asp
 65                  70                  75                  80

Val Leu Thr Ile Gly Asp Ile Thr Ile Lys Asn Gln Asp Phe Ala Glu
                 85                  90                  95

Ala Thr Lys Glu Pro Gly Leu Ala Phe Ala Phe Gly Lys Phe Asp Gly
             100                 105                 110

Ile Leu Gly Leu Gly Tyr Asp Thr Ile Ser Val Asn His Ile Thr Pro
         115                 120                 125

Pro Phe Tyr Gln Met Met Asn Gln Lys Leu Val Asp Ser Pro Val Phe
     130                 135                 140

Ser Phe Arg Leu Gly Ser Ser Glu Glu Asp Gly Gly Glu Ala Ile Phe
145                 150                 155                 160

Gly Gly Val Asp Glu Thr Ala Tyr Ser Gly Lys Ile Glu Tyr Val Pro
                165                 170                 175

Val Arg Arg Lys Ala Tyr Trp Glu Val Glu Leu Glu Ser Ile Lys Leu
            180                 185                 190

Gly Asp Asp Glu Leu Glu Leu Asp Asn Thr Gly Ala Ala Ile Asp Thr
        195                 200                 205

Gly Thr Ser Leu Ile Ala Leu Pro Ser Asp Leu Ala Glu Met Leu Asn
    210                 215                 220

Val Gln Ile Gly Ala Lys Lys Ser Trp Asn Gly Gln Tyr Thr Val Asp
225                 230                 235                 240

Cys Ala Lys Val Pro Thr Leu Pro Asp Leu Thr Phe Tyr Phe Ser Gly
                245                 250                 255

Lys Pro Tyr Thr Leu Lys Gly Thr Asp Tyr Val Leu Glu Val Gln Gly
            260                 265                 270

Thr Cys Met Ser Ser Phe Thr Gly Ile Asp Ile Asn Leu Pro Gly Gly
        275                 280                 285

Gly Ala Leu Trp Ile Ile Gly Asp Val Phe Leu Arg Lys Tyr Tyr Thr
    290                 295                 300

Val Tyr Asp His Gly Arg Asp Ala Val Gly Phe Ala Leu Ala Lys
305                 310                 315

<210> SEQ ID NO 69
<211> LENGTH: 18
<212> TYPE: DNA
<213> ORGANISM: Artificial Sequence
<220> FEATURE:
<223> OTHER INFORMATION: target specific primer TSP1.3

<400> SEQUENCE: 69
cccagtgtcc aggatgac                                                 18

<210> SEQ ID NO 70
<211> LENGTH: 18
<212> TYPE: DNA
<213> ORGANISM: Artificial Sequence
<220> FEATURE:
<223> OTHER INFORMATION: target specific primer TSP1.2

<400> SEQUENCE: 70
accttgaacg attgcggg                                                 18

<210> SEQ ID NO 71
<211> LENGTH: 17

```
<212> TYPE: DNA
<213> ORGANISM: Artificial Sequence
<220> FEATURE:
<223> OTHER INFORMATION: target specific primer TSP1.1

<400> SEQUENCE: 71
gggagtgccc aaggtga                                                17

<210> SEQ ID NO 72
<211> LENGTH: 19
<212> TYPE: DNA
<213> ORGANISM: Artificial Sequence
<220> FEATURE:
<223> OTHER INFORMATION: target specific primer TSP2

<400> SEQUENCE: 72
gagtgcccaa ggtgatttc                                              19

<210> SEQ ID NO 73
<211> LENGTH: 20
<212> TYPE: DNA
<213> ORGANISM: Artificial Sequence
<220> FEATURE:
<223> OTHER INFORMATION: target specific primer TSP3

<400> SEQUENCE: 73
ggtgatttca gcgaagtact                                             20

<210> SEQ ID NO 74
<211> LENGTH: 894
<212> TYPE: DNA
<213> ORGANISM: Artificial Sequence
<220> FEATURE:
<223> OTHER INFORMATION: nucleotide sequence of insert in pJET1.2
      plasmid after primer walking 4 (4-1-1-3-forward insert)

<400> SEQUENCE: 74
gatgagttta ggtccagcgt ccgtgggggg ggcgtgcgga cggatctgcg agcggaacat    60
atcctccgcc atatgggagc tttcttcgtc ttgagagctg tacattatcc actccagctc   120
ctgcaacttc gccccccgcca aaaaaaaaaa aaaaaaaac atgtcggccg cctcggcctc   180
tagaatgggg aagcagtggt atcaacgcag agtggaagca gtggtatcaa cgcagagtgg   240
ccattacggc cgggaagcag tggtatcaac gcagagtggc cattacgaag cagtggtata   300
aacgcagagt ggccattaag cagtggtatc aacgcagagt gaccatgata ctctccagat   360 tcgccccct cgccctgctc ccttcgtgg ccgccgacgg cgtccacaag ctgaagctca   420
ccaagcttcc tcccgcaact tccaacccgt tgttggagag tgcttacctg gctgagaagt   480
atggtggtgg ttcccagatg ccccttagcg cgggcattgg ccgcaacgtc cgcgtgtcgc   540
gcccgaccgt caaggacggc gaggagctct tctggactca ggacgagttt tcgaccgagg   600
gcggtcacaa cgttcccttg agtaacttca tgaacgctca gtacttcgct gaaatcacca   660
tctttctaga agatctccta caatattctc agctgccatg gaaaatcgat gttcttcttt   720
tattctctca agattttcag gctgtatatt aaaacttata ttaagaacta tgctaaccac   780
ctcatcagga accgttgtag gtggcgtggg ttttcttggc aatcgactct catgaaaact   840
acgagctaaa tattcaatat gttcctcttg accaacttta ttctgcattt tttt          894

<210> SEQ ID NO 75
<211> LENGTH: 217
<212> TYPE: PRT
<213> ORGANISM: Artificial Sequence
```

<220> FEATURE:
<223> OTHER INFORMATION: translation of nucleotide sequence of insert in
      pJET1.2 plasmid after primer walking 4 (4-1-1-3-forward insert)

<400> SEQUENCE: 75

Val Val Gln Arg Pro Trp Gly Gly Arg Ala Asp Gly Ser Ala Ser Gly
1               5                   10                  15

Thr Tyr Pro Pro Pro Tyr Gly Ser Phe Leu Arg Leu Glu Ser Cys Thr
            20                  25                  30

Leu Ser Thr Pro Ala Pro Ala Thr Ser Pro Pro Lys Lys Lys Lys
        35                  40                  45

Lys Lys Thr Cys Arg Pro Pro Arg Pro Leu Glu Trp Gly Ser Ser Gly
    50                  55                  60

Ile Asn Ala Glu Trp Lys Gln Trp Tyr Gln Arg Val Ala Ile Thr
65                  70                  75                  80

Ala Gly Lys Gln Trp Tyr Gln Arg Val Ala Ile Thr Lys Gln Trp
                85                  90                  95

Tyr Lys Arg Arg Val Ala Ile Lys Gln Trp Tyr Gln Arg Val Thr
                100                 105                 110

Met Ile Leu Ser Arg Phe Ala Pro Leu Ala Leu Pro Phe Val Ala
            115                 120                 125

Ala Asp Gly Val His Lys Leu Lys Leu Thr Lys Leu Pro Pro Ala Thr
            130                 135                 140

Ser Asn Pro Leu Leu Glu Ser Ala Tyr Leu Ala Glu Lys Tyr Gly Gly
145                 150                 155                 160

Gly Ser Gln Met Pro Leu Ser Ala Gly Ile Gly Arg Asn Val Arg Val
                165                 170                 175

Ser Arg Pro Thr Val Lys Asp Gly Glu Glu Leu Phe Trp Thr Gln Asp
                180                 185                 190

Glu Phe Ser Thr Glu Gly Gly His Asn Val Pro Leu Ser Asn Phe Met
            195                 200                 205

Asn Ala Gln Tyr Phe Ala Glu Ile Thr
        210                 215

<210> SEQ ID NO 76
<211> LENGTH: 914
<212> TYPE: DNA
<213> ORGANISM: Artificial Sequence
<220> FEATURE:
<223> OTHER INFORMATION: nucleotide sequence of insert in pJET1.2
      plasmid after primer walking 4 (4-1-1-3-reverse insert)

<400> SEQUENCE: 76
ggtgatttca gcgaagtact gagcgttcat gaagttactc aagggaacgt tgtgaccgcc      60
ctcggtcgaa aactcgtcct gagtccagaa gagctcctcg ccgtccttga cggtcgggcg     120
cgacacgcgg acgttgcggc caatgcccgc gctaaggggc atctgggaac caccaccata     180
cttctcagcc aggtaagcac tctccaacaa cgggttggaa gttgcggag gaagcttggt      240 gagcttcagc ttgtggacgc cgtcggcggc cacgaagggg agcagggcga ggggggcgaa     300
tctggagagt atcatggtca ctctgcgttg ataccactgc ttaatggcca ctctgcgttt     360
ataccactgc ttcgtaatgg ccactctgcg ttgataccac tgcttcccgg ccgtaatggc     420
cactctgcgt tgataccact gcttccactc tgcgttgata ccactgcttc cccattctag     480
aggccgaggc ggccgacatg ttttttttt tttttttttt ggcgggggcg aagttgcagg     540
agctggagtg gataatgtac agctctcaag acgaagaaag ctcccatatg gcggaggata     600

```
tgttccgctc gcagatccgt ccgcacgccc cccccacgga cgctggacct aaactcatct    660
tgctgaaaaa ctcgagccat ccggaagatc tggcggccgc tctccctata gtgagtcgta    720
ttacgccgga tggatatggt gttcaggcac aagtgttaaa gcagttgatt ttattcacta    780
tgatgaaaaa aacaatgaat ggaacctgct ccaagttaaa atagagataa taccgaaaac    840
tcatcgagta gtaagattag agataataca acaataaaaa atggtttaga acttactcac    900
agcgtgatgc tact                                                      914
```

<210> SEQ ID NO 77
<211> LENGTH: 217
<212> TYPE: PRT
<213> ORGANISM: Artificial Sequence
<220> FEATURE:
<223> OTHER INFORMATION: translation of nucleotide sequence of insert in
      pJET1.2 plasmid after primer walking 4 (4-1-1-3-reverse insert)

<400> SEQUENCE: 77

```
Val Val Gln Arg Pro Trp Gly Gly Arg Ala Asp Gly Ser Ala Ser Gly
1               5                   10                  15

Thr Tyr Pro Pro Pro Tyr Gly Ser Phe Leu Arg Leu Glu Ser Cys Thr
            20                  25                  30

Leu Ser Thr Pro Ala Pro Ala Thr Ser Pro Pro Lys Lys Lys
        35                  40                  45

Lys Lys Thr Cys Arg Pro Arg Pro Leu Glu Trp Gly Ser Ser Gly
50                  55                  60

Ile Asn Ala Glu Trp Lys Gln Trp Tyr Gln Arg Val Ala Ile Thr
65                  70                  75                  80

Ala Gly Lys Gln Trp Tyr Gln Arg Val Ala Ile Thr Lys Gln Trp
                85                  90                  95

Tyr Lys Arg Arg Val Ala Ile Lys Gln Trp Tyr Gln Arg Val Thr
                100                 105                 110

Met Ile Leu Ser Arg Phe Ala Pro Leu Ala Leu Pro Phe Val Ala
            115                 120                 125

Ala Asp Gly Val His Lys Leu Lys Leu Thr Lys Leu Pro Pro Ala Thr
130                 135                 140

Ser Asn Pro Leu Leu Glu Ser Ala Tyr Leu Ala Glu Lys Tyr Gly Gly
145                 150                 155                 160

Gly Ser Gln Met Pro Leu Ser Ala Gly Ile Gly Arg Asn Val Arg Val
                165                 170                 175

Ser Arg Pro Thr Val Lys Asp Gly Glu Glu Leu Phe Trp Thr Gln Asp
            180                 185                 190

Glu Phe Ser Thr Glu Gly Gly His Asn Val Pro Leu Ser Asn Phe Met
        195                 200                 205

Asn Ala Gln Tyr Phe Ala Glu Ile Thr
    210                 215
```

<210> SEQ ID NO 78
<211> LENGTH: 21
<212> TYPE: DNA
<213> ORGANISM: Artificial Sequence
<220> FEATURE:
<223> OTHER INFORMATION: universal primer

<400> SEQUENCE: 78

```
gagtttaggt ccagcgtccg t                                              21
```

<210> SEQ ID NO 79

<211> LENGTH: 21
<212> TYPE: DNA
<213> ORGANISM: Artificial Sequence
<220> FEATURE:
<223> OTHER INFORMATION: reverse complement of universal primer

<400> SEQUENCE: 79
acggacgctg gacctaaact c        21

<210> SEQ ID NO 80
<211> LENGTH: 20
<212> TYPE: DNA
<213> ORGANISM: Artificial Sequence
<220> FEATURE:
<223> OTHER INFORMATION: reverse complement of target specific primer
      TSP3

<400> SEQUENCE: 80
agtacttcgc tgaaatcacc        20

<210> SEQ ID NO 81
<211> LENGTH: 412
<212> TYPE: PRT
<213> ORGANISM: Artificial Sequence
<220> FEATURE:
<223> OTHER INFORMATION: protein sequence after primer walking step 4

<400> SEQUENCE: 81

Met Ile Leu Ser Arg Phe Ala Pro Leu Ala Leu Pro Phe Val Ala
1               5                   10                  15

Ala Asp Gly Val His Lys Leu Lys Leu Thr Lys Leu Pro Pro Ala Thr
            20                  25                  30

Ser Asn Pro Leu Leu Glu Ser Ala Tyr Leu Ala Glu Lys Tyr Gly Gly
        35                  40                  45

Gly Ser Gln Met Pro Leu Ser Ala Gly Ile Gly Arg Asn Val Arg Val
    50                  55                  60

Ser Arg Pro Thr Val Lys Asp Gly Glu Glu Leu Phe Trp Thr Gln Asp
65                  70                  75                  80

Glu Phe Ser Thr Glu Gly Gly His Asn Val Pro Leu Ser Asn Phe Met
                85                  90                  95

Asn Ala Gln Tyr Phe Ala Glu Ile Thr Leu Gly Thr Pro Pro Gln Ser
            100                 105                 110

Phe Lys Val Ile Leu Asp Thr Gly Ser Ser Asn Leu Trp Val Pro Ser
        115                 120                 125

Thr Lys Cys Thr Ser Ile Ala Cys Phe Leu His Ala Lys Tyr Asp Ser
    130                 135                 140

Thr Ala Ser Ser Thr Tyr Lys Ala Asn Gly Ser Glu Phe Ser Ile Gln
145                 150                 155                 160

Tyr Gly Ser Gly Ser Met Glu Gly Phe Val Ser Gln Asp Val Leu Thr
                165                 170                 175

Ile Gly Asp Ile Thr Ile Lys Asn Gln Asp Phe Ala Glu Ala Thr Lys
            180                 185                 190

Glu Pro Gly Leu Ala Phe Ala Phe Gly Lys Phe Asp Gly Ile Leu Gly
        195                 200                 205

Leu Gly Tyr Asp Thr Ile Ser Val Asn His Ile Thr Pro Pro Phe Tyr
    210                 215                 220

Gln Met Met Asn Gln Lys Leu Val Asp Ser Pro Val Phe Ser Phe Arg
225                 230                 235                 240

Leu Gly Ser Ser Glu Glu Asp Gly Gly Glu Ala Ile Phe Gly Gly Val

```
                        245                 250                 255
Asp Glu Thr Ala Tyr Ser Gly Lys Ile Glu Tyr Val Pro Val Arg Arg
                260                 265                 270

Lys Ala Tyr Trp Glu Val Glu Leu Glu Ser Ile Lys Leu Gly Asp Asp
            275                 280                 285

Glu Leu Glu Leu Asp Asn Thr Gly Ala Ala Ile Asp Thr Gly Thr Ser
        290                 295                 300

Leu Ile Ala Leu Pro Ser Asp Leu Ala Glu Met Leu Asn Val Gln Ile
305                 310                 315                 320

Gly Ala Lys Lys Ser Trp Asn Gly Gln Tyr Thr Val Asp Cys Ala Lys
                325                 330                 335

Val Pro Thr Leu Pro Asp Leu Thr Phe Tyr Phe Ser Gly Lys Pro Tyr
            340                 345                 350

Thr Leu Lys Gly Thr Asp Tyr Val Leu Glu Val Gln Gly Thr Cys Met
        355                 360                 365

Ser Ser Phe Thr Gly Ile Asp Ile Asn Leu Pro Gly Gly Gly Ala Leu
    370                 375                 380

Trp Ile Ile Gly Asp Val Phe Leu Arg Lys Tyr Tyr Thr Val Tyr Asp
385                 390                 395                 400

His Gly Arg Asp Ala Val Gly Phe Ala Leu Ala Lys
                405                 410

<210> SEQ ID NO 82
<211> LENGTH: 32
<212> TYPE: DNA
<213> ORGANISM: Artificial Sequence
<220> FEATURE:
<223> OTHER INFORMATION: forward primer with NdeI site

<400> SEQUENCE: 82
aattacatat gatactctcc agattcgccc cc                                    32

<210> SEQ ID NO 83
<211> LENGTH: 31
<212> TYPE: DNA
<213> ORGANISM: Artificial Sequence
<220> FEATURE:
<223> OTHER INFORMATION: reverse primer with XhoI site

<400> SEQUENCE: 83
aattctcgag tcacttggca agagcgaagc c                                     31

<210> SEQ ID NO 84
<211> LENGTH: 244
<212> TYPE: PRT
<213> ORGANISM: Cryptococcus neoformans

<400> SEQUENCE: 84

Met Lys Thr Ser Ala Ile Leu Ile Ala Ala Leu Ser Ala Ala Ala Ser
1               5                   10                  15

Val Glu Ala Gly Ile His Arg Met Lys Leu Glu Lys Gln Thr Pro Ser
            20                  25                  30

Ser Thr Ser Leu Thr Gly Thr Phe Pro Pro Ser Pro Glu Leu Glu Ala
        35                  40                  45

Lys Trp Leu Ala Ser Lys Tyr Leu Gly Gln Glu Tyr Thr Asp Gln Met
    50                  55                  60

Pro Leu Gly Gly Phe Gly Gly Ala Gly Lys Lys Phe Lys Ser Gly Asn
65                  70                  75                  80
```

```
Lys His Thr Glu His Pro Glu Gln Asn Asp Glu Arg Tyr Trp Ala
                85                  90                  95
Gln Met Val Asp Gln Ser Ala His Ser Gln Met Ile Asp Val Leu Lys
            100                 105                 110
Gly Gly His Gly Val Pro Leu Ser Asn Tyr Met Asn Ala Gln Tyr Phe
            115                 120                 125
Ala Thr Met Glu Ile Gly Thr Pro Phe Gln Thr Phe Lys Val Ile Leu
            130                 135                 140
Asp Thr Gly Ser Ser Asn Leu Trp Val Pro Ser Val Lys Cys Thr Ser
145                 150                 155                 160
Ile Ala Cys Phe Leu His Ser Lys Tyr Asp Ser Ser Gln Ser Ser Thr
                165                 170                 175
Tyr Lys Ala Asn Gly Ser Asp Phe Glu Ile His Tyr Gly Ser Gly Ser
            180                 185                 190
Leu Glu Gly Phe Ile Ser Gln Asp Thr Val Ser Ile Gly Asp Leu Val
            195                 200                 205
Val Lys Lys Gln Asp Phe Ala Glu Ala Thr Lys Glu Pro Gly Leu Ala
            210                 215                 220
Phe Ala Phe Gly Lys Phe Asp Gly Ile Leu Gly Leu Gly Tyr Asp Thr
225                 230                 235                 240
Ile Ser Val Asn

<210> SEQ ID NO 85
<211> LENGTH: 238
<212> TYPE: PRT
<213> ORGANISM: Cryptococcus gattii

<400> SEQUENCE: 85

Met Lys Thr Ser Ala Ile Leu Ile Ala Ala Leu Ser Ala Ala Ala Ser
1               5                   10                  15
Val Glu Ala Gly Ile His Arg Met Lys Leu Glu Lys Gln Ser Leu Ser
            20                  25                  30
Ser Thr Ser Leu Thr Gly Asp Ile Pro Thr Phe Tyr Pro Ser Pro Glu
        35                  40                  45
Leu Glu Ala Lys Trp Leu Ala Ser Lys Tyr Leu Gly Gln Asp Tyr Ala
    50                  55                  60
Lys Gln Met Pro Leu Met Gly Phe Asp Gly Ala Gly Lys Lys Phe Lys
65                  70                  75                  80
Ser Gly Asn Glu His Thr Glu His His Glu Gln Lys Asp Gln Asp Arg
                85                  90                  95
Tyr Trp Ala Gln Met Val Asp Met Leu Lys Asp Gly His Gly Val Pro
            100                 105                 110
Leu Ser Asn Tyr Met Asn Ala Gln Tyr Phe Ala Gln Ile Glu Leu Gly
            115                 120                 125
Thr Pro Ala Gln Thr Phe Lys Val Ile Leu Asp Thr Gly Ser Ser Asn
            130                 135                 140
Leu Trp Val Pro Ser Val Gly Cys Thr Ser Ile Ala Cys Phe Leu His
145                 150                 155                 160
Ser Lys Tyr Asp Ser Ser Gln Ser Ser Thr Tyr Lys Ala Asn Gly Ser
                165                 170                 175
Asp Phe Glu Ile His Tyr Gly Ser Gly Ser Leu Glu Gly Phe Ile Ser
            180                 185                 190
Gln Asp Thr Leu Ala Ile Gly Asp Leu Ala Ile Lys Gly Gln Asp Phe
            195                 200                 205
```

```
Ala Glu Ala Thr Lys Glu Pro Gly Leu Ala Phe Ala Phe Gly Lys Phe
    210                 215                 220

Asp Gly Ile Leu Gly Leu Ala Tyr Asp Thr Ile Ser Val Asn
225                 230                 235
```

<210> SEQ ID NO 86
<211> LENGTH: 213
<212> TYPE: PRT
<213> ORGANISM: Laccaria bicolor

<400> SEQUENCE: 86

```
Met Ile Phe Leu Pro Leu Ala Leu Ala Leu Leu Ser Phe Ala Glu Ala
1               5                   10                  15

Ser Arg Ile His Lys Leu Lys Leu His Lys Leu Pro Thr Thr Ser
            20                  25                  30

Asn Gln Phe Glu Ser Ala Tyr Leu Ala Glu Lys Tyr Gly Ala Ser Gly
        35                  40                  45

Ser Gln Pro Gln Met Pro Leu Leu Gly Val Gly Thr Gly Arg Arg
    50                  55                  60

Val Ala Met Gln Asn Gly Glu Pro Leu Phe Trp Thr Gln Asp Glu Leu
65                  70                  75                  80

Lys Gly Gly His Ser Val Pro Leu Ser Asn Phe Met Asn Ala Gln Tyr
                85                  90                  95

Phe Thr Glu Ile Ser Ile Gly Asn Pro Pro Gln Ser Phe Lys Val Ile
            100                 105                 110

Leu Asp Thr Gly Ser Ser Asn Leu Trp Val Pro Ser Val Lys Cys Thr
        115                 120                 125

Ser Ile Ala Cys Phe Leu His Thr Lys Tyr Asp Ser Ala Ser Ser Ser
    130                 135                 140

Thr Phe Lys Ala Asn Gly Ser Glu Phe Ser Ile His Tyr Gly Ser Gly
145                 150                 155                 160

Ser Met Glu Gly Phe Val Ser Asn Asp Leu Leu Ser Ile Gly Asp Ile
                165                 170                 175

Thr Ile Lys Gly Gln Asp Phe Ala Glu Ala Val Lys Glu Pro Gly Leu
            180                 185                 190

Ala Phe Ala Phe Gly Lys Phe Asp Gly Ile Leu Gly Leu Gly Tyr Asp
        195                 200                 205

Thr Ile Ser Val Asn
    210
```

<210> SEQ ID NO 87
<211> LENGTH: 219
<212> TYPE: PRT
<213> ORGANISM: Serpula lacrymans

<400> SEQUENCE: 87

```
Met Leu Leu Ser Ala Phe Ala Pro Leu Leu Leu Pro Tyr Ala Ala
1               5                   10                  15

Ala Ala Gly Gly Val His Lys Leu Leu His Lys Leu Pro Lys Val
            20                  25                  30

Ser Pro Asn His Gly Leu Glu Ser Ala Tyr Leu Ala Glu Lys Tyr Gly
        35                  40                  45

Ala Glu Thr Thr Tyr Gln Gln Leu Pro Leu Met Gly Ala Gly Gly Ala
    50                  55                  60

Gly Arg His Ile Arg Pro Asp Arg Pro Glu Asp Ser Asp Leu Phe Trp
65                  70                  75                  80
```

-continued

```
Thr Gln Glu Glu Leu Val Lys Gly Gly His Gly Val Pro Leu Thr Asn
                85                  90                  95

Phe Met Asn Ala Gln Tyr Tyr Thr Glu Ile Thr Leu Gly Ser Pro Ala
            100                 105                 110

Gln Thr Phe Lys Val Ile Leu Asp Thr Gly Ser Ser Asn Leu Trp Val
        115                 120                 125

Pro Ser Ser Lys Cys Thr Ser Ile Ala Cys Phe Leu His Thr Lys Tyr
    130                 135                 140

Asp Ser Ser Ser Ser Thr Tyr Lys Ala Asn Gly Thr Glu Phe Ser
145                 150                 155                 160

Ile Gln Tyr Gly Ser Gly Ser Met Glu Gly Phe Val Ser Gln Glu Ser
                165                 170                 175

Met Lys Ile Gly Asp Leu Ser Ile Gln His Gln Asp Phe Ala Glu Ala
            180                 185                 190

Thr Lys Glu Pro Gly Leu Ala Phe Ala Phe Gly Lys Phe Asp Gly Ile
        195                 200                 205

Leu Gly Leu Gly Tyr Asp Thr Ile Ser Val Asn
    210                 215

<210> SEQ ID NO 88
<211> LENGTH: 212
<212> TYPE: PRT
<213> ORGANISM: Schizophyllum commune

<400> SEQUENCE: 88

Met Ile Leu Thr Ser Leu Phe Leu Gly Leu Leu Pro Ala Val Tyr Ala
1               5                   10                  15

Glu Val His Lys Leu Gln Leu Gln Lys Ile Pro Ala Thr Val Gly Asn
            20                  25                  30

Pro Glu Leu Glu Ser Leu His Leu Ala Glu Lys Tyr Gly Val Val Asn
        35                  40                  45

Glu Phe Gln Thr Pro Leu Met Gly Ala Gly Ala Gly Arg Arg Leu
    50                  55                  60

Lys Asn Asp Ala Gly Glu Asp Leu Phe Trp Thr Gln Glu Gln Val Lys
65                  70                  75                  80

Gly Gly His Gly Val Pro Leu Thr Asn Phe Met Asn Ala Gln Tyr Phe
                85                  90                  95

Thr Glu Ile Thr Leu Gly Thr Pro Pro Gln Asn Phe Lys Val Ile Leu
            100                 105                 110

Asp Thr Gly Ser Ser Asn Leu Trp Val Pro Ser Ser Lys Cys Thr Ser
        115                 120                 125

Ile Ala Cys Phe Leu His Ala Lys Tyr Asp Ser Ser Ala Ser Ser Thr
    130                 135                 140

Tyr Lys Gln Asn Gly Thr Glu Phe Ser Ile Gln Tyr Gly Ser Gly Ser
145                 150                 155                 160

Met Glu Gly Phe Val Ser Gln Asp Val Leu Thr Ile Gly Asp Leu Thr
                165                 170                 175

Ile Pro Gly Gln Asp Phe Ala Glu Ala Val Lys Glu Pro Gly Leu Thr
            180                 185                 190

Phe Ala Phe Gly Lys Phe Asp Gly Ile Leu Gly Leu Gly Tyr Asp Thr
        195                 200                 205

Ile Ser Val Asn
    210

<210> SEQ ID NO 89
```

```
<211> LENGTH: 216
<212> TYPE: PRT
<213> ORGANISM: Coprinus cinereus

<400> SEQUENCE: 89

Met Leu Leu Thr Pro Ile Val Leu Ser Leu Leu Pro Phe Thr Val Ala
1               5                   10                  15

Ala Arg Val His Lys Leu Lys Leu His Lys Val Ala Pro Thr Ala Ser
            20                  25                  30

Asn Pro Asp Phe Glu Val Ala Tyr Leu Ser Gln Lys Tyr Gly Ser Ser
        35                  40                  45

Ala Ser Val Gln Leu Pro Leu Met Gly Ala Gly Gly Ala Ala Arg Arg
    50                  55                  60

Val Ala Arg Pro Asp Ser Arg Asp Gly Glu Gln Leu Phe Trp Thr Gln
65                  70                  75                  80

Asp Asp Leu Lys Asn Gly His Lys Val Pro Leu Thr Asn Phe Met Asn
                85                  90                  95

Ala Gln Tyr Tyr Thr Glu Ile Thr Leu Gly Thr Pro Pro Gln Thr Phe
            100                 105                 110

Lys Val Ile Leu Asp Thr Gly Ser Ser Asn Leu Trp Val Pro Ser Ile
        115                 120                 125

Lys Cys Thr Ser Ile Ala Cys Phe Leu His Thr Lys Tyr Asp Ser Ser
    130                 135                 140

Gln Ser Thr Thr Tyr Lys Ala Asn Gly Thr Glu Phe Ser Ile Gln Tyr
145                 150                 155                 160

Gly Ser Gly Ser Met Glu Gly Phe Val Ser Gln Asp Thr Leu Gly Ile
                165                 170                 175

Gly Asp Leu Thr Ile Lys Gly Gln Asp Phe Ala Glu Ala Leu Lys Glu
            180                 185                 190

Pro Gly Leu Ala Phe Ala Phe Gly Lys Phe Asp Gly Ile Leu Gly Leu
        195                 200                 205

Ala Tyr Asp Thr Ile Ser Val Asn
    210                 215

<210> SEQ ID NO 90
<211> LENGTH: 224
<212> TYPE: PRT
<213> ORGANISM: Ustilago maydis

<400> SEQUENCE: 90

Met Lys Leu Asn Leu Ser Leu Thr Phe Val Thr Ala Leu Ala Thr Ala
1               5                   10                  15

Phe Ala Gly Val Glu Ala Gly Val His Lys Ala Lys Leu Gln Lys Val
            20                  25                  30

Thr Pro Ser Arg Glu Leu Thr Leu Glu Gly Leu Ala Ala Gln Ala Glu
        35                  40                  45

Ile Leu Gln Leu Lys Tyr Gly Gly Ser Ser Lys Lys Gln Val Pro
    50                  55                  60

Phe Ser Ser Asn Pro Glu His Asp Phe Ser Ile Gln Pro Ile Ala Asp
65                  70                  75                  80

Ser Ser Gln Ala Ala Ala Trp Tyr Ala Glu Ala Lys Lys Gly His Gly
                85                  90                  95

Val Pro Leu Thr Asp Phe Leu Asn Ala Gln Tyr Phe Cys Asp Ile Ser
            100                 105                 110

Leu Gly Thr Pro Ala Gln Asp Phe Lys Val Ile Leu Asp Thr Gly Ser
        115                 120                 125
```

```
Ser Asn Leu Trp Val Pro Ser Thr Lys Cys Ser Ser Ile Ala Cys Phe
    130                 135                 140

Leu His Lys Lys Tyr Asp Ser Ser Ala Ser Ser Ser Tyr Lys Lys Asn
145                 150                 155                 160

Gly Thr Glu Phe Lys Ile Gln Tyr Gly Ser Gly Ser Met Glu Gly Ile
                165                 170                 175

Val Ser Asn Asp Val Leu Lys Ile Gly Asp Leu Thr Ile Lys Gly Gln
            180                 185                 190

Asp Phe Ala Glu Ala Thr Ser Glu Pro Gly Leu Ala Phe Ala Phe Gly
        195                 200                 205

Lys Phe Asp Gly Ile Leu Gly Leu Ala Tyr Asp Thr Ile Ser Val Asn
210                 215                 220

<210> SEQ ID NO 91
<211> LENGTH: 202
<212> TYPE: PRT
<213> ORGANISM: Metarhizium anisopliae

<400> SEQUENCE: 91

Met Lys Ser Ala Leu Ile Ala Ala Ala Leu Ala Gly Thr Ala His
1               5                   10                  15

Ala Gly Val His Lys Met Lys Leu Gln Lys Ile Ser Leu Glu Glu Gln
                20                  25                  30

Leu Ala Gly Ala Ser Ile Glu Gln His Val Arg Ala Leu Gly Gln Lys
            35                  40                  45

Tyr Leu Gly Ala Arg Pro Ala Ser Arg Ala Ser Val Met Phe Asn Thr
50                  55                  60

Lys Ala Pro Gln Val Ala Glu Gly His Pro Val Pro Val Ser Asn Phe
65                  70                  75                  80

Met Asn Ala Gln Tyr Phe Ser Glu Ile Thr Val Gly Thr Pro Pro Gln
                85                  90                  95

Thr Phe Lys Val Val Leu Asp Thr Gly Ser Ser Asn Leu Trp Val Pro
            100                 105                 110

Ser Gln Ser Cys Ser Ser Ile Ala Cys Tyr Leu His Ser Thr Tyr Asp
        115                 120                 125

Ser Ser Ser Ser Ser Thr Tyr Lys Lys Asn Gly Ser Ser Phe Glu Ile
130                 135                 140

Arg Tyr Gly Ser Gly Ser Leu Ser Gly Phe Val Ser Gln Asp Val Val
145                 150                 155                 160

Thr Ile Gly Asp Leu Lys Ile Lys Asp Gln Asp Phe Ala Glu Ala Thr
                165                 170                 175

Ser Glu Pro Gly Leu Ala Phe Ala Phe Gly Lys Phe Asp Gly Ile Leu
            180                 185                 190

Gly Leu Gly Tyr Asp Thr Leu Ser Val Asn
        195                 200

<210> SEQ ID NO 92
<211> LENGTH: 202
<212> TYPE: PRT
<213> ORGANISM: Metarhizium acridum

<400> SEQUENCE: 92

Met Lys Ser Ala Leu Ile Ala Ala Ala Ala Leu

```
Leu Ala Asp Ala Pro Ile Glu Gln His Val Gln Ala Leu Gly Gln Lys
        35                  40                  45

Tyr Ile Gly Ala Arg Pro Pro Ser Arg Ala Ser Val Met Phe Asn Thr
 50                  55                  60

Lys Ala Pro Gln Val Ala Gly His Pro Val Pro Val Ser Asn Phe
 65                  70                  75                  80

Met Asn Ala Gln Tyr Phe Ser Glu Ile Thr Ile Gly Ser Pro Pro Gln
                 85                  90                  95

Ser Phe Lys Val Val Leu Asp Thr Gly Ser Ser Asn Leu Trp Val Pro
                100                 105                 110

Ser Gln Ser Cys Asn Ser Ile Ala Cys Tyr Leu His Ser Thr Tyr Asp
            115                 120                 125

Ser Ser Ser Ser Ser Thr Tyr Lys Lys Asn Gly Ser Ser Phe Glu Ile
        130                 135                 140

Arg Tyr Gly Ser Gly Ser Leu Ser Gly Phe Val Ser Gln Asp Val Val
145                 150                 155                 160

Ser Ile Gly Asp Leu Lys Ile Glu His Gln Asp Phe Ala Glu Ala Thr
                165                 170                 175

Ser Glu Pro Gly Leu Ala Phe Ala Phe Gly Lys Phe Asp Gly Ile Leu
            180                 185                 190

Gly Leu Gly Tyr Asp Thr Leu Ser Val Asn
        195                 200

<210> SEQ ID NO 93
<211> LENGTH: 202
<212> TYPE: PRT
<213> ORGANISM: Trichoderma atraviride

<400> SEQUENCE: 93

Met Lys Ser Ala Leu Ile Ala Ala Ala Leu Val Gly Ser Ala Gln
 1               5                  10                  15

Ala Gly Val His Lys Met Lys Leu Gln Lys Val Ser Leu Glu Gln Gln
                 20                  25                  30

Leu Glu Gly Ser Ser Ile Glu Ala Gln Val Gln Gln Leu Gly Gln Lys
            35                  40                  45

Tyr Met Gly Val Arg Pro Thr Ser Arg Val Asp Val Met Phe Asn Asp
 50                  55                  60

Asn Val Pro Lys Val Lys Gly Gly His Pro Val Pro Val Thr Asn Phe
 65                  70                  75                  80

Met Asn Ala Gln Tyr Phe Ser Glu Ile Thr Ile Gly Ser Pro Pro Gln
                 85                  90                  95

Thr Phe Lys Val Val Leu Asp Thr Gly Ser Ser Asn Leu Trp Val Pro
                100                 105                 110

Ser Gln Ser Cys Asn Ser Ile Ala Cys Phe Leu His Ser Thr Tyr Asp
            115                 120                 125

Ser Ser Ser Ser Ser Tyr Lys Lys Asn Gly Ser Asp Phe Glu Ile
        130                 135                 140

His Tyr Gly Ser Gly Ser Leu Thr Gly Phe Ile Ser Asn Asp Val Val
145                 150                 155                 160

Thr Ile Gly Asp Leu Gln Ile Lys Gly Gln Asp Phe Ala Glu Ala Thr
                165                 170                 175

Ser Glu Pro Gly Leu Ala Phe Ala Phe Gly Arg Phe Asp Gly Ile Leu
            180                 185                 190

Gly Leu Gly Tyr Asp Thr Ile Ser Val Asn
```

195                 200

<210> SEQ ID NO 94
<211> LENGTH: 203
<212> TYPE: PRT
<213> ORGANISM: Nectria haematococca

<400> SEQUENCE: 94

Met Lys Ser Ala Leu Leu Ala Ala Ala Leu Leu Gly Ser Ala Gln
1               5                   10                  15

Ala Gly Val His Lys Met Lys Ile Gln Lys Val Pro Leu Ala Glu Gln
                20                  25                  30

Leu Ala Thr Thr Ser Ile Glu Thr His Ile Gln Asn Leu Gly Gln Lys
            35                  40                  45

Tyr Leu Gly Ser Ala Arg Pro Lys Asn Gln Ala Asp Tyr Ala Phe Ser
    50                  55                  60

Thr Glu Ala Ile Asn Val Glu Gly Gly His Pro Val Pro Ile Ser Asn
65                  70                  75                  80

Phe Met Asn Ala Gln Tyr Phe Ser Glu Ile Thr Ile Gly Asn Pro Pro
                85                  90                  95

Gln Ser Phe Lys Val Val Leu Asp Thr Gly Ser Ser Asn Leu Trp Val
            100                 105                 110

Pro Ser Gln Glu Cys Gly Ser Ile Ala Cys Tyr Leu His Ser Lys Tyr
        115                 120                 125

Asp Ser Ser Ala Ser Ser Thr Tyr Lys Gln Asn Gly Ser Glu Phe Glu
    130                 135                 140

Ile His Tyr Gly Ser Gly Ser Leu Ser Gly Phe Ile Ser Asn Asp Asp
145                 150                 155                 160

Val Ser Ile Gly Asp Leu Lys Ile Lys Gly Gln Asp Phe Ala Glu Ala
                165                 170                 175

Thr Lys Glu Pro Gly Leu Ala Phe Ala Phe Gly Arg Phe Asp Gly Ile
            180                 185                 190

Leu Gly Leu Gly Tyr Asp Thr Ile Ser Val Asn
        195                 200

<210> SEQ ID NO 95
<211> LENGTH: 204
<212> TYPE: PRT
<213> ORGANISM: Grosmannia clavigera

<400> SEQUENCE: 95

Met Lys Gly Ala Leu Val Leu Ala Ala Ala Gly Leu Leu Gly Ser Ala
1               5                   10                  15

Gln Ala Ser Gly Ile Gln Lys Leu Lys Leu Lys Lys Val Pro Leu Ala
                20                  25                  30

Lys Gln Leu Glu Ser Ile Pro Ile Asp Ala Gln Ile Arg Gly Leu Gly
            35                  40                  45

Gln Lys Tyr Met Gly Ala Arg Leu Gly Ser His Ala Asp Glu Met Phe
    50                  55                  60

Lys Thr Ala Val Val Glu Thr Asp Asp Asn His Pro Leu Pro Val Ser
65                  70                  75                  80

Asn Phe Leu Asn Ala Gln Tyr Phe Ala Glu Ile Ser Ile Gly Thr Pro
                85                  90                  95

Pro Gln Ser Phe Lys Val Val Leu Asp Thr Gly Ser Ser Asn Leu Trp
            100                 105                 110

Val Pro Ser Ser Gln Cys Gly Ser Ile Ala Cys Tyr Leu His Thr Lys 115                 120                 125
Tyr Asp Ser Glu Ser Ser Ser Tyr Lys Asn Gly Ser Ala Phe
            130                 135                 140

Ala Ala Gln Tyr Gly Ser Gly Ser Leu Ser Gly Phe Val Ser Gln Asp
145                 150                 155                 160

Thr Val Ser Ile Gly Asp Leu Lys Ile Val Lys Gln Asp Phe Ala Glu
                165                 170                 175

Ala Thr Glu Glu Pro Gly Leu Ala Phe Ala Phe Ala Arg Phe Asp Gly
            180                 185                 190

Ile Leu Gly Leu Gly Phe Asp Thr Ile Ser Val Asn
            195                 200

<210> SEQ ID NO 96
<211> LENGTH: 1573
<212> TYPE: DNA
<213> ORGANISM: Trametes hirsuta

<400> SEQUENCE: 96

| | |
|---|---:|
| aattacatat gatactctcc agattcgccc ccctcgccct gctcccttc gtggccgccg | 60 |
| acggcgtcca caagctgaag ctcaccaagc ttcctcccgc aacttccaac ccgttgttgg | 120 |
| agagtgctta cctggctgag aagtatggtg gtggttccca gatgcccctt agcgcgggca | 180 |
| ttggccgcaa cgtccgcgtg tcgcgcccga ccgtcaagga cggcgaggag ctcttctgga | 240 |
| ctcaggacga gttttcgacc gagggcggtc acaacgttcc cttgagtagt acgtctcatt | 300 |
| cccttacata gtcggtgcat cgtctcataa caactgtcag acttcatgaa cgctcagtac | 360 |
| ttcgctgaaa tcaccttggg cactcccccg caatcggtac gtgacatatc tctctctggg | 420 |
| ggtcttcctc actcacttca gtttagttca aggtcatcct ggacactggg tacgtacaat | 480 |
| acatgcattt acgccgaacg atgactctga cagtcgccat tgtgttcagg tcgagcaacc | 540 |
| tctgggttcc gagcaccaag tgtacctcca ttgcgtgctt cctacacgcc aagtatgact | 600 |
| cgaccgcttc gtcgacatac aaggcgaacg gctccgagtt ctcgatccag tatggctctg | 660 |
| gctccatgga gggcttcgtc tcgcaagatg tcttgacaat tggtgacatc accatcaaga | 720 |
| accaagattt cgcagaggcc accaaggagc ccggcctcgc atttgccttt ggcaagtgag | 780 |
| tacaatctcg tgtcttcgca cttacctgta ctgaactatc acgcaaaggt tcgatggtat | 840 |
| cctcggcctg ggtatgacac ccatttccgt gaaccacatc actcctccct tctaccagat | 900 |
| gatgaaccag aagctcgtcg attctcctgt gttctctttc cgcctcggta gctcggaaga | 960 |
| ggacggtggt gaagccatct tcggaggagt cgatgagacc gcgtacagtg caagatcga | 1020 |
| atacgtccct gtcaggagga aggcgtactg ggaggtggag ctggagtcga tcaaactcgg | 1080 |
| agacgacgag cttgagctcg ataacaccgg cgctgccatc gacactggta aggtgaacac | 1140 |
| ccaacctcat gcagtattca caattgacac ctcgatagga acctcgttga ttgctctccc | 1200 |
| ctccgatctg gcggagatgc tcaatgcgca aatcggtgcc aagaagtcct ggaatggcca | 1260 |
| gtacaccgtc gactgcgcga aggtccctac cctcccccgac ctcaccttct acttcagcgg | 1320 |
| caagccttac actctcaagg gtaccgacta cgtcctcgaa gttcagggaa cttgcatgtc | 1380 |
| ctcgttcacc ggcatcgaca tcaatctgcc cggcggtggt gctctgtgga tcattggtac | 1440 |
| gctaacttta ttttgtgtgt tgtggtaagt gctgatttt gtctaggtga tgtcttcctg | 1500 |
| cgcaagtact acactgtgta cgaccatggc cgcgatgccg ttggcttcgc tcttgccaag | 1560 |
| tgactcgaga att | 1573 |

The invention claimed is:

1. A method of cleaving vinyl aromatics, the method comprising cleaving a vinyl aromatic in the presence of oxygen using an enzyme as a catalyst, wherein the enzyme comprises an amino acid sequence having at least 90% sequence identity to SEQ ID NO: 1 or SEQ ID NO: 2.

2. The method according to claim 1, wherein the enzyme comprises an amino acid sequence having at least 95% sequence identity to SEQ ID NO: 1 or SEQ ID NO: 2.

3. The method according to claim 1, wherein the enzyme comprises an amino acid sequence having at least 99% sequence identity to SEQ ID NO: 1 or SEQ ID NO: 2.

4. The method according to claim 1, wherein the cleaving is performed in further presence of $Mn^{3+}$ ions.

5. The method according to claim 1, wherein the cleaving is performed in an aqueous buffer at pH 6.

6. A method of preparing an isolated enzyme comprising the amino acid sequence of SEQ ID NO: 1 or SEQ ID NO: 2, the method comprising steps of:
   (i) culturing a strain of *Trametes hirsuta*; and
   (ii) recovering the enzyme from a cell-free extract of the culture of step (i).

7. The method according to claim 6, wherein the strain of *Trametes hirsuta* in step (i) is G FCC 047.

8. The method according to claim 6, wherein step (ii) is performed using hydrophobic interaction chromatography and anion exchange chromatography.

9. The method according to claim 6, wherein step (ii) is performed using a first hydrophobic interaction chromatography step, followed by anion exchange chromatography, followed by a second hydrophobic interaction chromatography step.

10. A method of recombinantly producing an isolated enzyme comprising the amino acid sequence of SEQ ID NO: 1 or SEQ ID NO: 2, the method comprising steps of:
    (i) transforming a nucleic acid comprising the nucleotide sequence of SEQ ID NO: 3 or SEQ ID NO: 4 into cells suitable for expressing the enzyme comprising the amino acid sequence of SEQ ID NO: 1 or SEQ ID NO: 2;
    (ii) incubating the cells under conditions suitable for expressing the enzyme in a culture broth; and
    (iii) isolating the expressed enzyme from the culture broth.

11. The method according to claim 10, wherein the cells of step (i) are *E. coli* or *Pichia pastoris* cells.

12. The method according to claim 10, wherein the nucleic acid of step (i) is ligated into a vector, and the vector is transformed into the cells.

13. The method according to claim 12, wherein the vector is a plasmid vector.

* * * * *